US010545073B2

(12) United States Patent
Pawliszyn et al.

(10) Patent No.: US 10,545,073 B2
(45) Date of Patent: Jan. 28, 2020

(54) METHOD AND INSTRUMENT FOR EXTRACTING A COMPONENT FROM A SAMPLE

(71) Applicant: JP Scientific Limited, Waterloo (CA)

(72) Inventors: Janusz Boleslaw Pawliszyn, Waterloo (CA); Justen James Poole, Wellesley (CA); Jonathan James Grandy, Waterloo (CA); Barbara Bojko, Waterloo (CA)

(73) Assignee: JP SCIENTIFIC LIMITED, Waterloo (CA)

(*) Notice: Subject to any disclaimer, the term of this patent is extended or adjusted under 35 U.S.C. 154(b) by 154 days.

(21) Appl. No.: 15/447,023

(22) Filed: Mar. 1, 2017

(65) Prior Publication Data
US 2017/0254729 A1 Sep. 7, 2017

Related U.S. Application Data

(60) Provisional application No. 62/302,674, filed on Mar. 2, 2016, provisional application No. 62/333,939, filed on May 10, 2016.

(51) Int. Cl.
| | |
|---|---|
| *G01N 1/08* | (2006.01) |
| *G01N 1/28* | (2006.01) |
| *G01N 1/36* | (2006.01) |
| *B01J 20/32* | (2006.01) |
| *G01N 30/00* | (2006.01) |
| *G01N 35/04* | (2006.01) |

(52) U.S. Cl.
CPC .............. *G01N 1/08* (2013.01); *G01N 1/286* (2013.01); *G01N 1/36* (2013.01); *B01J 20/3293* (2013.01);
(Continued)

(58) Field of Classification Search
CPC ............. G01N 1/405; G01N 2030/009; G01N 2030/062; G01N 2035/1053;
(Continued)

(56) References Cited

U.S. PATENT DOCUMENTS

| | | | | |
|---|---|---|---|---|
| 2,219,605 A | | 10/1940 | Henry | |
| 5,565,622 A | * | 10/1996 | Murphy | ................. G01N 1/405 73/61.55 |

(Continued)

OTHER PUBLICATIONS

Adomaviciute et al., "In-Groove Carbon Nanotubes Device for SPME of Aromatic Hydrocarbons," Chromatographia, Apr. 2008, vol. 67 (7-8), pp. 599-605.
(Continued)

*Primary Examiner* — Lyle Alexander
*Assistant Examiner* — Bryan Kilpatrick
(74) *Attorney, Agent, or Firm* — Borden Ladner Gervais LLP; David Nauman

(57) ABSTRACT

The present disclosure relates to a method and a solid phase microextraction sampling instrument for inserting into or through a solid or semisolid material to extract a component of interest from a sample, comprising a support structure at least partially coated with an extraction phase for extracting the component of interest, a protrusion that shields the coating during insertion, where the distances within a cross-sectional plane of the sampling instrument are greater than or equal to the corresponding distances in all of the cross-sectional planes located between the cross-sectional plane of interest and the insertion end of the sampling instrument. The present disclosure also discusses methods of making the instrument, desorption chambers, and methods for desorbing a component of interest from the instrument.

20 Claims, 47 Drawing Sheets

(52) U.S. Cl.
CPC ............... *G01N 2030/009* (2013.01); *G01N 2035/0434* (2013.01)

(58) Field of Classification Search
CPC ........ G01N 2560/00; G01N 1/02; G01N 1/08; G01N 2001/247; G01N 2001/2826; G01N 2035/0434; G01N 2035/1055; G01N 2001/4061; G01N 25/14; Y10T 436/255; B01J 20/3293
See application file for complete search history.

(56) References Cited

U.S. PATENT DOCUMENTS

| | | | |
|---|---|---|---|
| 6,042,787 | A | 3/2000 | Pawliszyn |
| 6,871,556 | B2 * | 3/2005 | Andresen ............. B01L 3/0275 422/429 |
| 7,384,794 | B2 | 6/2008 | Pawliszyn |
| 2005/0014156 | A1 * | 1/2005 | Pawliszyn ............... G01N 1/40 435/7.23 |
| 2014/0220701 | A1 | 8/2014 | Schueler et al. |

OTHER PUBLICATIONS

Chen et al., "Solid-Phase Microextraction Field Sampler," Analytical Chemistry, Nov. 2004, vol. 76 (22), pp. 6823-6828.
Helin et al., "Solid Phase Microextraction Arrow for the Sampling of Volatile Amines in Wastewater and Atmosphere," Journal of Chromatography A, Dec. 2015, vol. 1426, pp. 56-63.
International Patent Application No. PCT/CA2017/050278, International Search Report and Written Opinion dated Jun. 14, 2017.

* cited by examiner

METHOD AND INSTRUMENT FOR EXTRACTING A COMPONENT FROM A SAMPLE

CROSS-REFERENCE TO RELATED APPLICATIONS

This application claims the benefit of priority of U.S. Provisional Patent Application No. 62/302,674 filed Mar. 2, 2016, and U.S. Provisional Patent Application No. 62/333,939 filed May 10, 2016, which are hereby incorporated by reference.

FIELD

The present disclosure relates to a method and instrument for solid phase microextraction for extracting a component of interest from a sample.

BACKGROUND

The following paragraphs are not an admission that anything discussed in them is prior art or part of the knowledge of persons skilled in the art.

Solid phase microextraction (SPME) is an approach for sample preparation that may be used in various analytical methods. SPME devices include an extraction coating present on a support. The extraction coating includes adsorptive particles, which may have different geometries. Exposure of the SPME device directly into a matrix or into its headspace, for a certain period of time, extracts and enriches analytes contained in the sample matrix.

The SPME process is governed by the partitioning of analytes from the matrix onto or into the extraction phase, and extraction efficiency of an analyte depends on the analyte's affinity toward the adsorptive particles present in the extraction coating.

After extraction and enrichment of the analytes onto or into the extraction phase, the SPME device may be placed in an analytical device where the analytes are desorbed and analyzed.

Adomaviciute et al., "In-Groove Carbon Nanotube Device for SPME of Aromatic Hydrocarbons", *Chromatographia*, 2008, 67, 599-605 teaches a SPME fiber with a coating incorporated into a groove of a stainless steel rod and mounted inside an external needle.

U.S. Patent Publication 2014/0220701 teaches an extractor device that has a tip which protects the extractor during penetration into a separating layer.

INTRODUCTION

The following introduction is intended to introduce the reader to this specification but not to define any invention. One or more inventions may reside in a combination or sub-combination of the instrument elements or method steps described below or in other parts of this document. The inventors do not waive or disclaim their rights to any invention or inventions disclosed in this specification merely by not describing such other invention or inventions in the claims.

Solid phase microextraction (SPME) fiber assemblies have become a common sampling method in analytical laboratories. Such fibers have been employed to extract components of interest from a variety of sample matrices including: environmental air, surface waters, fruits, vegetables, blood, urine, organ tissue, muscle tissue and even brain tissue. SPME fibers may be damaged when directly inserted into or through solid or semisolid materials. For example, friction between the solid or semisolid materials may cause the coating to disassociate from the fiber. SPME fibers may damage solid or semisolid materials when removed from said materials. SPME fibers may be located in a device that protects the fiber, including its coating, during insertion into or through the solid or semisolid material, and may protect the solid or semisolid materials when the SPME fiber is removed from the materials. Once the fiber and protective device are positioned in the sample, the fiber and the protective device must be manipulated to expose at least a portion of the fiber to the sample matrix to allow extraction of the component of interest. Once the extraction is complete, the fiber and the protective device must once again be manipulated to protect the fiber for withdrawal from or through the solid or semisolid material.

The process of introducing SPME fibers with a protective device into or through a solid or semisolid material, such as biological tissues, may produce an undesirably large footprint in the sample. Furthermore, introducing two components, the SPME fiber and the protective device, into or through a solid or semisolid material, as well as their manipulation, may be cumbersome, for example in methods that require a certain level of precision. The required level of precision may be heightened in samples that are living, moving, or a combination thereof. Additionally, using two components, the SPME fiber and the protective device, may be undesirable for methods performed by health-care practitioners, who may not be familiar with operating a device that requires manipulation.

There remains a need for a solid phase microextraction device lacking a separate protective device that exhibits reduced damage when directly inserted into or through a solid or semisolid material, where the reduced damage is in comparison to known SPME fibers without a protective device. There also remains a need for a solid phase microextraction device lacking a separate protective device that reduces damage to a solid or semisolid material when withdrawn from the materials, where the reduced damage is in comparison to withdrawal of known SPME fibers without a protective device.

The present disclosure provides a solid phase microextraction sampling instrument lacking a separate protective device, for inserting into or through a solid or semisolid material to extract a component of interest from a sample. Generally, the instrument shields the extraction coating during the insertion of the instrument by reducing the interaction between the leading edge of the coating and the solid or semisolid material, and optionally by reducing the friction between the coating and the solid or semisolid material. The instrument may have an outer surface that reduces or avoids interaction between a trailing edge of the instrument and the solid or semisolid material during withdrawal of the instrument, and optionally by reducing the friction between a trailing edge of the instrument and the solid or semisolid material.

The shielding may be achieved by having a support structure with a protrusion that projects with a height from the support structure that is approximately equal to the thickness of the extraction phase coating where the extraction phase coating abuts the protrusion, and where the coating is on the trailing side of the protrusion in reference to the direction of insertion. The outer surface that reduces or avoids interaction between the instrument and the material may be achieved by each cross-sectional plane along the insertion portion of the support structure being the same size or larger than each of the other cross-sectional planes located between the plane of interest and the insertion end of the support structure.

The present disclosure also discusses methods of extracting a component of interest from a sample using the instrument described above, as well as methods of making the above described instrument.

The present disclosure also discusses methods of desorption and desorption chambers for desorbing a component of interest from an instrument described above.

The present disclosure provides a solid phase microextraction sampling instrument for inserting into or through a solid or semisolid material to extract a component of interest from a sample, comprising a support structure at least partially coated with an extraction phase for extracting the component of interest, the support structure having an insertion portion for inserting into or through the material and into the sample, the insertion portion comprising a protrusion defining a leading protrusion side and a trailing protrusion side of the insertion portion, where the extraction phase is located at least on the trailing protrusion side of the protrusion and abuts a trailing side edge of the protrusion, and where the protrusion projects with a height from the support structure that is approximately equal to the thickness of the extraction phase where the extraction phase abuts the protrusion to shield the coating during insertion in a direction along the axis of insertion of the support structure, and where the distances within a cross-sectional plane in the insertion portion that extend from the axis of insertion to the outer edge of the sampling instrument are greater than or equal to the corresponding distances in all of the cross-sectional planes located between the cross-sectional plane of interest and the insertion end of the insertion portion.

The sampling instrument according to the present disclosure may be sheathless. In some examples according to the present disclosure, the trailing side edge of the protrusion may be substantially perpendicular to the support structure. In some examples according to the present disclosure, the protrusion may extend around the circumference of the insertion portion of the support structure.

In some examples according to the present disclosure, the sampling instrument may comprise a plurality of protrusions. The heights of each one of the plurality of protrusions may be approximately equal. In some examples according to the present disclosure, adjacent pairs of protrusions may be separated by a distance from about 0.01 mm to about 2.0 cm. The extraction phase may be located between every adjacent pair of protrusions. In some examples according to the present disclosure, the support structure may comprise one protrusion that extends around the circumference of the support structure in a screw-like configuration. Adjacent threads of the screw-like protrusion may be separated by a distance from about 0.01 mm to about 2.0 mm. The extraction phase may be located between every adjacent pair of threads. In some examples according to the present disclosure, the height of the protrusion may be from about 1 µm to about 1.0 cm.

The extraction phase may comprise a sorptive polymer or a combination of a polymer and a sorptive material immobilized in the polymer. The sorptive material may comprise particles, polymers, nanosheets, nanotubes, or any combination thereof. The sorptive material may be inorganic, organic, or an inorganic/organic hybrid. The sorptive material may comprise normal-phase silica particles, C-1/silica particles, C-4/silica particles, C-6/silica particles, C-8/silica particles, C-18/silica particles, C-30/silica particles, reverse-phase amide silica particles, HS-F5/silica particles, phenyl/silica particles, cyano/silica particles, diol/silica particles, ionic liquid/silica particles, molecular imprinted polymer particles, hydrophilic-lipophilic-balanced (HLB) particles, carboxen 1006 particles, carbowax particles, divinylbenzene (DVB) particles, octadecylsilane particles, nanoparticles, processed mineral based particles, carbon nanotubes, functionalized-carbon nanotubes, graphene, graphene oxide, functionalized-graphene, quantum dots, or any combination thereof. The polymer may comprise substituted or unsubstituted poly(dimethylsiloxane), polyacrylate, poly(ethylene glycol), poly(divinylbenzene), polypyrrole, derivatised cellulose, chitin, or chitosan. The sorptive polymer may comprise an organic polymer. The organic polymer may comprise poly di-vinyl benzene (DVD), polydimethysiloxane (PDMS), hydrophilic lipophilic balanced (HLB), or polyethylene glycol (PEG).

In some examples according to the present disclosure, the support structure may be made of metal or metal alloy. The metal or metal alloy may be steel, stainless steel, or nickel-titanium alloy. In other examples according to the present disclosure, the support structure may be a polymer. The polymer may be polybutylene terephthalate, polyether ether ketone, polyethylene, or polyhexamethylene adipamide. In other examples according to the present disclosure, the support structure may be fused silica. In other examples according to the present disclosure, the support structure is a carbon lattice. The carbon lattice may be comprised of carbon fibers, or carbon nanotube superstructures. In other examples according to the present disclosure, the support structure may be made of wood.

In some examples according to the present disclosure, the support structure may be in the form of a needle, a pin, a flat blade, a bolt, or a screw. The needle may be a biopsy needle. The needle may be a stainless steel needle. The needle may have a thickness from about 0.03 mm to about 3.00 mm.

In some examples according to the present disclosure, the support structure may be configured to control the depth of insertion into the sample. The support structure may be configured to be coupled to a spring loaded propelling device or a compressed air firing device. The compressed air firing device may be an Airsoft™ gun. The spring loaded propelling device may be an AccuCheck™ meter.

In some examples according to the present disclosure, the support structure may be a bolt. The bolt may have a thickness from about 0.5 mm to about 15.0 mm.

In some examples according to the present disclosure, the sampling instrument may further comprise an additional coating located over at least the insertion portion of the instrument. The additional coating may be comprised of a biocompatible polymeric coating. The biocompatible polymeric coating may comprise polyacrylonitrile, Polytetrafluoroethylene, polydimethylsiloxane, polyethylene glycol, or a combination thereof.

In some examples according to the present disclosure, the solid or semisolid material may be a tissue, a membrane, or a septum. The solid or semisolid material may be part of the sample. The solid or semisolid material may be the same as the sample. In some examples according to the present disclosure, the sample may be a fruit, a vegetable, or a biological tissue. The biological tissue may be organ tissue, epithelial tissue, muscle tissue, nervous tissue, connective tissue, or mineralized tissue. The biological tissue may be brain tissue. The biological tissue may be fish tissue.

In some examples according to the present disclosure, the component of interest may be a bacteria, a virus, a subcellular component, a biopolymer, DNA, a protein, a drug, a drug metabolite, a hormone, a vitamin, an environmental contaminant, a chemical, a cell, or a combination thereof.

The present disclosure provides a method for extracting a component of interest from a sample, the method comprising inserting an instrument as described above into or through a solid or semisolid material and into the sample, sorbing the component of interest, and removing the instrument from the sample. The method may further comprise positioning the extraction phase into an analytical instrument for desorption, and measurement or identification of the component of interest. The analytical instrument may be an electrospray ionization mass spectrometer.

The present disclosure provides a method of making a solid phase microextraction sampling instrument for inserting into or through a solid or semisolid material to extract a component of interest from a sample, comprising dipping a support structure into an extraction phase, the support structure having an insertion portion for inserting into or through the material and into the sample, the insertion portion comprising a protrusion defining a leading side and a trailing side of the insertion portion, where the extraction phase contacts at least on the trailing side of the protrusion and abuts a trailing side edge of the protrusion, and sliding the support structure through an aperture of a membrane that is slightly larger than the support structure so that the membrane removes extraction phase to generate a coated support structure having an approximately constant cross-sectional area.

The present disclosure provides a desorption chamber for desorbing a component of interest from an instrument as described above, where the desorption chamber comprises a housing for holding the instrument, and comprising a membrane having an aperture adapted to receive the leading side of the instrument, the aperture having fluid communication therebetween with an analytical instrument, and a valve for introducing desorption solvent into the housing, where when the instrument is received by the membrane, the instrument blocks the fluid communication. The analytical instrument may be an electrospray ionization mass spectrometer.

The present disclosure provides a method for desorbing a component of interest from an instrument as described above, comprising positioning the instrument into the desorption chamber as described above, the membrane receiving the instrument, introducing desorption solvent into the housing, desorbing the component of interest, removing the instrument from the desorption chamber, and emptying the desorption chamber of the desorption solvent containing the component of interest.

Other aspects and features of the present disclosure will become apparent to those ordinarily skilled in the art upon review of the following description of specific examples in conjunction with the accompanying figures.

BRIEF DESCRIPTION OF THE DRAWINGS

Examples of the presently disclosed methods and instruments will now be described, by way of example only, with reference to the attached Figures.

FIG. 1A is a schematic of a side view of the instrument having cross-sectional planes A-A and B-B. FIG. 1B is a schematic of cross-sectional planes A-A and B-B.

FIG. 4A is a schematic of the side view of the instrument. FIG. 4B is a schematic of a cross sectional view along the axis of insertion of the instrument.

FIG. 5A is a schematic of the side view of the instrument. FIG. 5B is a schematic of a cross sectional view along the axis of insertion of the instrument.

FIG. 6A is a schematic of the side view of the instrument. FIG. 6B is a schematic of a side view that is adjacent to the view in FIG. 6A of the instrument.

FIG. 16A are images captured before gun-assisted puncture of fish scales. FIG. 16B are images captured after gun-assisted puncture of fish scales.

FIG. 17A is when the component of interest is Sertraline. FIG. 17B is when the component of interest is Fluoxetine, Paroxetine, Diaxepam, or Salbutamol. FIG. 17C is when the component of interest is Ranitidine or Codeine.

FIG. 18A is when the component of interest is Paroxetine. FIG. 18B is when the component of interest is Diazepam. FIG. 18C is when the component of interest is Salbutamol. FIG. 18D is when the component of interest is Fluoxetine. FIG. 18E is when the component of interest is Ranitidine.

FIG. 18F is when the component of interest is Sertraline. FIG. 18G is when the component of interest is Codeine.

FIG. 26A: m/z 129.04270. FIG. 26B: m/z 204.13614 based on the data in FIG. 25.

FIG. 27A is an image captured during sampling collection and component extraction. FIG. 27B is an image captured after sampling collection and component extraction.

DETAILED DESCRIPTION

Figure 1A:
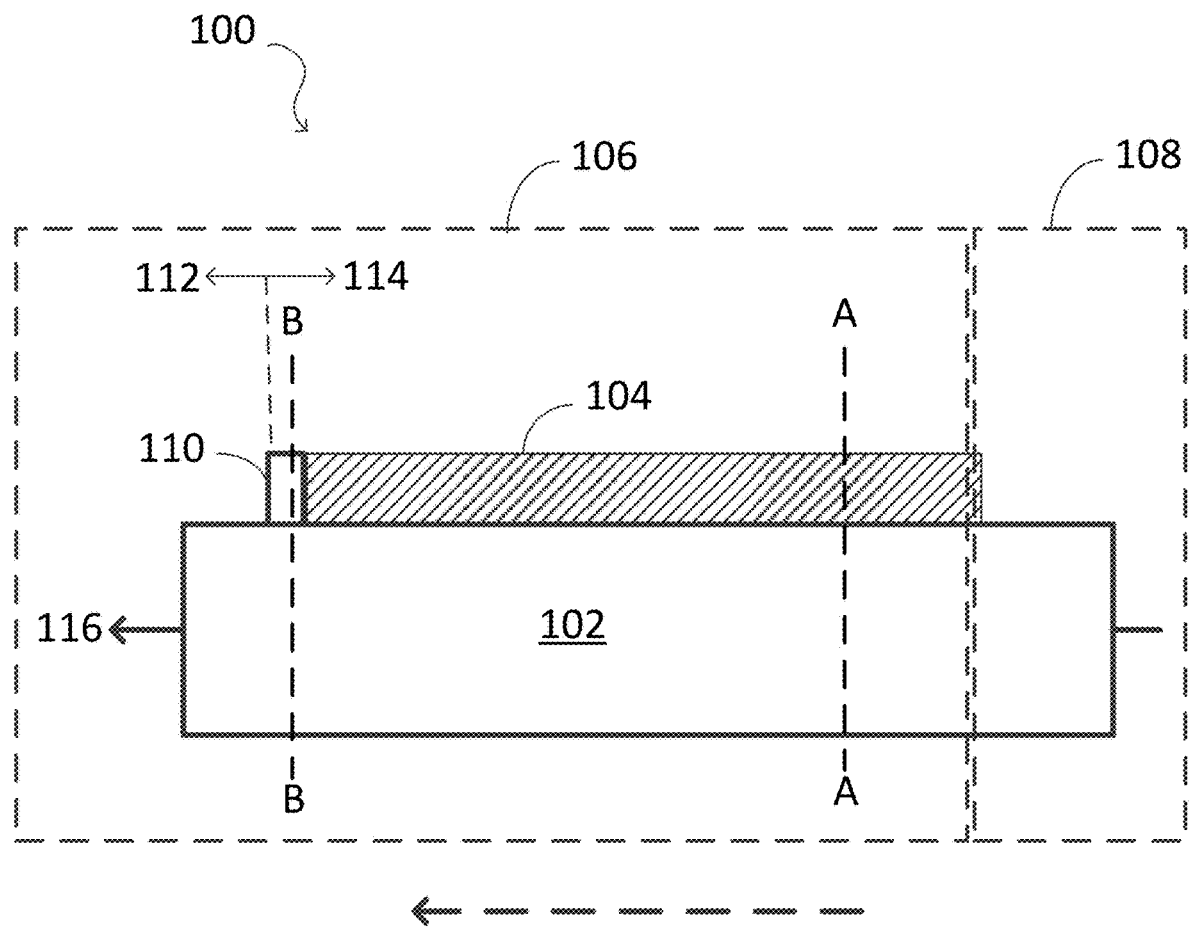
FIGS. 1A-B are schematics of an example of a sampling instrument according to the present disclosure.

Generally, the present disclosure provides a solid phase microextraction sampling instrument for inserting into or through a solid or semisolid material to extract a component of interest from a sample. The sampling instrument comprises a support structure at least partially coated with an extraction phase for extracting the component of interest, the support structure having an insertion portion for inserting into or through the material and into the sample. The insertion portion comprises a protrusion defining a leading side and a trailing side of the insertion portion, where the extraction phase is located at least on the trailing side of the protrusion and abuts a trailing side edge of the protrusion. The protrusion projects with a height from the support structure that is approximately equal to the thickness of the extraction phase where the extraction phase abuts the protrusion to shield the coating during insertion in a direction along the axis of insertion of the support structure. The distances within a cross-sectional plane in the insertion portion that extend from the axis of insertion to the outer edge of the sampling instrument are greater than or equal to the corresponding distances in all of the cross-sectional planes located between the cross-sectional plane of interest and the insertion end of the insertion portion.

The present disclosure also provides a method for extracting a component of interest from a sample. The method comprises inserting an instrument as provided by the present disclosure into or through a solid or semisolid material and into the sample, sorbing the component of interest, and removing the instrument from the sample.

The present disclosure further provides a method of making a solid phase microextraction sampling instrument for inserting into or through a solid or semisolid material to extract a component of interest from a sample. The method comprises dipping a support structure into an extraction phase, the support structure having an insertion portion for inserting into or through the material and into the sample, and comprising a protrusion defining a leading side and a trailing side of the insertion portion, where the extraction phase contacts at least on the trailing side of the protrusion and abuts a trailing side edge of the protrusion. The method also comprises sliding the support structure through an aperture of a membrane that is slightly larger than the support structure so that the membrane removes extraction phase to generate a coated support structure having an approximately constant cross-sectional area.

The present disclosure further provides a desorption chamber for desorbing a component of interest from a sampling instrument as provided by the present disclosure. The desorption chamber comprises a housing for holding the instrument, and comprising a membrane having an aperture adapted to receive the leading side of the instrument, the aperture having fluid communication therebetween with an analytical instrument, and a valve for introducing desorption solvent into the housing, where when the instrument is received by the membrane, the instrument blocks the fluid communication.

The present disclosure further provides a method for desorbing a component of interest from a sampling instrument as provided by the present disclosure. The method comprises positioning the instrument into a desorption chamber as provided by the present disclosure, the membrane receiving the instrument, introducing desorption solvent into the housing, desorbing the component of interest, removing the instrument from the desorption chamber, and emptying the desorption chamber of the desorption solvent containing the component of interest.

In the context of the present disclosure, solid phase microextraction refers to a process of exposing an instrument or device coated with an extraction phase to a sample for a sufficient amount of time to allow a sample component to sorb to the extraction phase. The process of sorbing occurs by the mechanism of diffusion and is referred to as "chemical extraction" or "extraction" hereon in. After the extraction, the instrument or device is removed from the sample and the sample component may be desorbed and analyzed. If the extraction phase is allowed to come into equilibrium with the sample component in the sample, the amount of the extracted component is proportional to its concentration in the sample.

In the context of the present disclosure, "sorb" or "sorption" refers to absorption, adsorption, or a combination thereof.

Inserting a sampling instrument according to the present disclosure into or through a solid or semisolid material and into the sample refers to any forcible method that positions the extraction phase coating of the sampling instrument within the sample to sorb a component of interest. The portion of the sampling instrument that is inserted through the solid or semisolid material, the sample, or a combination thereof, is referred to as the insertion portion of the sampling instrument. In some examples according to the present disclosure, a portion of the sampling instrument is not inserted through the solid or semisolid material, the sample, or a combination thereof, which is referred to as the non-insertion portion of the sampling instrument.

The solid or semisolid material is any substance that has solid-like properties or semisolid-like properties and has a sufficient rigidity or viscosity such that the interaction created between the material and the sampling instrument during insertion is sufficient to disassociate at least some of the extraction phase coating from a sampling instrument that lacks a shield to protect the coating from such interaction. The solid or semisolid material may have a durability such that the material is damaged when a sampling instrument according to U.S. Patent Publication 2014/0220701 is withdrawn from the material.

The solid or semisolid material may be connected to the sample. For example, the solid or semisolid material may be: (1) a protective layer on the sample; (2) an outer surface on the sample; or (3) a combination thereof. In some examples according to the present disclosure, the solid or semisolid material forms a portion of the sample. Alternatively, the solid or semisolid material may be spatially separated from the sample. For example, the solid or semisolid material may be a septum attached to a container housing the sample. In other alternatives, the solid or semisolid material may be the sample, or may be a part of the sample. For example, the solid or semisolid material may be: (1) a protective layer of the sample; (2) an outer surface of the sample; or (3) a combination thereof.

In the context of the present disclosure, solid-like properties refer to structural rigidity and a resistance to change of shape or volume. Semisolid-like properties refer to solid-like properties but with the ability to flow under pressure. In some examples according to the present disclosure, the solid or semisolid material is a membrane, a tissue or a septum. A membrane may be any organic or inorganic barrier. In some examples according to the present disclosure, the membrane is a tissue membrane that covers the body, lines a body cavity, or covers an organ. In other examples according to the present disclosure, the membrane is a rubber membrane. A tissue may be any organic or inorganic group of elements that form a structural material. In some examples according to the present disclosure, the tissue may be a group of cells such as from a multi-celled organism. For example the tissue may be from an egg, a mouse, a rat, a rabbit, a dog, a sheep, a pig, a monkey, a fish, or a human. A septum may be an organic or inorganic dividing wall. In some examples according to the present disclosure, the septum is a rubber septum.

The sample is any solid, semisolid, liquid or gaseous substance that may contain the component of interest. In some examples according to the present disclosure, the sample is a tissue, cellular components of a tissue, or an extract from a tissue. In the context of the present disclosure, a tissue is a group of cells. The tissue may be a group of single cell organisms, such as a culture of bacteria or yeast, or a group of cells such as from a multi-celled organism. For example the tissue may be from an egg, a mouse, a rat, a rabbit, a dog, a sheep, a pig, a monkey, a fish, or a human. In some examples according to the present disclosure, the tissue sample has been extracted from its source, for example, the tissue sample may be isolated cells or organs. In other examples according to the present disclosure, the tissue sample has not been extracted from its source and the solid phase microextraction method is performed on a living animal or fish. In some examples according to the present disclosure, the tissue sample is organ tissue, epithelial tissue, muscle tissue, nervous tissue, connective tissue, or mineralized tissue. In some examples according to the present disclosure, the tissue sample is a human brain, a human appendage, a human organ, a human bodily region possessing muscle of fatty tissue, or similar body regions in animals such as fish, mice, birds, or amphibians. Examples of human bodily regions that possess muscle or fatty tissue are a liver, kidney, lung, brain, pancreas, stomach, gut, intestine, and ovary. In some examples according to the present disclosure, the sample is a fruit or a vegetable. In some examples according to the present disclosure, the sample is a tissue sample and the solid or semisolid material is the outer surface of the tissue sample. In some examples according to the present disclosure, the solid or semisolid material is the same as the sample.

In some examples according to the present disclosure, the sampling instrument is pushed through the material and into the sample. In other examples according to the present disclosure, the sampling instrument is pulled through the material and into the sample. In yet further examples according to the present disclosure, the sampling instrument is both pushed and pulled through the material and into the sample. The push or pull force may be generated by a user or by a mechanical device. Some examples of a mechanical device for pushing or pulling the sampling instrument are a spring loaded propelling device or a compressed air firing device. The air firing device may be a device that: (1) is available and easily accessible by the public; (2) easy to use without training; (3) is sufficiently robust to have a low probability of malfunctions during repetitive use; or (4) a combination thereof. In some examples according to the present disclosure, the air firing device is an Airsoft™ gun. The spring loaded propelling device may be a device that: (1) is available and easily accessible by the public; (2) easy to use without training; (3) is sufficiently robust to have a low probability of malfunctions during repetitive use; (4) has a needle that is hidden and protected; or (5) a combination thereof. In some examples according to the present disclosure, the spring loaded propelling device is a commercially available finger pricking device, for example the Accu-Check™ meter. The use of a spring loaded propelling device or compressed air firing device may: (1) allow for easier and uniform penetration into and through the solid or semisolid material, the sample, or a combination thereof; (2) allow for controlled depth of insertion into the sample; (3) allow for easier in vivo sampling of organism samples that are aggressive, difficult to capture, or a combination thereof; or (4) a combination thereof.

In some examples according to the present disclosure, the sampling instrument may be configured to: (1) improve the user's grasp of the sampling instrument; (2) couple to a spring loaded propelling device or a compressed air firing device; or (3) a combination thereof. In other examples according to the present disclosure, the sampling instrument comprises a linker that is coupleable to: (1) a handle to improve the user's grasp of the sampling instrument; (2) a spring loaded propelling device or a compressed air firing device; or (3) a combination thereof.

With what will be explained in more detail below, any direction of insertion of the sampling instrument may be chosen provided that the projection shields the extraction phase coating during the insertion. The support structures of sampling instruments according to the present disclosure have an axis of insertion which is in reference to the direction of insertion. The direction of withdrawing the sampling instrument from the sample after extraction may be generally along the same path of insertion. In some examples according to the present disclosure, the entirety of the sampling instrument is passed through the sample in one direction, for example, when the sample is a fruit or a vegetable.

The sampling instrument may be inserted at any depth within the sample provided that the extraction phase coating is able to sorb the component of interest. In some examples according to the present disclosure, the depth of insertion is controlled to perform depth profiling of the sample, which is explained in more detail below.

The support structure is any body that can be inserted into or through a solid or semisolid material and into the sample without becoming impaired, and that can be coated, at least partially, with an extraction phase. In the context of the present disclosure, becoming impaired refers to a weakened or damaged state that can no longer sufficiently function as intended. The shape and size of the support structure may be chosen depending on: (1) the sample; (2) cost constraints; or (3) a combination thereof. Any size and shape of the support structure may be chosen provided that each cross-sectional plane along the insertion portion is the same size or larger than each of the other cross-sectional planes located between the plane of interest and the insertion end of the insertion portion. The expression "the same size or larger" should be understood to mean that the distances that extend from the axis of insertion to the outer edge of the SPME instrument within a cross-sectional plane are greater than or equal to the corresponding distances in all of the planes located between the plane of interest and the insertion end. In the context of the present disclosure, the "cross-sectional plane" refers to any plane that intersects the support structure at a right angle to the axis of insertion of the support structure. The "distances within a cross-sectional plane" refers to the distances of all of the vectors in the cross-sectional plane that extend 360° from the axis of insertion of the support structure to the outer most edge of the SPME instrument. A "corresponding distance" refers to an equivalent vector located in another cross-sectional plane. In some examples according to the present disclosure, the sampling instrument lacks a jut that can scrape the solid or semisolid material, the sample, or a combination thereof when the sampling instrument is withdrawn from the solid or semisolid material, the sample, or a combination thereof. In some examples according to the present disclosure, the corresponding distances in all cross-sectional planes located from the protrusion to the trailing edge of the insertion portion of the support structure are about equal.

In some examples according to the present disclosure, the support structure has a cylinder-like shape with a diameter from about 0.01 mm to about 0.7 mm, for example, 0.01 mm, 0.05 mm, 0.1 mm, 0.2 mm, 0.3 mm, 0.4 mm, 0.5 mm, 0.6 mm, 0.7 mm; or the diameter is from any one of the diameters listed above to any other of the diameters listed above. In some examples according to the present disclosure, the support structure has a cylinder-like shape with a diameter of about 0.2 mm or less, for example when: (1) reducing agitation or damage of a tissue sample, for example brain tissue; (2) introducing the sampling instrument directly into a nanospray or mass spectrometer; or (3) a combination thereof, is desirable. In other examples according to the present disclosure, the support structure has a cylinder-like shape with a diameter of about 0.7 mm, for example when increasing the amount of the extraction phase and the sensitivity of the extraction is desirable.

The length of the support structure along the axis of insertion may be selected depending on the desirable depth of extraction in the sample. In some examples according to the present disclosure, the length of the support structure is larger, for example when: (1) the portion of the sample to be sampled is at a greater depth; (2) a larger surface area of extraction is desirable; or (3) a combination thereof. In some examples according to the present disclosure, the support structure has a length from about 1.0 cm to about 30.0 cm, for example, 1.0 cm, 2.0 cm, 3.0 cm, 4.0 cm, 5.0 cm, 10.0 cm, 15.0 cm, 20.0 cm, 25.0 cm, 30.0 cm; or the length is from any one of the lengths listed above to any other of the lengths listed above. In some examples according to the present disclosure, the length of the support structure is larger and the length of the extraction phase coating is smaller, for example when the sample is a sensitive tissue sample such as brain tissue.

In some examples according to the present disclosure, the support structure has an elongated cylinder-like shape, for example when a cylindrical excision in the solid or semisolid material and the sample is desirable. In some examples according to the present disclosure, the support structure has a needle-like shape, for example when the solid or semisolid material, the sample, or a combination thereof has an increased rigidity or viscosity or a protective layer that must be punctured, for example fish scales, dura of the brain, epithelial tissue, consumer product packaging, or the skin of a fruit or vegetable. In some examples according to the present disclosure, the support structure has a blade-like shape, for example when a larger surface area of the support structure to increase the amount of extraction phase coating and the sensitivity of the extraction is desired over decreasing the invasiveness of the sampling. In some examples according the present disclosure, the support structure has a bolt-like shape, for example when providing mechanical support to the sample body such as a multi-pin sampler body, is desirable. In some examples according to the present disclosure, the thickness of the support structure is from about 0.05 mm to about 15.0 mm, for example, 0.05 mm, 0.1 mm, 0.25 mm, 0.50 mm 0.75 mm, 1.0 mm, 1.5 mm, 2.0 mm, 2.5 mm, 3.0 mm, 4.0 mm 5.0 mm, 6.0 mm, 7.0 mm, 8.0 mm, 9.0 mm, 10.0 mm, 11.0 mm, 12.0 mm, 13.0 mm, 14.0 mm, 15.0 mm; or the thickness is from any one of the thicknesses listed above to any other of the thicknesses listed above. A support structure having a needle-like shape may have, for example, a thickness from about 0.03 mm to about 3.0 mm, for example, 0.03 mm, 0.05 mm, 0.1 mm, 0.25 mm, 0.50 mm 0.75 mm, 1.0 mm, 1.5 mm, 2.0 mm, 2.5 mm, 3.0 mm thick; or the thickness is from any one of the thicknesses listed above to any other of the thicknesses listed above. A support structure having a bolt-like shape may have for example, a thickness from about 0.5 mm to about 15.0 mm, for example, 0.5 mm, 1.0 mm, 2.0 mm, 3.0 mm, 4.0 mm 5.0 mm, 6.0 mm, 7.0 mm, 8.0 mm, 9.0 mm, 10.0 mm, 11.0 mm, 12.0 mm, 13.0 mm, 14.0 mm, 15.0 mm thick; or the thickness is from any one of the thicknesses listed above to any other of the thicknesses listed above. A support structure having a blade-like shape may have, for example, a thickness from about 0.03 mm to about 3.0 mm, for example, 0.03 mm, 0.05 mm, 0.1 mm, 0.25 mm, 0.50 mm, 0.75 mm, 1.0 mm, 1.5 mm, 2.0 mm, 2.5 mm, 3.0 mm; or the thickness is from any one of the thicknesses listed above to any other of the thicknesses listed above.

The support structure may be made of any material that can be inserted into or through a solid or semisolid material and into a sample without becoming impaired. The material of the support structure may be chosen depending on: (1) the sample; (2) cost constraints; or (3) a combination thereof. In some examples according to the present disclosure, the support structure is made of a suitable metal or metal alloy, for example when the solid or semisolid material, the sample, or a combination thereof has an increased rigidity or viscosity. Examples of suitable metal or metal alloy are steel, stainless steel, or nickel-titanium alloy. In some examples according to the present disclosure, the support structure is a suitable polymer, for example when: (1) lowering the cost and improving the manufacture process of the support structure is desirable; (2) novel designs, intricate designs, varied designs, or a combination thereof, are desirable; or (3) a combination thereof. Examples of a suitable polymer are polybutylene terephthalate, polyether ether ketone, or polyhexamethylene adipamide. In some examples according to the present disclosure, the support structure is fused silica. In some examples according to the present disclosure, the support structure is a suitable carbon lattice, for example when: (1) enhancing the sensitivity of the extraction process over longer extraction times; (2) increasing the strength to diameter size ratio of the support structure; (3) combining the support structure with nanoparticles; or (4) a combination thereof, is desirable. Examples of a suitable carbon lattices are comprised of carbon fibers, or carbon nanotube superstructures. In some examples according to the present disclosure, the support structure is made of wood, for example when paper spray ionization is used with a sampling instrument and method provided by the present disclosure.

The insertion portion of the support structure is any portion that: (1) is inserted into or through the solid or semisolid material and into the sample; and (2) is at least partially coated with an extraction phase. Any size and shape of the insertion portion may be chosen provided that each cross-sectional plane along the insertion portion is the same size or larger than each of the other cross-sectional planes located between the plane of interest and the insertion end of the insertion portion, for example to: (1) reduce the interaction between the trailing edge of the insertion portion with the solid or semisolid material, the sample, or a combination thereof; (2) reduce the friction between the trailing edge of the insertion portion with the solid or semisolid material, the sample, or a combination thereof; or (3) a combination thereof, during withdrawal of the sampling instrument.

An SPME device that has a cross-sectional plane along the insertion portion that is smaller than at least one of the other cross-sectional planes located between the plane of interest and the insertion end, and creates a jut that may damage some of the solid or semisolid material, the sample, or a combination thereof, during withdrawal of the instrument. An otherwise identical instrument where each cross-sectional plane along the insertion portion is the same size or larger than each of the other cross-sectional planes located between the plane of interest and the insertion end lessens the damage of the solid or semisolid material, the sample, or a combination thereof, during withdrawal of the instrument. An SPME device that has a cross-sectional plane along the insertion portion that is smaller than at least one of the other cross-sectional planes located between the plane of interest and the insertion end is not able to be withdrawn from the sample in the same direction of insertion into the sample without increasing damage to the sample. An otherwise identical instrument where each cross-sectional plane along the insertion portion is the same size or larger than each of the other cross-sectional planes located between the plane of interest and the insertion end decreases damage to the sample when it is withdrawn from the sample in the same direction of insertion. An SPME device that has a cross-sectional plane along the insertion portion that is smaller than at least one of the other cross-sectional planes located between the plane of interest and the insertion end is not able to perform rapid sampling without increasing damage to the sample. An otherwise identical instrument where each cross-sectional plane along the insertion portion is the same size or larger than each of the other cross-sectional planes located between the plane of interest and the insertion end decreases damage to the sample when performing rapid sampling.

In some examples according to the present disclosure, at least about 5%, at least about 10%, at least about 25%, at least about 50%, at least about 75%, at least about 90%, at least about 95%, or 100% of the support structure forms the insertion portion. In some examples according to the present disclosure, from about 50% to about 95% of the support structure forms the insertion portion.

The protrusion may be any type of projection that has a height that is approximately equal to the thickness of the extraction phase where the extraction phase abuts the protrusion, and shields the extraction phase coating during insertion. In the context of the present disclosure, shielding the extraction phase coating during insertion means that the protrusion is positioned to: (1) reduce the interaction between the leading edge of the coating and the solid or semisolid material, the sample, or a combination thereof; (2) reduce the friction between the coating and the solid or semisolid material, the sample, or a combination thereof; or (3) a combination thereof, during insertion. In some examples according to the present disclosure, an instrument that lacks a protrusion loses a portion of the extraction phase coating, while an otherwise identical instrument that includes a protrusion loses less of the extraction phase coating. For example, an instrument that lacks a protrusion may lose about 10%, about 20%, about 30%, about 40%, about 50%, about 60%, about 70%, about 80%, about 90% or 100% of the extraction phase coating that is inserted into the sample, while an otherwise identical instrument that includes a protrusion may lose less than about 10%, less than about 5%, or 0% of the extraction phase coating.

The protrusion defines a leading side and a trailing side of the insertion portion in reference to the direction of insertion. In the context of the present disclosure, the leading side refers to at least a portion of the side of the protrusion that is inserted into or through the solid or semisolid material before the trailing side of the protrusion.

In some examples according to the present disclosure, the protrusion is formed from the support structure. In other examples according to the present disclosure, the protrusion is affixed to the support structure. Similar to the support structure, the protrusion may be made of any material that can be inserted into or through the solid or semisolid material and into a sample without becoming impaired. The material of the protrusion may be chosen depending on: (1) the sample; (2) cost constraints; or (3) a combination thereof. In some examples according to the present disclosure, the protrusion is made of a suitable metal or metal alloy, for example when the solid or semisolid material, the sample, or a combination thereof has an increased rigidity or viscosity. Examples of suitable metal or metal alloy are steel, stainless steel, or nickel-titanium alloy. In some examples according to the present disclosure, the protrusion is a suitable polymer. Examples of a suitable polymer are polybutylene terephthalate, polyether ether ketone, or polyhexamethylene adipamide. In some examples according to the present disclosure, the protrusion is fused silica. In some examples according to the present disclosure, the protrusion is a suitable carbon lattice. Examples of a suitable carbon lattices are comprised of carbon fibers, or a carbon nanotube superstructures. In some examples according to the present disclosure, the at least one protrusion is made of wood.

The protrusion may be located on any side of the support structure provided that the protrusion has a height that is approximately equal to the thickness of the extraction phase where the extraction phase abuts the protrusion, and shields the extraction phase coating during insertion. The location of the protrusion on the support structure may be chosen depending on: (1) the sample; (2) the extraction parameters; (3) the depth of extraction; or (4) a combination thereof. In some examples according to the present disclosure, the support structure has one protrusion that is located less than 2.0 cm from the leading edge of the support structure along the axis of insertion. In some examples according to the present disclosure, the protrusion is located at a fixed distance from the leading edge of the support structure along the axis of insertion, for example when the sampling instrument is inserted into an animal until the leading edge of the support structure contacts an internal bone of the animal and the extraction phase coating is within the animal at a fixed distance from the bone.

The protrusion may extend at any angle from the axis of insertion of the support structure provided that the protrusion has a height that is approximately equal to the thickness of the extraction phase where the extraction phase abuts the protrusion, and shields the extraction phase coating during insertion. In some examples according to the present disclosure, the protrusion has an edge on the trailing side that is substantially perpendicular to the axis of insertion. In other examples according to the present disclosure, the protrusion has an edge on the trailing side that is at an angle of about 10°, about 20°, about 30°, about 40°, about 45°, about 50°, about 60°, about 70°, about 80°, about 90°, about 100°, about 110°, about 130°, about 140°, about 150°, about 160°, or about 170° from the axis of insertion of the support structure. In some examples according to the present disclosure, the trailing side edge of the protrusion is at an angle from about 60° to about 120° from the axis of insertion of the support structure, for example when: (1) increasing the shielding of the extraction phase coating; (2) reducing the jutting of the protrusion, that is the amount of the protrusion that extends past the thickness of the extraction phase coating, to decrease the exposure of the trailing edge of the protrusion to the sample during removal of the sampling instrument; or (3) a combination thereof, is desirable.

The protrusion may be any shape provided that the protrusion has a height that is approximately equal to the thickness of the extraction phase where the extraction phase abuts the protrusion, and shields the extraction phase coating during insertion. The shape of the protrusion may be chosen depending on: (1) the sample; (2) the extraction parameters; or (3) a combination thereof. In some examples according to the present disclosure, the protrusion has a rectangular-like shape, for example when increasing the surface area of the extraction phase coating is desirable. In other examples according to the present disclosure, the protrusion has a gradual slope-like shape or hill-like shape, for example when the solid or semisolid material, the sample, or a combination thereof has an increased rigidity or viscosity.

In some examples according to the present disclosure, the protrusion may form at least a portion of an end of the support structure, for example, the protrusion may form a portion of the needle point of a needle-shaped support structure.

In some examples according to the present disclosure, the protrusion extends around the circumference of the insertion portion of the support structure, for example when increasing the surface area of the extraction phase coating is desirable. In some examples according to the present disclosure, the protrusion extends at least about 5%, at least about 10%, at least about 25%, at least about 50%, at least about 75%, at least about 90%, at least about 95%, or 100% around the circumference of the insertion portion of the support structure.

The protrusion may be any size provided that the protrusion has a height that is approximately equal to the thickness of the extraction phase where the extraction phase abuts the protrusion, and shields the extraction phase coating during insertion. In some examples according to the present disclosure, the protrusion extends most of the length along the axis of insertion of the insertion portion of the support structure, for example when: (1) the solid or semisolid material, the sample, or a combination thereof has an increased rigidity or viscosity and the protrusion requires increased stability; (2) reducing the friction between the solid or semisolid material, the sample, or a combination thereof with the extraction phase is desirable; or (3) a combination thereof.

In other examples according to the present disclosure, the protrusion extends less than about 90%, less than about 75%, less than about 50%, less than about 25%, less than about 10%, or less than about 5% of the length along the axis of insertion of the insertion portion of the support structure. In some examples according to the present disclosure, the protrusion is less expansive along the axis of insertion of the insertion portion, for example when increasing the surface area of the extraction phase coating is desirable.

The protrusion projecting from the support structure refers to the protrusion projecting from the axis of insertion of the support structure. The protrusion may have any height provided that the height is approximately equal to the thickness of the extraction phase where the extraction phase abuts the protrusion, and the height is sufficient to shield the extraction phase coating during insertion. The chosen height of the protrusion may depend on: (1) the thickness of the extraction phase coating; (2) the sample; (3) the extraction parameters; (4) the size of the support structure; or (5) a combination thereof. In some examples according to the present disclosure, the height of the protrusion is from about 1 µm to about 1 cm, for example, 1 µm, 2 µm, 3 µm, 4 µm, 5 µm, 6 µm, 7 µm, 8 µm, 9 µm, 10 µm, 25 µm, 50 µm, 75 µm, 100 µm, 125 µm, 150 µm, 175 µm, 200 µm, 500 µm, 1000 µm, 0.25 cm, 0.50 cm, 0.75 cm, 1.0 cm; or the height is from any one of the heights listed above and any other of the heights listed above. In some examples according to the present disclosure, the height of the protrusion is from about 90% to about 110% as high as the thickness of the extraction phase coating that abuts the protrusion. In some examples according to the present disclosure, the height of the protrusion is about 100% as high as the thickness of the extraction phase coating that abuts the protrusion.

The support structure may comprise a plurality of protrusions. The number of protrusions chosen may depend on: (1) the sample; (2) the extraction parameters; or (3) a combination thereof. In some examples according to the present disclosure, the sampling instrument comprises a plurality of protrusions, for example when: (1) the solid or semisolid material, the sample, or a combination thereof has an increased rigidity or viscosity and increasing the strength of the support structure is desirable; (2) improving the shielding of the extraction phase coating during insertion is desirable; (3) improving the shielding of the extraction phase coating during withdrawal of the sampling instrument is desirable; (4) reducing the interaction between the solid or semisolid material, the sample, or a combination thereof and the extraction phase is desirable; (5) reducing the friction between the solid or semisolid material, the sample, or a combination thereof and the extraction phase is desirable; (6) reducing the interaction between the trailing edge of the insertion portion with the solid or semisolid material, the sample, or a combination thereof, during withdrawal of the sampling instrument is desirable; (7) reducing the friction between the trailing edge of the insertion portion with the solid or semisolid material, the sample, or a combination thereof, during withdrawal of the sampling instrument is desirable; (8) resolving the spatial resolution of analyte concentration gradients corresponding to depth in the sample is desirable and the plurality of protrusions function as barriers to diffusion; or (9) a combination thereof.

The plurality of protrusions may be located on any side of the support structure provided that at least one of the plurality of protrusions has a height that is approximately equal to the thickness of the extraction phase where the extraction phase abuts the protrusion and shields the extraction phase coating during insertion. In some examples according to the present disclosure, the plurality of protrusions shield the extraction phase coating during withdrawal of the sampling instrument. In some examples according to the present disclosure, the support structure comprises adjacent pairs of protrusions, and the extraction phase coating is located between every adjacent pair of protrusions, for example when increasing the surface area of the extraction phase coating is desirable.

In the context of the present disclosure, the: (1) angle; (2) size; and (3) shape of each one of the plurality of protrusions may be chosen independently, as described above, provided that at least one of the plurality of protrusions has a height that is approximately equal to the thickness of the extraction phase where the extraction phase abuts the protrusion and shield the extraction phase coating during insertion, during withdrawal, or a combination thereof.

The distance between adjacent pairs of protrusions may be chosen depending on: (1) the sample; (2) the extraction parameters; or (3) a combination thereof. In some examples according to the present disclosure, the distance between adjacent pairs of protrusions is from about 0.01 mm to about 2.0 cm, for example, 0.01 mm, 0.05 mm, 0.1 mm, 0.25 mm, 0.50 mm, 0.75 mm, 0.1 cm, 0.2 cm, 0.5 cm, 0.75 cm, 1.0 cm, 1.5 cm, 2.0 cm; or the distance is from any one of the distances listed above and any other of the distances listed above. In some examples according to the present disclosure, the distance between adjacent pairs of protrusions is increased, for example when increasing the area of the extraction phase is desirable. In other examples according to the present disclosure, the distance between adjacent pairs of protrusions is decreased, for example when: (1) increasing the resolution of the extraction process; (2) increasing the robustness of the sampling instrument; (3) increasing the shielding of the extraction phase coating during insertion, during withdrawal of the sampling instrument, or a combination thereof; (4) reducing the interaction between the solid or semisolid material, the sample, or a combination thereof and the extraction phase; (5) reducing the friction between the solid or semisolid material, the sample, or a combination thereof and the extraction phase; (6) reducing the interaction between the trailing edge of the insertion portion with the solid or semisolid material, the sample, or a combination thereof, during withdrawal of the sampling instrument; (7) reducing the friction between the trailing edge of the insertion portion with the solid or semisolid material, the sample, or a combination thereof, during withdrawal of the sampling instrument; or (8) a combination thereof, is desirable. It should be understood that the distances between multiple adjacent pairs of protrusions may be chosen independently.

The position of each one of the plurality of protrusions may be chosen independently provided that the extraction phase coating is shielded during insertion. In some examples according to the present disclosure, each one of the plurality of protrusions is in substantial alignment along the axis of insertion of the support structure. In some examples according to the present disclosure, each one of the plurality of protrusions is located on the same side of the support structure and in substantial alignment along the axis of insertion of the support structure. In other examples according to the present disclosure, each one of the plurality of protrusions is located on the same side of the support structure and are laterally offset along the axis of insertion of the support structure.

In some examples according to the present disclosure, the support structure comprises one protrusion that extends around the circumference of the support structure in a screw-like or bolt-like configuration, for example when providing mechanical support to the sample body such as a multi-pin sampler body, is desirable. In some examples of the screw-like or bolt-like configurations, the adjacent pairs of threads of the screw-like or bolt-like protrusion are separated by a distance from about 0.01 mm to about 2.0 mm, for example, 0.01 mm, 0.02 mm, 0.05 mm, 0.07 mm, 0.1 mm, 0.5 mm, 1.0 mm, 1.5 mm, 2.0 mm; or the distances is from any one of the distances listed above and any other of the distances listed above. In some examples of the screw-like or bolt-like configuration, the extraction phase is located between every adjacent pair of threads.

The support structure may comprise additional protrusions that do not form part of the insertion portion. In some examples according to the present disclosure, one of the plurality of protrusions may be the barrier between the insertion portion and the non-insertion portion of the support structure.

The support structure may be configured to control the depth of insertion of the sampling instrument into a sample. The configuration may be in the same form of the support structure or may be an attachable backing to the support structure that may be adjustable to vary the depth of insertion. In some examples according to the present disclosure, the configuration is an abutment or a flange that extends substantially perpendicular from the axis of insertion from the non-insertion portion of the support structure with a cross-sectional plane that is larger than the largest cross-sectional plane of the insertion portion of the support structure, and can physically restrict continued insertion of the sampling instrument into a sample. In some examples according to the present disclosure, the abutment or flange may be adjustable. As described above, in some examples according to the present disclosure, the support structure is coupleable to a spring loaded propelling device that is configured to control the depth of insertion of the sampling instrument into the sample by, for example, providing a fixed and adjustable force to the sampling instrument.

The support structure may be configured to comprise a handle to help a user manipulate the sampling instrument. The handle may be in the same form of the support structure or may be attachable to the support structure.

The support structure may be attachable to a retrieval mechanism to allow the removal of the support structure from the sample. In some examples according to the present disclosure, the retrieval mechanism is a string.

The support structure may comprise a tracking device, beacon, or microchip for monitoring the location of the sampling instrument in the sample, for example in situations of long-term sampling of a live animal, where the animal is released after insertion of a sampling instrument according to the present disclosure and then located at a later time to retrieve the sampling instrument.

The extraction phase is any material that sorbs the component of interest and can be coated onto at least a portion of the support structure. In some examples according to the present disclosure, the extraction phase comprises a sorptive polymer or a combination of a polymer and a sorptive material immobilized in the polymer. The sorptive polymer may comprise an organic polymer, for example, poly divinyl benzene (DVD), polydimethysiloxane (PDMS), hydrophilic lipophilic balanced (HLB), or polyethylene glycol (PEG). The sorptive material may comprise particles, polymers, nanosheets, nanotubes, or any combination thereof. The sorptive material may be amorphous. The sorptive material may be inorganic, organic, or an inorganic/organic hybrid. In some examples according to the present disclosure, the adsorptive material may comprises: normal-phase silica particles, C-1/silica particles, C-4/silica particles, C-6/silica particles, C-8/silica particles, C-18/silica particles, C-30/silica particles, reverse-phase amide silica particles, HS-F5/silica particles, phenyl/silica particles, cyano/silica particles, diol/silica particles, ionic liquid/silica particles, molecular imprinted polymer particles, hydrophilic-lipophilic-balanced (HLB) particles, carboxen 1006 particles, carbowax particles, divinylbenzene (DVB) particles, octadecylsilane particles, nanoparticles, processed mineral based particles, carbon nanotubes, functionalized-carbon nanotubes, graphene, graphene oxide, functionalized-graphene, quantum dots, or any combination thereof. In some examples according to the present disclosure, the polymer may comprise substituted or unsubstituted poly (dimethylsiloxane), polyacrylate, poly(ethylene glycol), poly(divinylbenzene), polypyrrole, or derivatised cellulose. In some examples according to the present disclosure, the extraction phase is HLB, for example when an affinity towards components of interest with a broad range of physical chemical properties, is desirable.

The support structure being at least partially coated refers to a surface area of the insertion portion of the support structure coated with an extraction phase that is sufficiently large to sorb the component of interest. The surface area of the insertion portion of the support structure may be 100%, at least about 95%, at least about 90%, at least about 85%, at least about 80%, at least about 75%, at least about 50%, at least about 25%, at least about 10%, or at least about 5% coated with an extraction phase. In some examples according to the present disclosure, at least about 80% of the surface area of the insertion portion is coated with an extraction phase, for example when increasing the extraction phase volume and sensitivity of the extraction process is desirable. In some examples according to the present disclosure, the extraction phase coating covers a high percentage of the surface area of the insertion portion of the support structure, for example when increasing the surface area of the extraction phase coating for: (1) increasing the speed of the extraction; (2) increasing the sensitivity of the extraction process; or (3) a combination thereof, is desirable.

The extraction phase coating may be at any location of the insertion portion of the support structure provided that: (1) at least some of the extraction phase coating, that is a sufficient amount to sorb the component of interest, is shielded by the protrusion during insertion; and (2) at least some of the extraction phase coating abuts the trailing side edge of the protrusion. As described above, the extraction phase coating may be located between every adjacent pair of protrusions.

The thickness of the extraction phase coating refers to the height of the extraction phase from the surface of the support structure. Any thickness of the extraction phase coating may be chosen, provided that: (1) the thickness is sufficient to sorb a sufficient amount of the component of interest to be detected; and (2) the thickness is approximately equal to the height of the protrusion where the extraction phase abuts the trailing side edge of the protrusion. The thickness of the extraction phase coating may be chosen depending on: (1) the type of extraction phase; (2) the extraction parameters; (3) the height of the protrusion; or (4) a combination thereof. In some examples according to the present disclosure, the thickness of the extraction phase coating is from about 1 µm to about 1 cm, for example, 1 µm, 2 µm, 3 µm, 4 µm, 5 µm, 6 µm, 7 µm, 8 µm, 9 µm, 10 µm, 25 µm, 50 µm, 75 µm, 100 µm, 125 µm, 150 µm, 175 µm, 200 µm, 500 µm, 1000 µm, 0.25 cm, 0.50 cm, 0.75 cm, 1.0 cm; or the thickness is from any one of the thicknesses listed above and any other of the thicknesses listed above. In some examples according to the present disclosure, the thickness of the extraction phase coating is from about 1 µm to about 50 µm. In some examples according to the present disclosure, the extraction phase coating is thinner, for example when: (1) decreasing the time for reaching equilibrium with the component of interest in the sample; (2) increasing the reproducibility of the extraction process; (3) using a smaller sampling instrument for the extraction; or (4) a combination thereof, is desirable. In some examples according to the present disclosure, the extraction phase coating is thicker, for example when: (1) longer extraction times; (2) increased sensitivity of the extraction process; or (3) a combination thereof, is desirable.

The type, thickness, and the area of the insertion portion of the support structure coated with the extraction phase, may be independently chosen and varied on the same support structure. In some examples when the support structure comprises a plurality of protrusions, the extraction coating located between every adjacent pair of protrusions differs, for example when the extraction of different components of interest located at different depths in the sample is desirable. The type, thickness, and the area of the insertion portion of the support structure coated with the extraction phase may be varied to decrease the overall time period for extracting the component of interest, for example, increasing the surface area of the extraction phase coating and decreasing its thickness may decrease the time for extraction.

The speed at which the sampling instrument is inserted into or through the solid or semisolid material and into the sample may be chosen depending on: (1) the type of solid or semisolid material; (2) the type of sample; (3) the extraction parameters; or (4) a combination thereof. In some examples according to the present disclosure, the speed of insertion is from about 1 mm/s to about 90 m/s, for example 1 mm/s, 5 mm/s, 10 mm/s, 50 mm/s, 100 mm/s, 500 mm/s, 1 m/s, 5 m/s, 10 m/s, 15 m/s, 30 m/s, 45 m/s, 60 m/s, 75 m/s, 90 m/s; or the speed is from any one of the speeds listed above and any other of the speeds listed above. In some examples according to the present disclosure, the speed of insertion is lower, for example when: (1) the solid or semisolid material, the sample, or a combination thereof has an increased rigidity or viscosity; (2) increased precision is desirable; or (3) a combination thereof. In some examples according to the present disclosure, the speed of insertion is lower, for example when the sample is delicate, for example brain tissue, and reducing damage to the sample is desirable. In other examples according to the present disclosure, the speed of insertion is higher, for example when the sample is live and robust, for example a fish, and rapid sampling to reduce the time of interaction with the sample is desirable.

The amount of time that the extraction phase coating is allowed to sorb the component of interest may be chosen depending on: (1) the component of interest; (2) the type of sample; (3) the extraction parameters; or (4) a combination thereof. In some examples according to the present disclosure, the amount of time that the extraction phase coating is allowed to sorb the component of interest is from about 1 minute to about 72 hours minutes, for example, 1 min, 2 min, 5 min, 10 min, 15 min, 30 min, 45 min, 60 min, 6 hours, 12 hours, 18 hours, 24 hours, 30 hours, 36 hours, 42 hours, 48 hours, 54 hours, 60 hours, 66 hours, 72 hours; or the amount of time is from any one of the times listed above and any other of the times listed above. In some examples according to the present disclosure, the amount of time that the extraction phase coating is allowed to sorb the component of interest is the amount of time that allows the sorption of a detectable amount of the component of interest. In some examples according to the present disclosure, the amount of time that the extraction phase coating is allowed to sorb the component of interest is equivalent to the extraction phase coating reaching equilibrium with the component of interest in the sample, for example when determining the amount of the component of interest in the sample is desirable. In some examples according to the present disclosure, the amount of time that the extraction phase coating is allowed to sorb the component of interest is less than the amount of time required for the extraction phase coating to reach equilibrium with the component of interest in the sample, for example when: (1) determining the presence of the component of interest in the sample; (2) decreasing the overall time period of the extraction process; or (3) a combination thereof, is desirable.

The speed at which the sampling instrument is withdrawn from the sample may be chosen depending on: (1) the type of solid or semisolid material; (2) the type of sample; (3) the extraction parameters; or (4) a combination thereof. In some examples according to the present disclosure, the speed of withdrawal is from about 1 mm/s to about 10 m/s, for example 1 mm/s, 5 mm/s, 10 mm/s, 50 mm/s, 100 mm/s, 500 mm/s, 1 m/s, 5 m/s, 10 m/s; or the speed is from any one of the speeds listed above and any other of the speeds listed above. In some examples according to the present disclosure, the speed of withdrawal is lower, for example when: (1) the solid or semisolid material, the sample, or a combination thereof has an increased rigidity or viscosity; (2) the solid or semisolid material, the sample, or a combination thereof has a decreased durability; (3) increased precision is desirable; or (4) a combination thereof. In other examples according to the present disclosure, the speed of withdrawal is higher, for example when the sample is live and robust, for example a fish, and rapid sampling to reduce the time of interaction with the sample is desirable.

The sampling instrument may comprise an additional coating, also referred to as an over-coating, for example when: (1) decreasing the adherence of contaminants in the the solid or semisolid material, the sample, or a combination thereof to the sampling instrument; (2) improving biocompatibility; (3) increasing the shielding of the extraction phase coating from friction with the solid or semisolid material, the tissue sample, or a combination thereof during insertion; (4) decreasing agitation or damage of the sample during insertion; (5) reducing the interaction between the trailing edge of the insertion portion with the solid or semisolid material, the sample, or a combination thereof, during withdrawal of the sampling instrument; (6) reducing the friction between the trailing edge of the insertion portion with the solid or semisolid material, the sample, or a combination thereof, during withdrawal; or (7) a combination thereof, is desirable. Decreasing the adherence of contaminants in the sample to the sampling instrument may be desirable to increase the number of samplings that can be performed from one or multiple sites on the sample. Improved biocompatibility may be desirable to extend either the time period the extraction phase coating can be in contact with the sample, or increase the number of samplings that can be made from one site of the sample. Increasing the shielding of the extraction phase coating may be desirable to increase the number of samplings that can be made from one or multiple sites of the sample. In some examples according to the present disclosure, the additional coating provides a smoother outer surface compared to the outer surface of the sampling instrument, and that physically interacts with the solid or semisolid material, the tissue sample, or a combination thereof, which may decrease the agitation or damage of the solid or semisolid material, the tissue sample, or a combination thereof during insertion.

The additional coating may cover any area of the sampling instrument provided that the extraction phase coating is able to sorb the component of interest. In some examples according to the present disclosure, the components of interest diffuse through the additional coating prior to being sorbed by the extraction phase coating. In some examples according to the present disclosure, the additional coating covers at least the extraction phase coating. In some examples according to the present disclosure, the additional coating covers at least about 5%, at least about 10%, at least about 25%, at least about 50%, at least about 75%, at least about 90%, at least about 95%, or 100% of the surface area of the sampling instrument.

The additional coating may be any material that can be coated onto at least the extraction phase coating and allow the extraction phase coating to sorb the component of interest. In some examples according to the present disclosure, the additional coating comprises an organic polymer. In some examples according to the present disclosure, the additional coating is a biocompatible polymeric coating. The biocompatible polymeric coating may comprise polyacrylonitrile, polyacrylate, Polytetrafluoroethylene, polydimethylsiloxane, polyethylene glycol, or a combination thereof.

The additional coating may be applied to the sampling instrument by: (1) dipping the sampling instrument into an excess of additional coating; (2) spray coating the sampling instrument with the additional coating; or (3) electrospinning.

The additional coating may be any thickness provided that the extraction phase coating is able to sorb a component of interest. In some examples according to the present disclosure, the thickness of the additional coating is from about 1.0 µm to about 100.0 µm, for example, 1.0 µm, 2.0 µm, 3.0 µm, 5.0 µm, 10.0 µm, 20.0 µm, 30.0 µm, 40.0 µm, 50.0 µm, 60.0 µm, 70.0 µm, 80.0 µm, 90.0 µm, 100.0 µm; or the thickness is from any one of the thicknesses listed above and any other of the thicknesses listed above. In some examples according to the present disclosure, the thickness of the additional coating is lower, for example when increasing the diffusion of the component of interest through the additional coating and increasing the sensitivity of the extraction process is desirable.

The component of interest may be any detectable component. In some examples according to the present disclosure, the component of interest is a bacteria, a virus, a sub-cellular component, a biopolymer, DNA, a protein, a drug, a drug metabolite, a hormone, a vitamin, an environmental contaminant, a chemical, a cell, or a combination thereof.

Figure 1B:
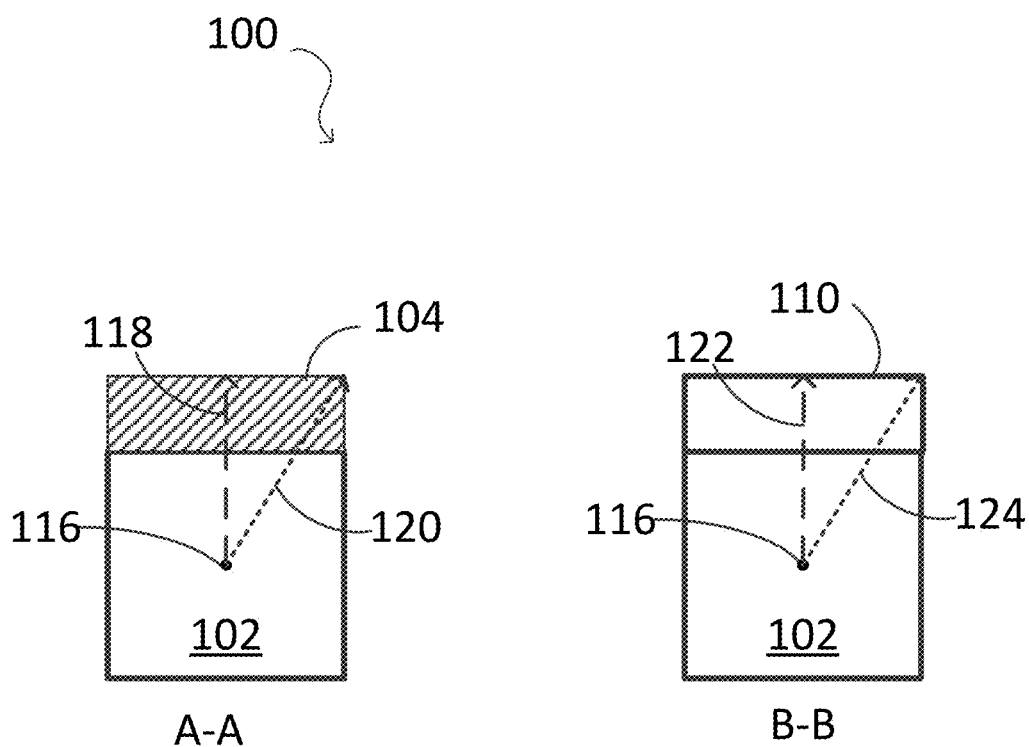

A solid phase microextraction sampling instrument is any instrument that can sorb a component of interest from a sample. The sampling instrument illustrated in FIGS. 1A-B is one example of a sampling instrument according to the present disclosure. The sampling instrument (100) has a support structure (102) at least partially coated with an extraction phase (104) for extracting a component of interest. The support structure (102) has an insertion portion (106) for inserting into or through the solid or semisolid material and into the sample, and a non-insertion portion (108). The insertion portion has one protrusion (110) defining a leading side (112) and a trailing side (114), where the coating (104) is located at least on the trailing side (114) of the protrusion (110). The coating (104) abuts the trailing side edge of the protrusion, and the protrusion (110) projects at least as high from the support structure (102) as the thickness of the coating (104) where the coating abuts the protrusion. The protrusion (110) shields the coating during insertion in the direction of the axis of insertion (116) of the support structure. The cross-sectional plane A-A shows the instrument as having a cross section that is about the same size as the cross-section of B-B. The distances of the vectors 118 and 120 in cross-section A-A are about equal to the distances of the vectors 122 and 123 in cross-section B-B, respectively. The dashed arrow indicates the direction of insertion.

Figure 2:
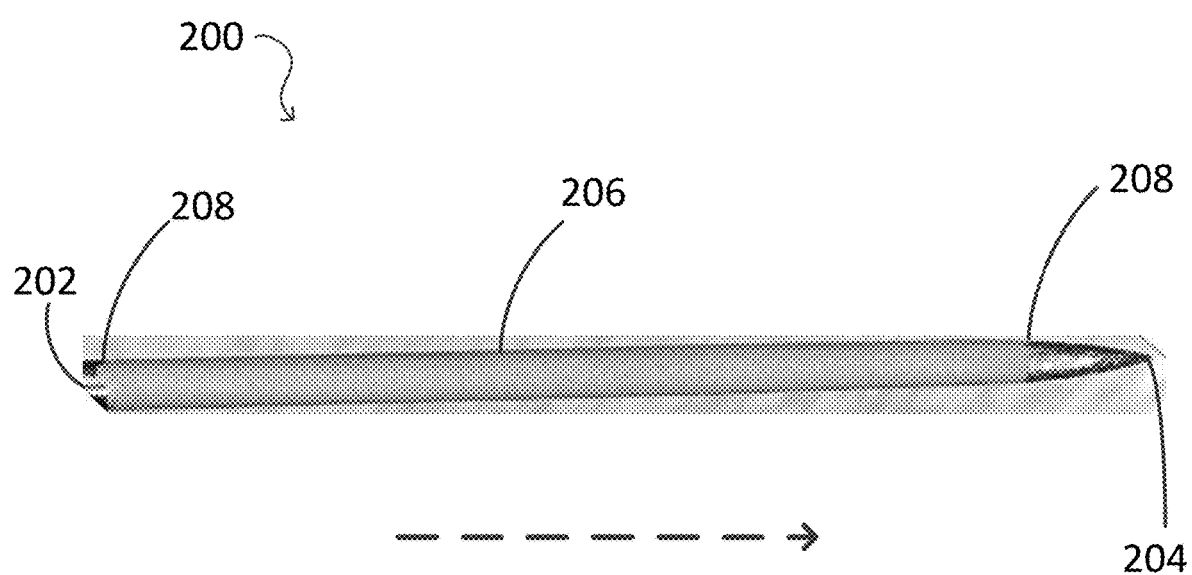
FIG. 2 is an image of an example of a sampling instrument according to the present disclosure.
Figure 3:
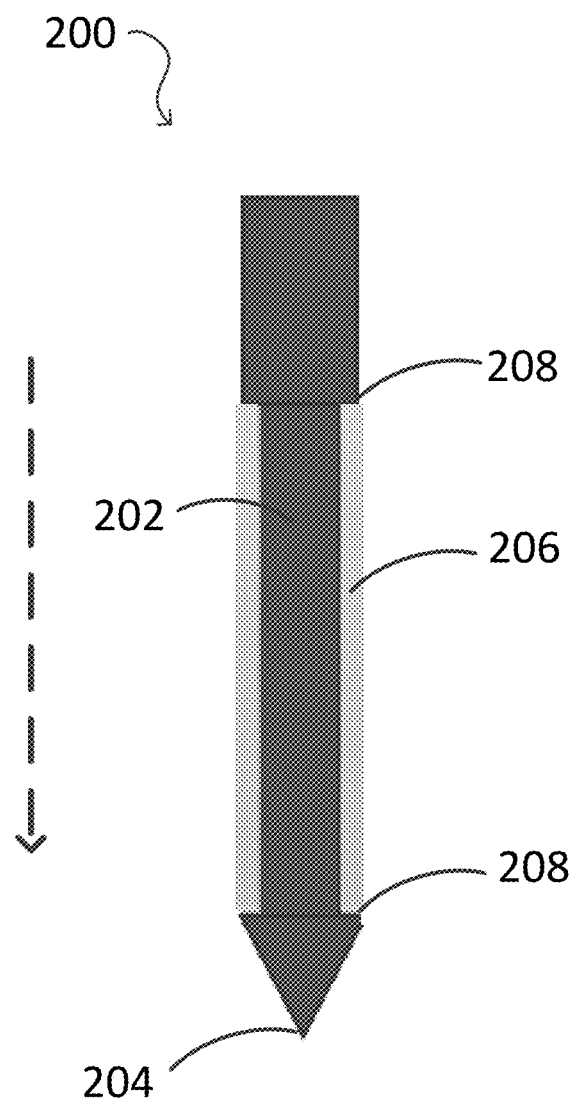
FIG. 3 is a schematic of an example of a sampling instrument according to the present disclosure.

FIG. 2 is an image of another embodiment according to the present disclosure. The sampling instrument (200) has a support structure (202) having a needle-like shape that has a needle point (204), the support structure is at least partially coated with an extraction phase (206) for extracting a component of interest, the support structure (202) has two protrusions (208) that extend around the circumference of the insertion portion of the support structure (202) and project at least as high from the support structure (202) as the thickness of the coating (204) where the coating abuts the protrusions to shield the coating during insertion. The dashed arrow indicates the direction of insertion. The support structure has a diameter of about 0.7 mm, the extraction phase coating has a thickness of about 10 µm, and the height of the protrusions is about 4 µm. FIG. 3 is an illustration of the cross-sectional plane along the axis of insertion of the sampling instrument shown in FIG. 2.

In some examples according to the present disclosure, the support structure comprises two protrusions, and the extraction phase coating is located between the two protrusions (see FIGS. 2 and 3).

Figure 4A:
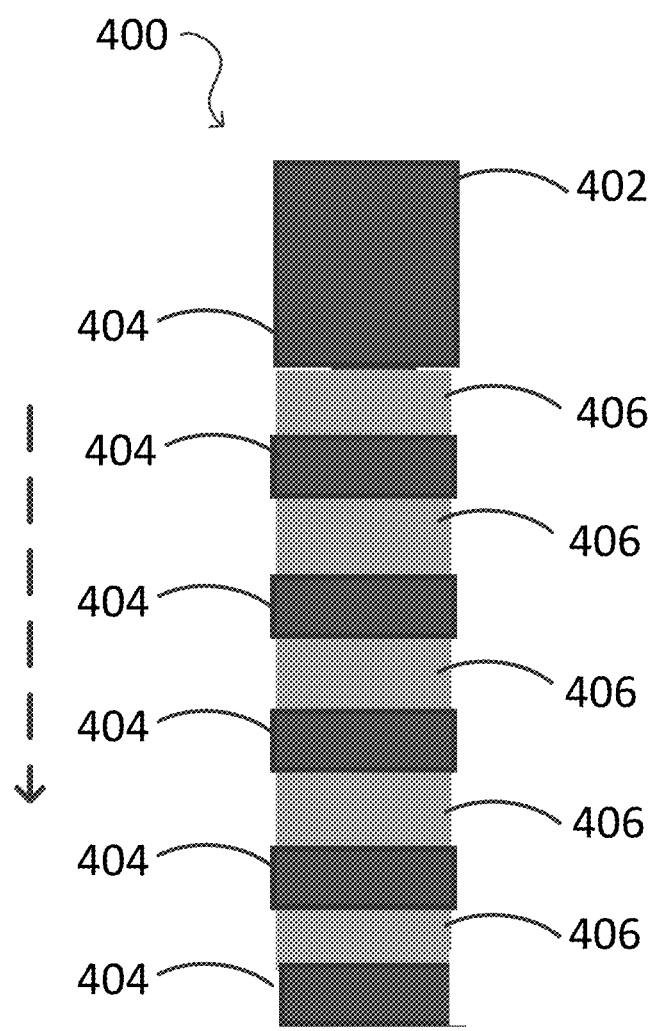
FIGS. 4A-B are schematics of an example of a sampling instrument according to the present disclosure.
Figure 4B:
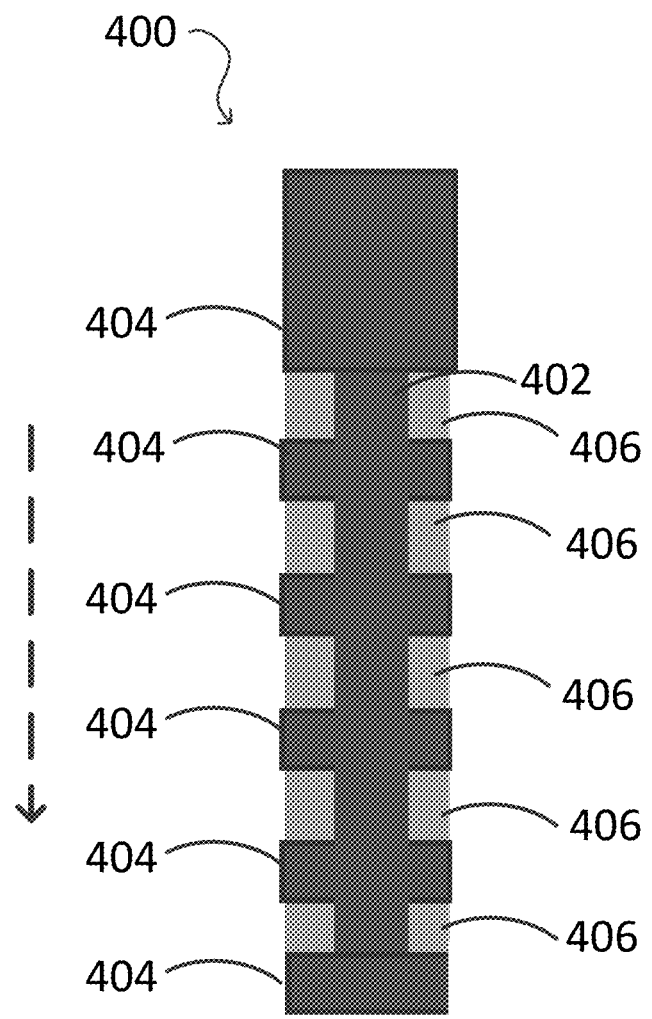

FIGS. 4A-B illustrate one example of a sampling instrument according to the present disclosure that comprises a plurality of protrusions in side view (FIG. 4A) and cross sectional view along the axis of insertion (FIG. 4B). The sampling instrument (400) has a support structure (402) of a cylindrical-like shape, the support structure has six protrusions (404) and is coated with an extraction phase (406) between every adjacent pair of protrusions (404). The dashed arrow indicates the direction of insertion.

Figure 5A:
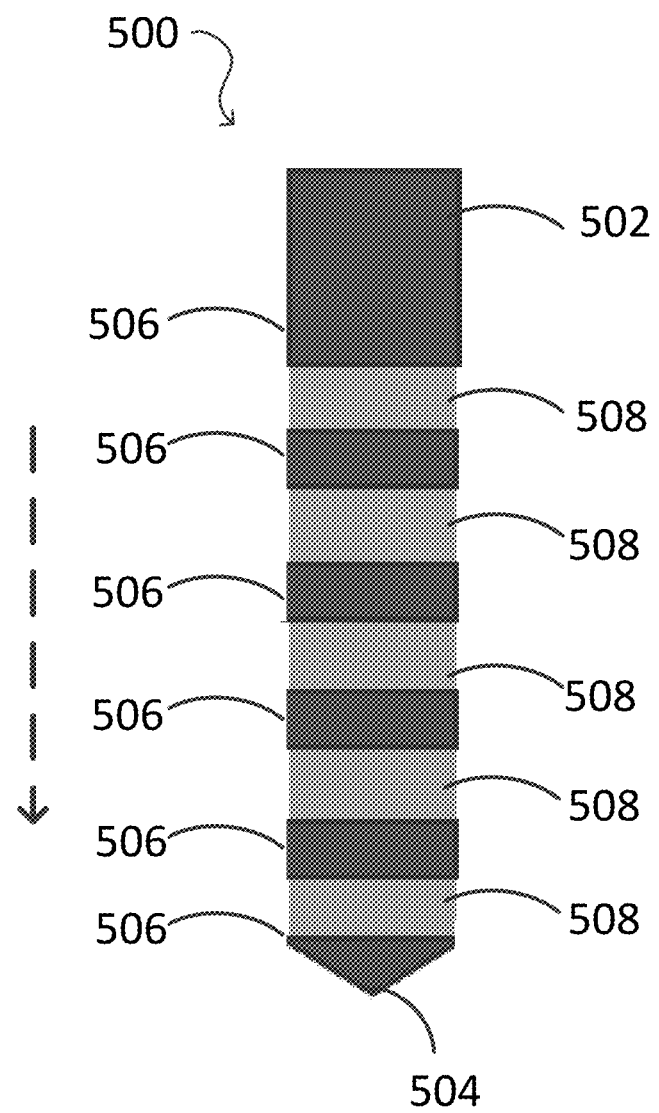
FIGS. 5A-B are schematics of an example of a sampling instrument according to the present disclosure.
Figure 5B:
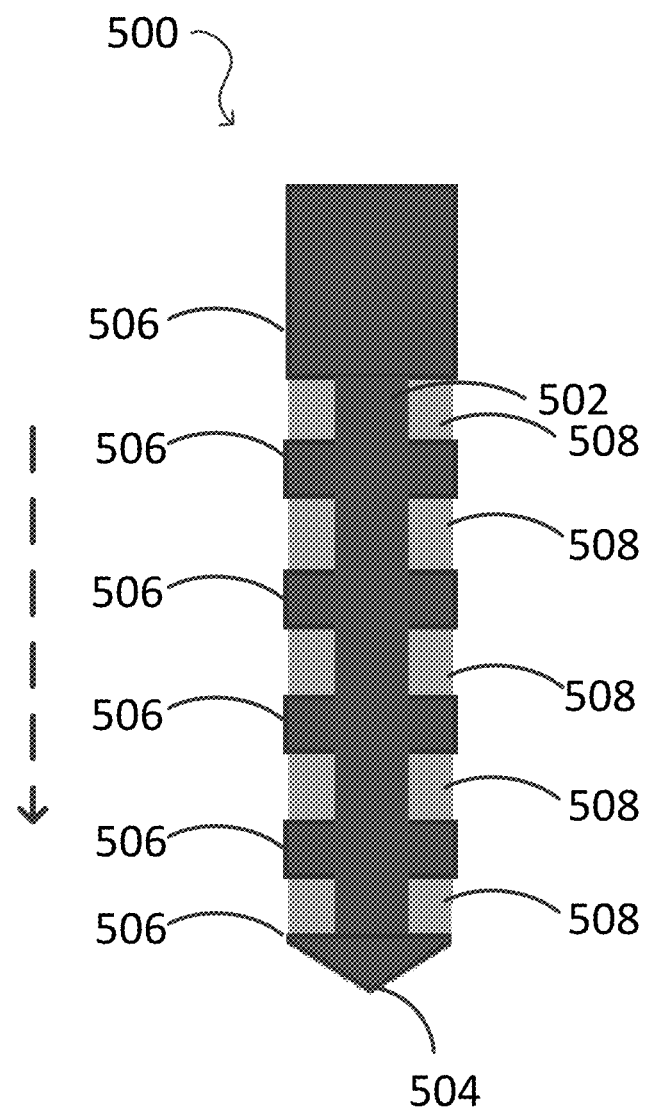

FIGS. 5A-B illustrate one example of a sampling instrument according to the present disclosure that comprises a plurality of protrusions in side view (FIG. 5A) and cross sectional view along the axis of insertion (FIG. 5B). The sampling instrument (500) has a support structure (502) of a needle-like shape having a needle point end (504). The support structure (502) has six protrusions (506) and is coated with an extraction phase (508) between every adjacent pair of protrusions (506). The protrusion closest to the insertion end of the support structure (502) abuts a portion of the needle point end (504). The dashed arrow indicates the direction of insertion.

Figure 6A:
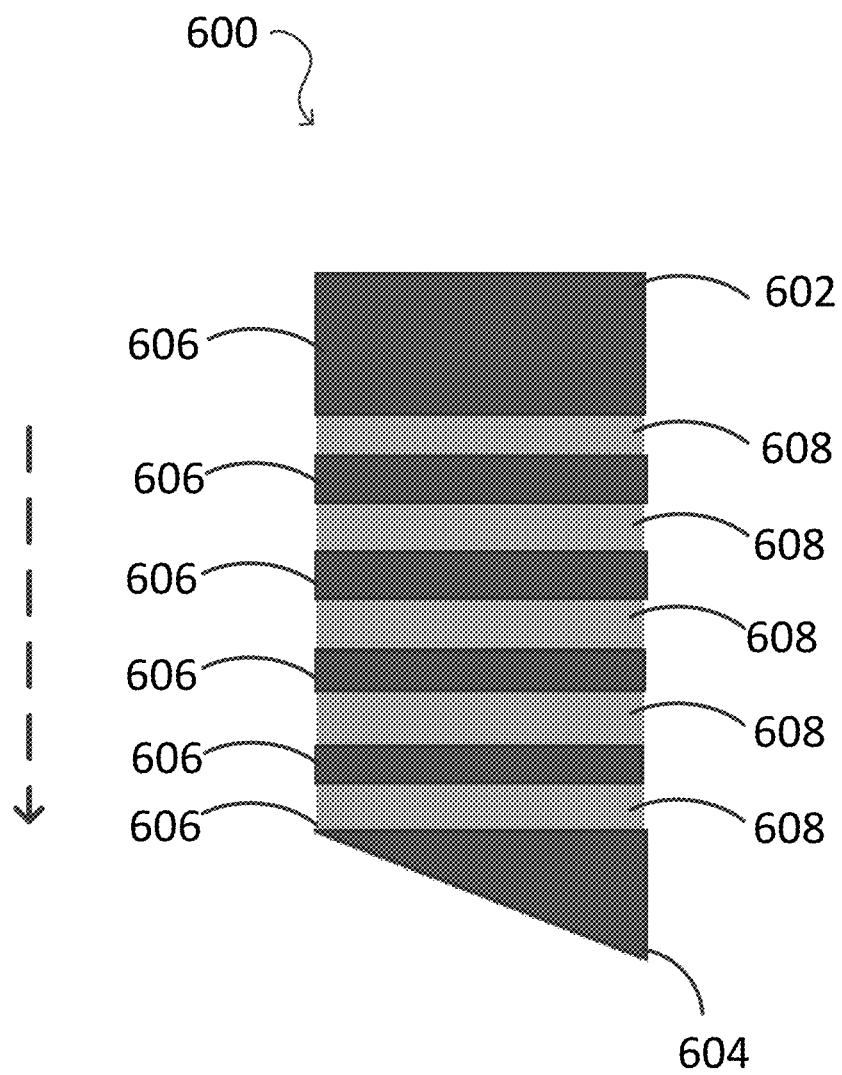
FIGS. 6A-B are schematics of an example of a sampling instrument according to the present disclosure.
Figure 6B:
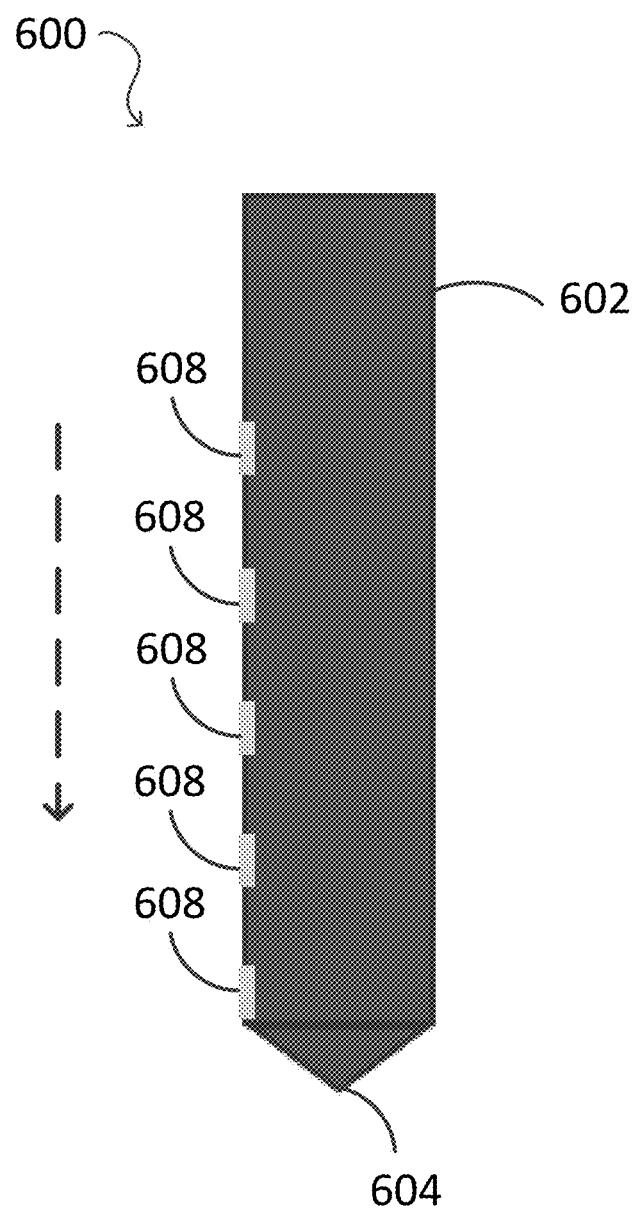

FIGS. 6A-B illustrate one example of a sampling instrument according to the present disclosure that comprises a plurality of protrusions in side view (FIG. 6A) and an adjacent side view (FIG. 6B). The sampling instrument (600) has a support structure (602) of a blade-like shape having a blade-like end (604). The support structure (602) has six protrusions (606) and is coated with extraction phase between every adjacent pair of protrusions. The protrusion closest to the insertion end of the support structure is a portion of the blade-like end (604). The dashed arrow indicates the direction of insertion.

Figure 7:
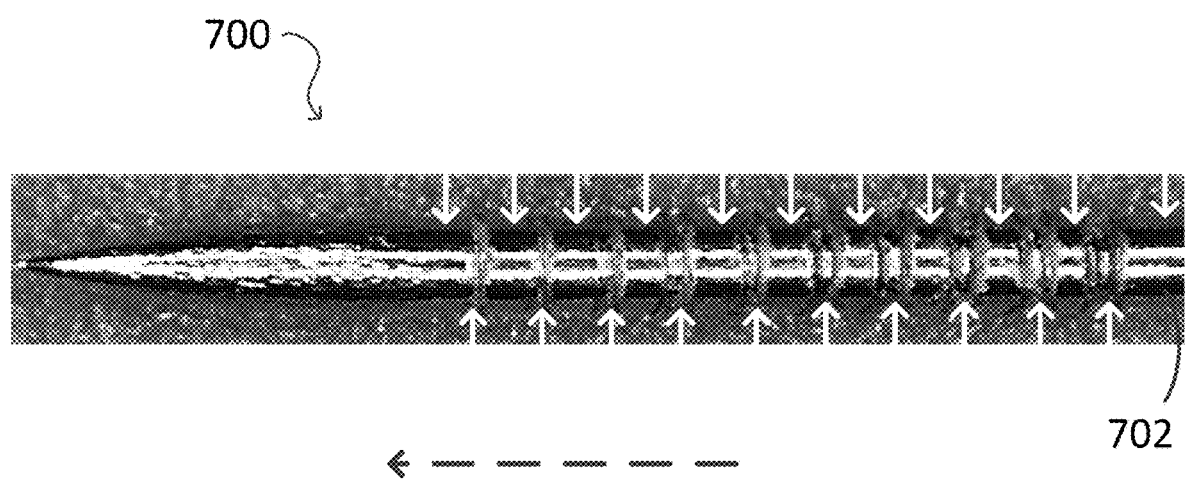
FIG. 7 is an image of an example of a sampling instrument with multiple protrusions according to the present disclosure.

FIG. 7 is an image of one example of a sampling instrument according to the present disclosure that has a plurality of protrusions. The sampling instrument (700) has a support structure (702) of a needle-like shape. The support structure (702) has 11 protrusions (arrows above the image) that extend around the circumference of the insertion portion of the support structure (702), and is coated with an extraction phase (arrows below the image) between every adjacent pair of protrusions (704). The distance between the adjacent pairs of protrusions is varied. The dashed arrow indicates the direction of insertion.

Figure 8:
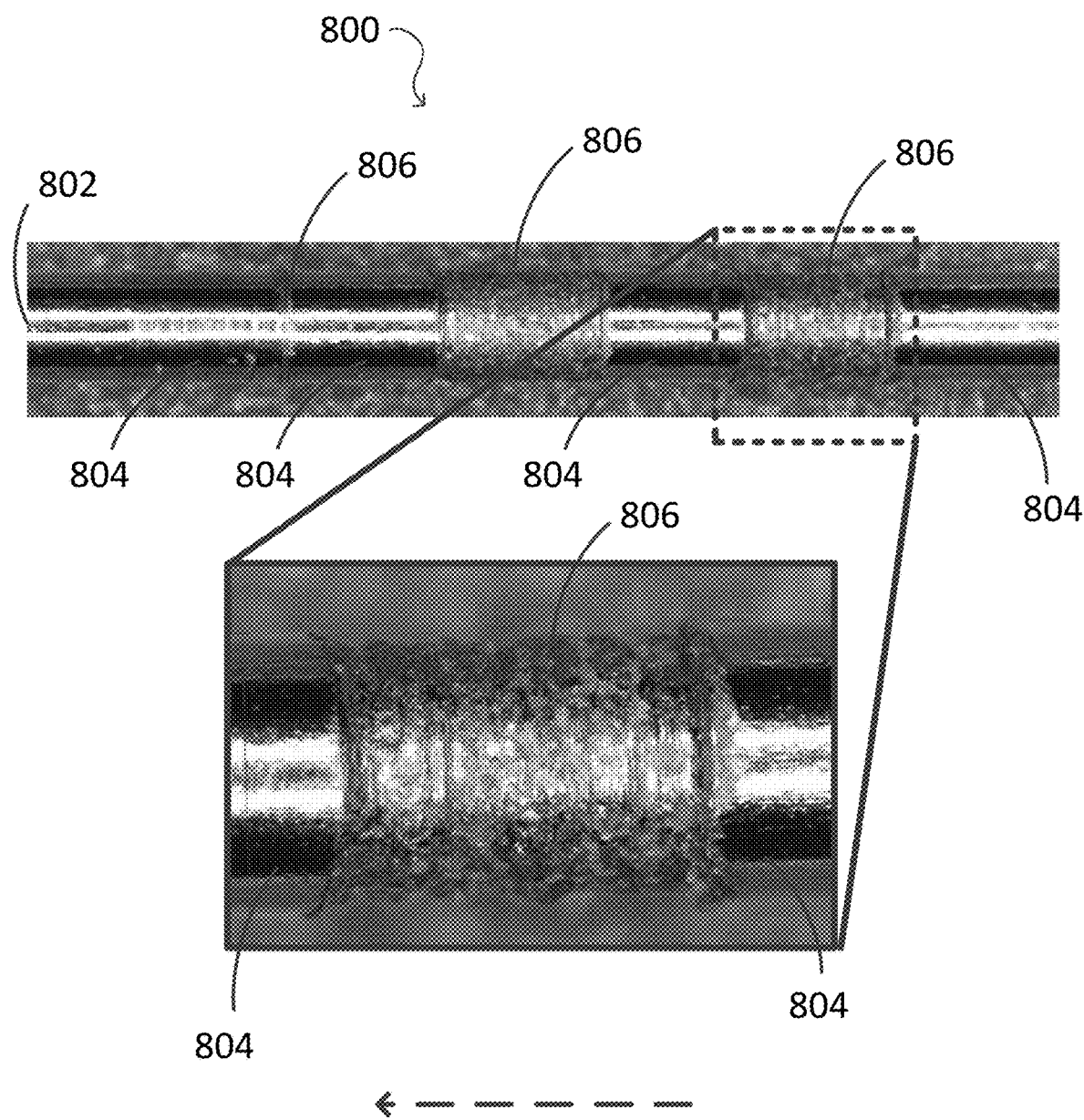
FIG. 8 is an image of an example of a sampling instrument with multiple protrusions according to the present disclosure. A section of the image has been magnified.

FIG. 8 is an image of one example of a sampling instrument according to the present disclosure that has a plurality of protrusions. The sampling instrument (800) has a support structure (802) of a cylindrical-like shape. The support structure (802) has 4 protrusions (804) that extend around the circumference of the insertion portion of the support structure (802), and is coated with an extraction phase (806) between every adjacent pair of protrusions (804). The distance between the adjacent pairs of protrusions is varied. The dashed arrow indicates the direction of insertion.

Figure 9:
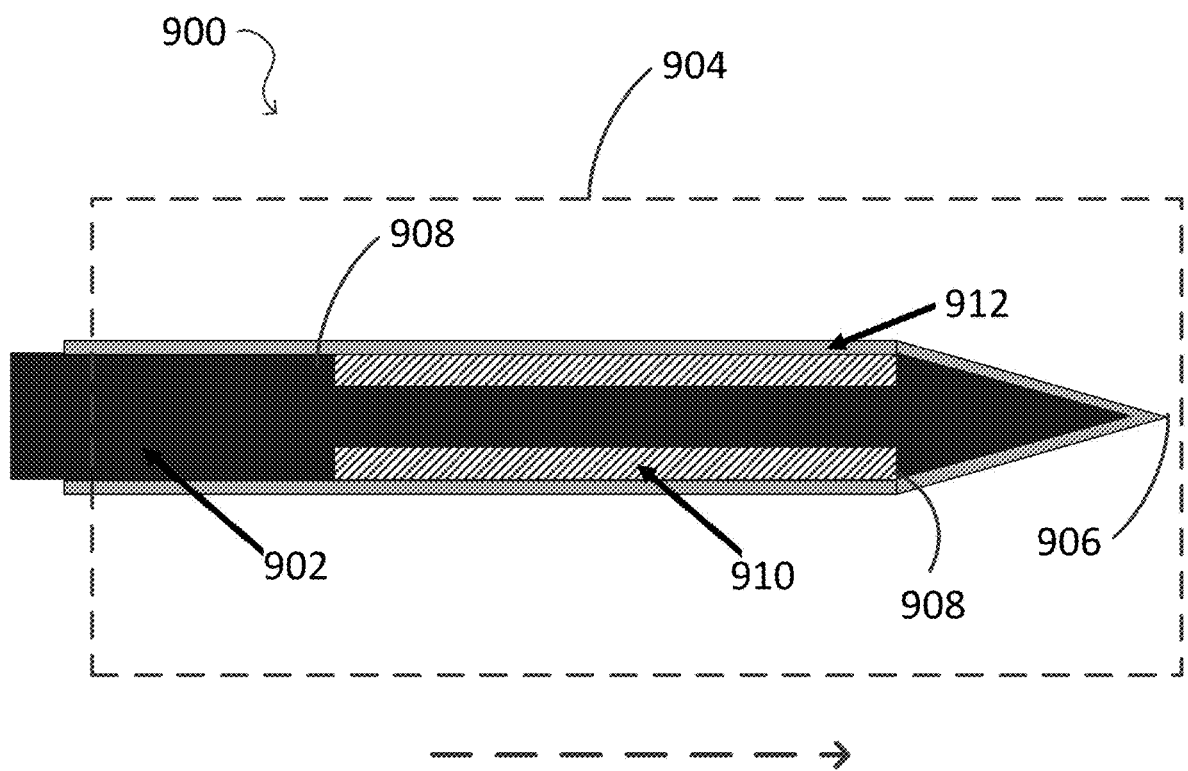
FIG. 9 is a schematic of an example of a sampling instrument with an over-coating according to the present disclosure.

FIG. 9 is a cross-sectional illustration of a sampling instrument according to the present disclosure along the axis of insertion that has an additional coating. The sampling instrument (900) has a support structure (902) having an insertion portion (904) and is in a needle-like shape having a needle point end (906). The support structure (902) has two protrusions (908) and is coated with an extraction phase (910) between the two protrusions (906). The insertion portion (904) is coated with an additional coating (912). The dashed arrow indicates the direction of insertion.

Figure 10:
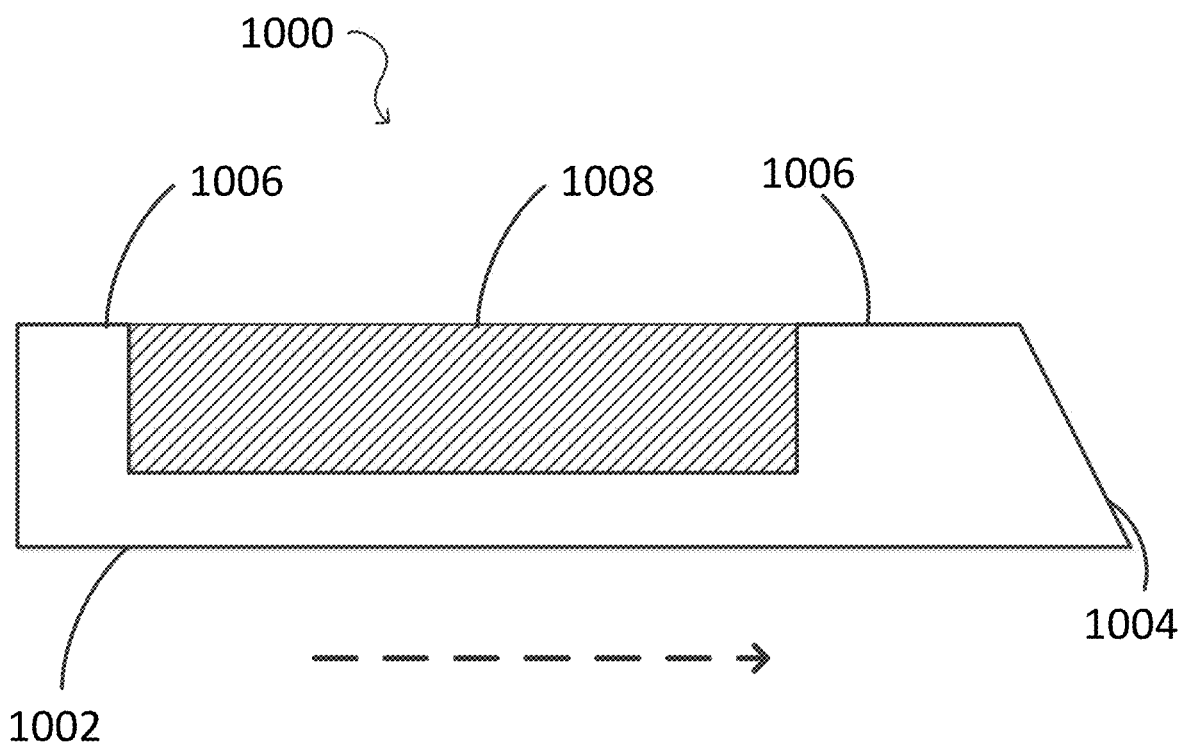
FIG. 10 is a schematic of an example of a sampling instrument according to the present disclosure.

In some examples according to the present disclosure, the sampling instrument may have a biopsy needle-like shape, for example when a combination of extracting a component of interest and extracting a tissue is desirable. The protrusion of the biopsy needle-like instrument shields the extraction phase during the shear forces during tissue cutting. FIG. 10 is an image of a biopsy needle-like shape instrument (1000), which has a support structure (1002) in a biopsy needle-like shape having a biopsy needle end (1004). The support structure (1002) has two protrusions (1006) and is coated with an extraction phase (1008) between the two protrusions (1006). The dashed arrow indicates the direction of insertion.

Figure 11:
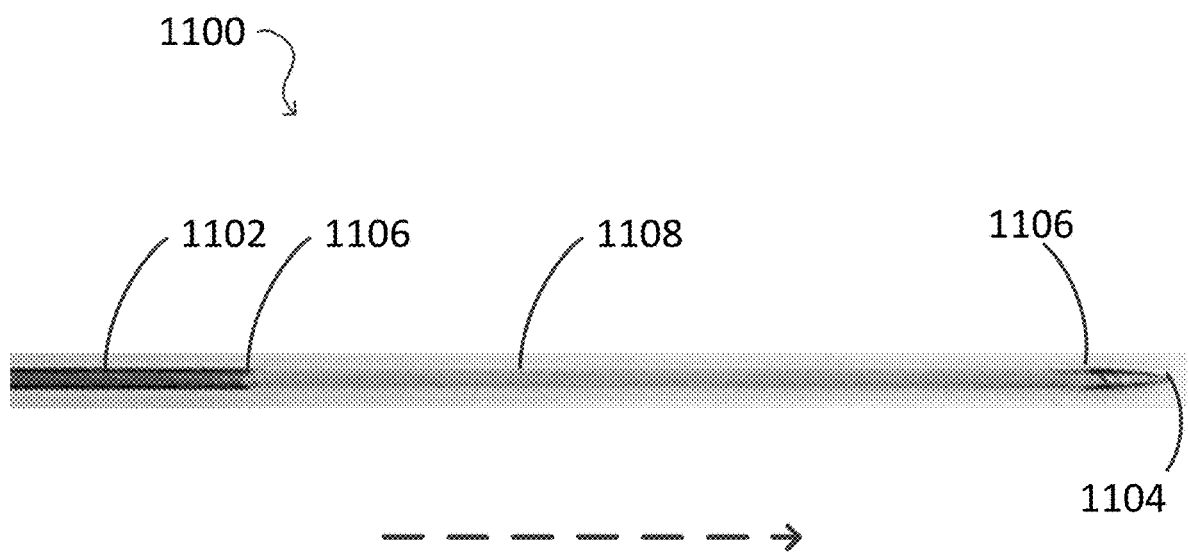
FIG. 11 is an image of a miniaturized sampling instrument according to the present disclosure.

The sampling instrument according to the present disclosure may be miniaturized, for example when decreasing the invasiveness into the solid or semisolid material, the sample, or a combination thereof during insertion is desirable. FIG. 11 is an image of a miniaturized sampling instrument (1100), which has a support structure (1102) in a needle-like shape having a needle point end (1104). The support structure (1102) has two protrusions (1106) and is coated with an extraction phase (1108) between the two protrusions (1006). The dashed arrow indicates the direction of insertion. The sampling instrument has a diameter of about 200 µm, the extraction phase coating has a thickness of about 10 µm, and the distance between the two protrusions is about 1 cm.

Figure 12A:
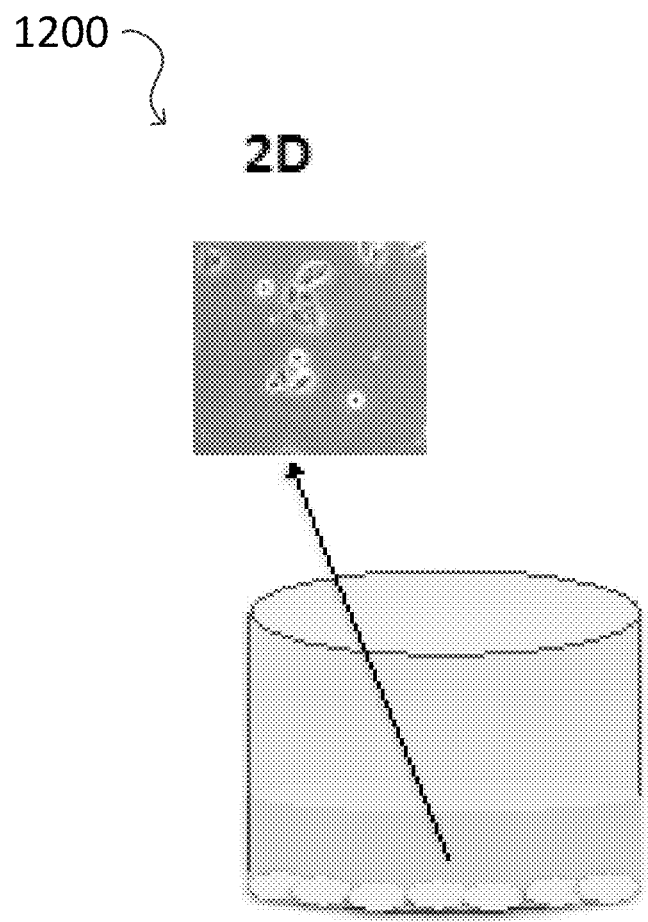
FIGS. 12A-C are illustrations of a 2D culture (FIG. 12A), a 3D culture (FIG. 12B), and a miniaturized sampling instrument according FIG. 11 inserted into a 3D culture (FIG. 12C).
Figure 12B:
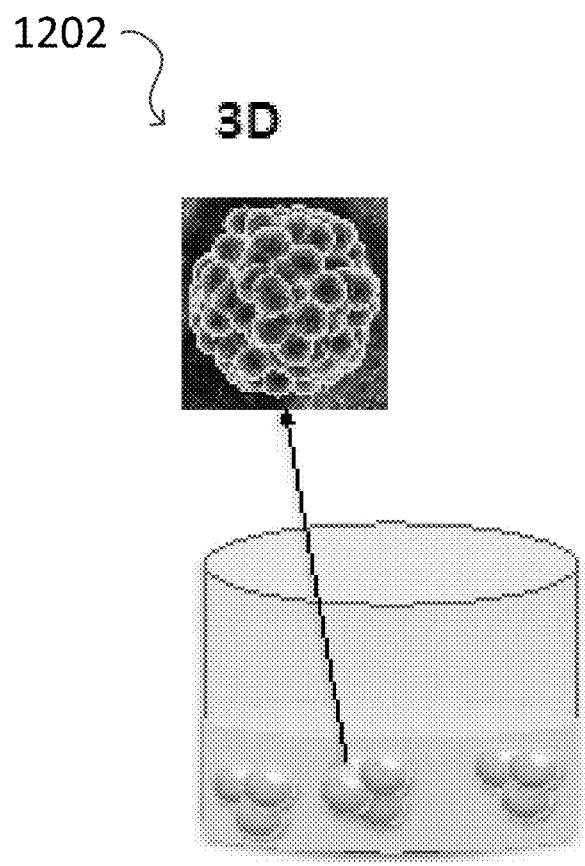
Figure 12C:
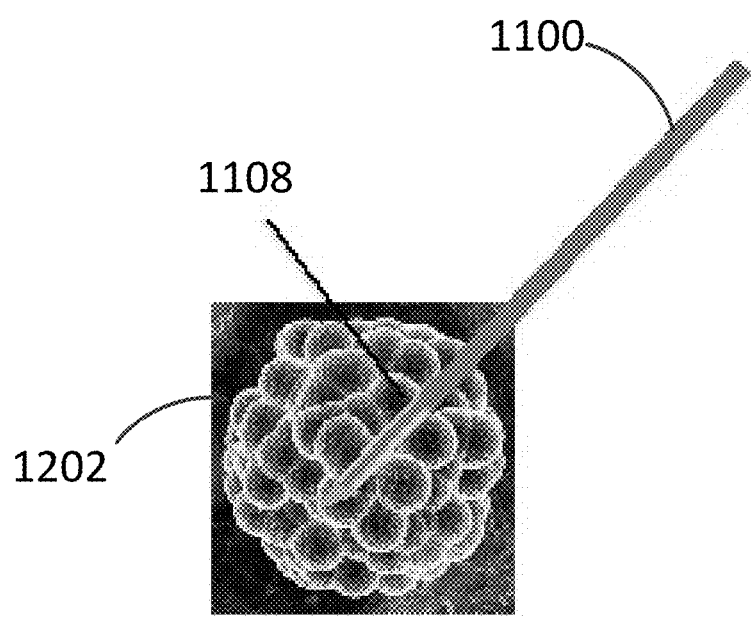

The sampling instrument according to the present disclosure may be used to sample small objects, for example, tumor spheroids or tissues cultured in three-dimension models (3D). The three dimension format was introduced primarily to cancer study as it is much more relevant physiologically than two-dimensional models. Currently it is not only used for tumor cultivation but other pathological and physiological cells and tissues and results obtained from these models show a better correlation with in vivo conditions than 2D data. However, many of the assays routinely used for analysis of 2D cultures are not compatible with 3D systems. Many of the assays routinely used for analysis of 2D cultures require direct contact of the cells with the flat bottom surface to perform the measurement. The spheroids growing as 3D are suspended in a matrix or scaffold, which restricts direct contact with some 2D detectors. The sampling instrument according to the present disclosure, for example the miniaturized sampling instrument shown in FIG. 11, may not suffer from the same drawbacks of the assays routinely used for analysis of 2D cultures. As described above, the miniature size of the sampling instrument may decrease the size of the incision in the tissue sample and decrease the damage of the tissue. FIGS. 12A-C illustrate a 2D culture (FIG. 12A, 1200), a 3D culture (FIG. 12B, 1202), and a miniaturized sampling instrument according FIG. 11 (1100) inserted into the 3D culture (FIG. 12C; 1202). As discussed above, some examples of the sampling instrument are configured to allow multiple extractions from the same sample, which may cause less damage to the sample as some traditional analyses require the addition of chemicals for multiple extractions, which inhibit the growth or kill the cells. Some examples of the present disclosure may be more cost effective than traditional analyses because, as discussed below, some examples of the sampling instrument according to the present disclosure are compatible with high throughput analyses, such as 96 well plat formats.

The miniaturized sampling instrument according to the present disclosure may also allow for parallelization and higher throughput in analysis of tissue samples to more efficiently process a large number of samples. As shown in Examples 2 and 6, the protrusion of the sampling instrument shields the extraction phase coating during insertion through a septum, as well as shielding the extraction phase coating during repeated insertions, thereby may decrease the number of steps for sampling as compared to sampling devices that require sheaths.

Figure 13:
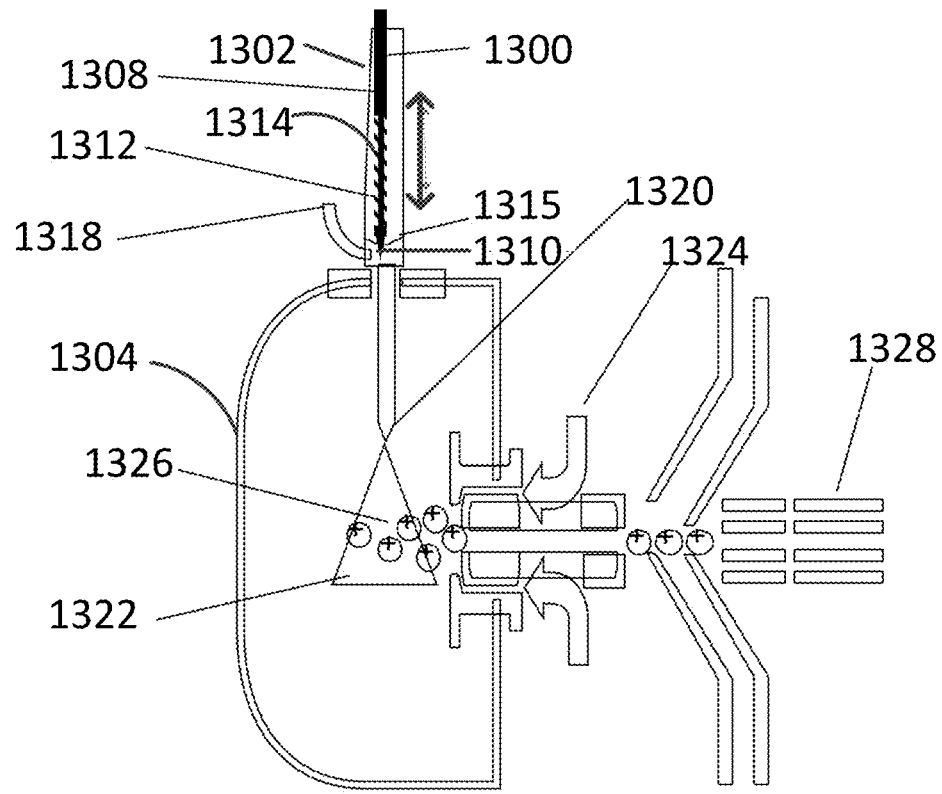
FIG. 13 is a schematic of an example of a sampling instrument according to the present disclosure in a desorption chamber coupled to an electrospray ionization source for a mass spectrometry analyzer.

The sampling instrument according to the present disclosure may be coupled to a mass spectrometer reaction vessel, or desorption loop. FIG. 13 is an illustration of a sampling instrument according to the present disclosure (1300) coupled to desorption chamber (1302), which is coupled to an electrospray ionization (ESI) mass spectrometer (MS) (1304). The sampling instrument (1300) has a support structure (1308) in a needle-like form having a needle tip (1310), the support structure (1308) that has one protrusion (1312) in a screw-like configuration, and is coated with an extraction phase (1314) located between every adjacent pair of threads. The sampling instrument (1300) is configured to couple its needle-like tip (1310) to an aperture of a membrane (1315) located at the bottom of the desorption chamber (1302) thereby plugging the aperture and isolating a region of space containing the extraction phase coating (1314) within the desorption chamber (1302). The size of the desorption chamber (1302) may vary depending on the size of the sampling instrument. The conditions within the desorption chamber (1302) may also be varied to decrease the overall time scale for desorption, for example by applying agitation conditions such as sonication and vibration, as well as varying the temperature, for example by increasing the temperature, within the desorption chamber (1302). During desorption, the desorption chamber (1302) is filled with the desorption fluid, for example a solvent, from the fluid tube (1318) connected to a fluid valve, for example by increasing its flow from the fluid tube (1318) compared to the flow generated by the electrospray. After, the desorption chamber (1302) is emptied by reducing the flow from the fluid tube (1318) in comparison to the flow generated by the electrospray, or by turning off the flow from the flow tube (1318) completely, which results in a concentrated plug of the component of interest entering the electrospray needle (1320) followed by the plum (1322), where the desorption fluid is dried and reduced in size by hot gas flow (1324) until ions form (1326). These ions then pass into the mass analyzer (1328).

A desorption fluid level sensor may be installed to facilitate fault-free operation of the device (not shown). This may allow the operation of the electrospray source without being affected by the introduction and removal of the sampling instrument into the desorption chamber (1302). The sampling instrument (1300) may remain in the desorption chamber (1302) during emptying of the desorption fluid, or it may be removed from the desorption chamber (1302) after the desorption is complete.

The desorption chamber (1302) is configured to closely match the circumference of the sampling instrument (1300) to decrease the volume of the desorption solvent to: (1) increase the concentration of the component of interest; (2) reduce mixing of the electrospray flow; or (3) a combination thereof. The fluid tube (1318) may be located close to the entrance of the electrospray needle (1320) to decrease mixing in the chamber. A membrane forming an aperture attached to the end of the fluid tube (1318) to reduce mixing.

The movement of the sampling instrument may control the movement of the desorption solvent into the electrospray. In some examples according to the present disclosure, the desorption chamber comprises a membrane having an aperture adapted to receive the leading side of the sampling instrument and being in fluid communication therebetween with an analytical instrument, where moving the sampling instrument towards the membrane couples the leading side of the sampling instrument to the membrane and blocks the fluid communication, and moving the sampling instrument away from the membrane removes the blockage and allows fluid communication. As illustrated by the arrows in FIG. 13, when the sampling instrument (1300) is moved away from the membrane (1315) located at the bottom of the desorption chamber (1302), the aperture of the membrane (1315) is no longer plugged and the solvent may flow through the aperture into the electrospray. When the sampling instrument (1300) is moved towards the membrane (1315), the aperture of the membrane is plugged and fluid communication is blocked.

In some examples, the desorption chamber is coupled to a reaction vessel or a liquid media detection device, for example, a UV spectrometer, a UV/Vis spectrometer, fluorescence spectrometer, an infra-red spectrometer, and a photodiode array.

In some examples, several desorption chambers may be connected in parallel to the instrument facilitating higher throughput operation of the device. Plugging and unplugging the orifice in each chamber may be performed sequentially allowing high duty cycle of instrument operation. In some examples, a 96 substrate system can be used in combination with 96 well plate to further improve the duty cycle of the determinations, for example when high throughput is desirable. In other examples, a 12 substrate system can be used in combination with 12 well plate to further improve the duty cycle of the determinations, for example when high throughput is desirable. A nebulizer gas system may be used to accelerate the system flow by creating a pressure differential between the desorption chamber and the electrospray needle, for example when fast determination and high throughput operation is desirable. The parallel operation approach may be useful if desorption time is much longer than the time required for electrospray of the desorption chamber contents.

The desorption and analysis system described above is not limited to an electrospray interface for MS. Other MS interfaces may also be used, for example, thermospray, Atmospheric Pressure Chemical Ionization (APCI). Furthermore, other analyzers may be used, for example, ion mobility spectrometry (IMS), which includes nanoelectrospray, thermospray, microelectrospray, APCI, and Open Port Probe (OPP), or a flow injection analysis systems with optical, flame and other means of detection.

EXAMPLES

Figure 14A:
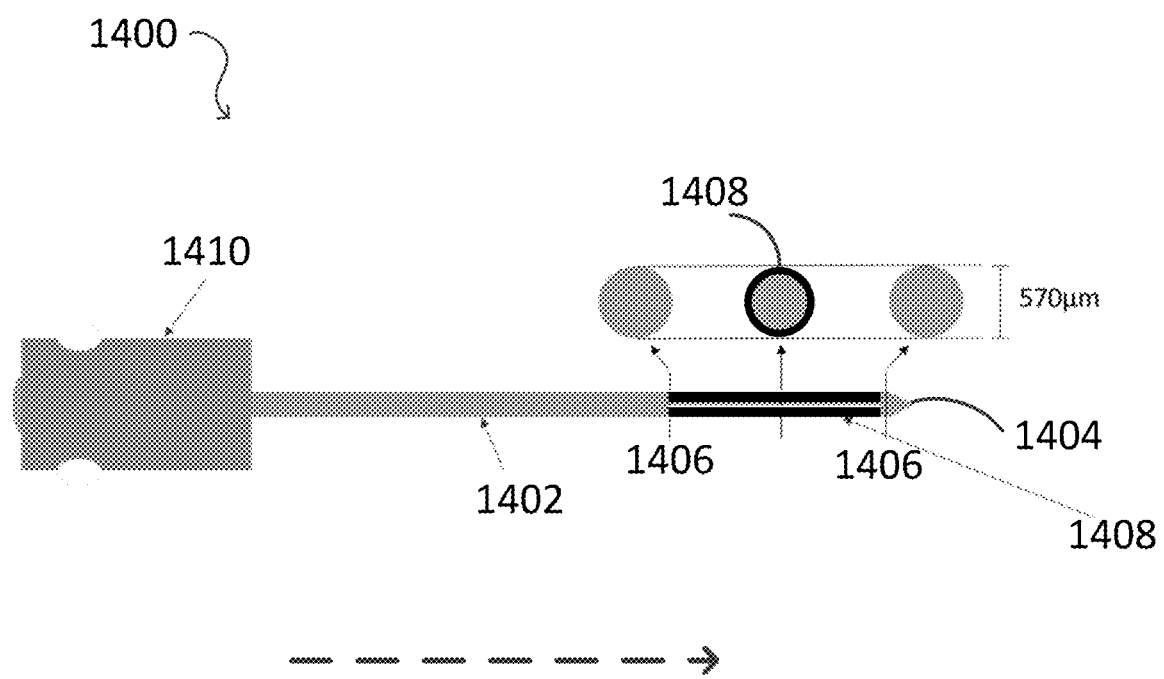
FIGS. 14A-B are illustrations of an example of a sampling instrument according to the present disclosure (FIG. 14A) and a sampling instrument that does not have a protrusion (FIG. 14B).
Figure 14B:
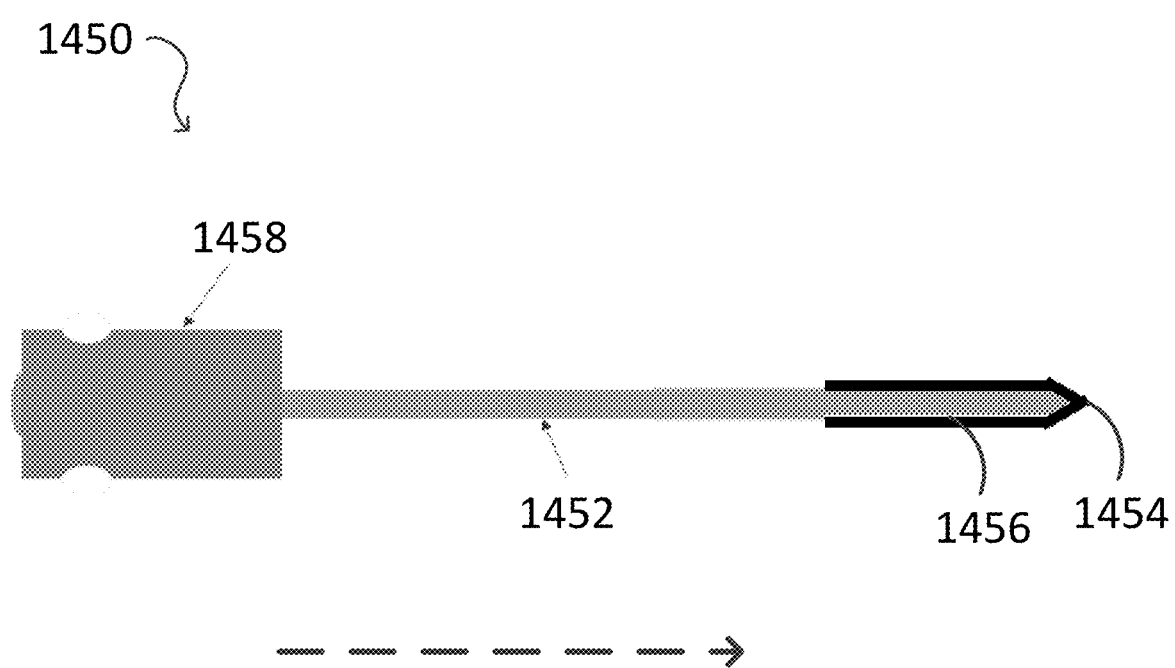
Figure 15:
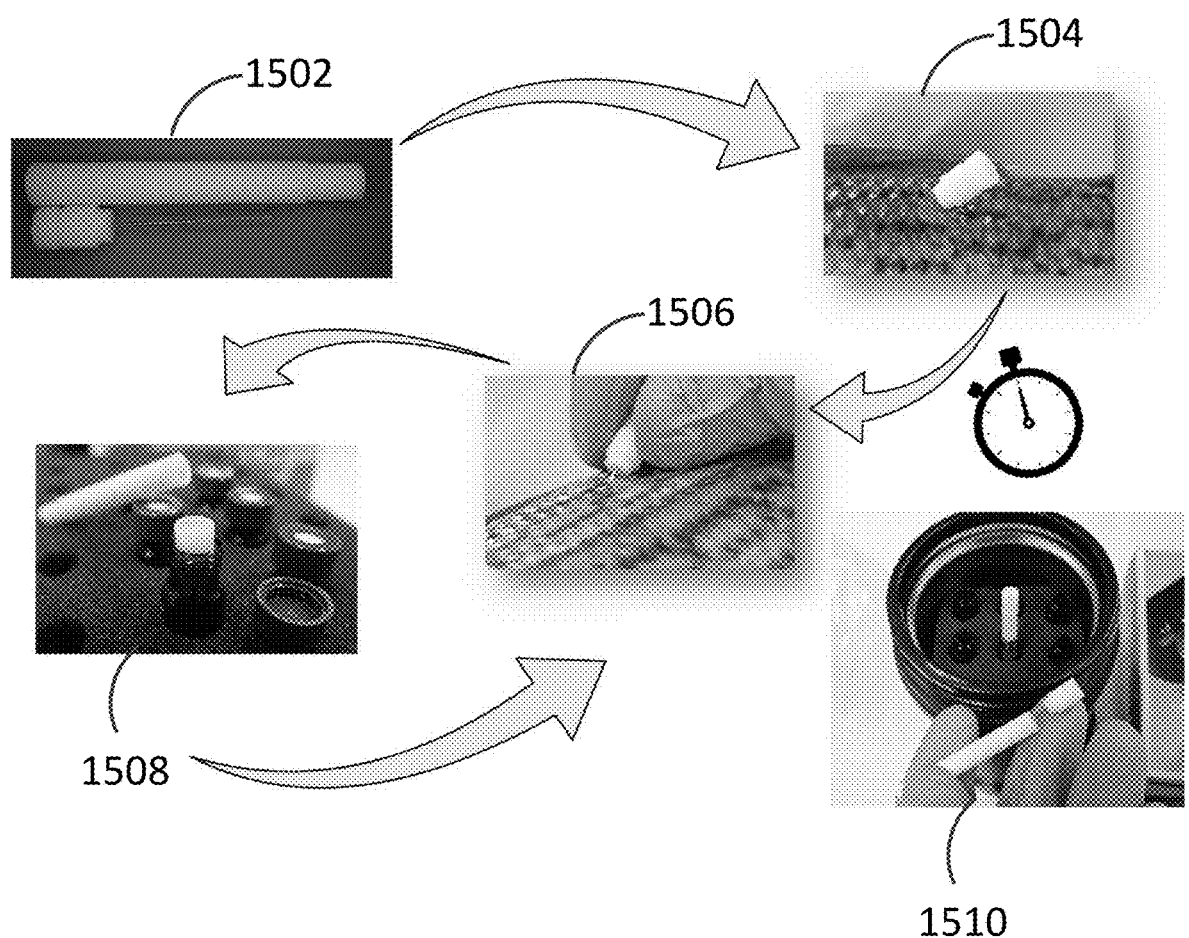
FIG. 15 is a schematic of a method of extracting a component of interest from fish tissue using a sampling instrument according to the present disclosure.

Example 1—The Protrusion Physically Shields the Extraction Phase Coating During Insertion Preliminary experiments to determine whether the protrusion shields the extraction phase coating were performed. For these experiments, a sampling instrument according to the present disclosure and a sampling instrument without a protrusion were used. FIGS. 14A-B are illustrations of cross-sections of a solid phase microextraction sampling instrument along the axis of insertion according to present disclosure (FIG. 14A) and a microextraction sampling instrument without a protrusion (FIG. 14B). FIG. 14A illustrates a sampling instrument (1400) having a support structure (1402) of a needle-like shape having a needle point end (1404). The support structure (1402) has two protrusions (1406) and is coated with hydrophilic-lipophilic balanced (HLB) particles suspended in a polyacrylonitrile (PAN) glue (1408) between the two protrusions to shield the PAN during insertion. As illustrated in the magnified schematic, the three identified cross-sectional plans are about equal in size. The support structure (1402) also has a backing (1410) that is about 6.5 mm in diameter and configured to be coupled to an airsoft gun. The dashed arrow indicates the direction of insertion. FIG. 14B illustrates a sampling instrument (1450) without a protrusion, and having a support structure (1452) of a needle-like shape having a needle point end (1454), the support structure (1452) partially coated with HLB-PAN (1456). The support structure (1452) has a backing (1458) that is about 6.5 mm in diameter and configured to be coupled to an airsoft gun. The dashed arrow indicates the direction of insertion. The HLB-PAN coating was used because of the wide variety of compounds that demonstrate affinity for HLB. In order to test the robustness of the instruments, as well as facilitate rapid one-handed sampler introduction, the instruments were incorporated into custom projectiles and fired from an unmodified Airsoft™ gun into fish scales. FIG. 15 is a schematic of the solid phase microextraction method. The sampling instruments are removed from their covers (1502) and coupled to and airsoft gun and fired at a speed of approximately 90 m·s$^{-1}$ at point blank range into a fish (1504). The speed was selected to simulate aggressive handling and demonstrate the ability of the exemplary sampling instrument to be used as a rapid sampling tool for in vivo applications. After about 60 minutes, the sampling instruments were removed from the fish (1506). The sampling instruments were then cleaned with Kimwipe to remove any fish tissue and rinsed for about 10 seconds with nan-pure water (1508). After the washes, the sampling instruments are inserted back into their covers for storage before analysis (1510).

Figure 16A:
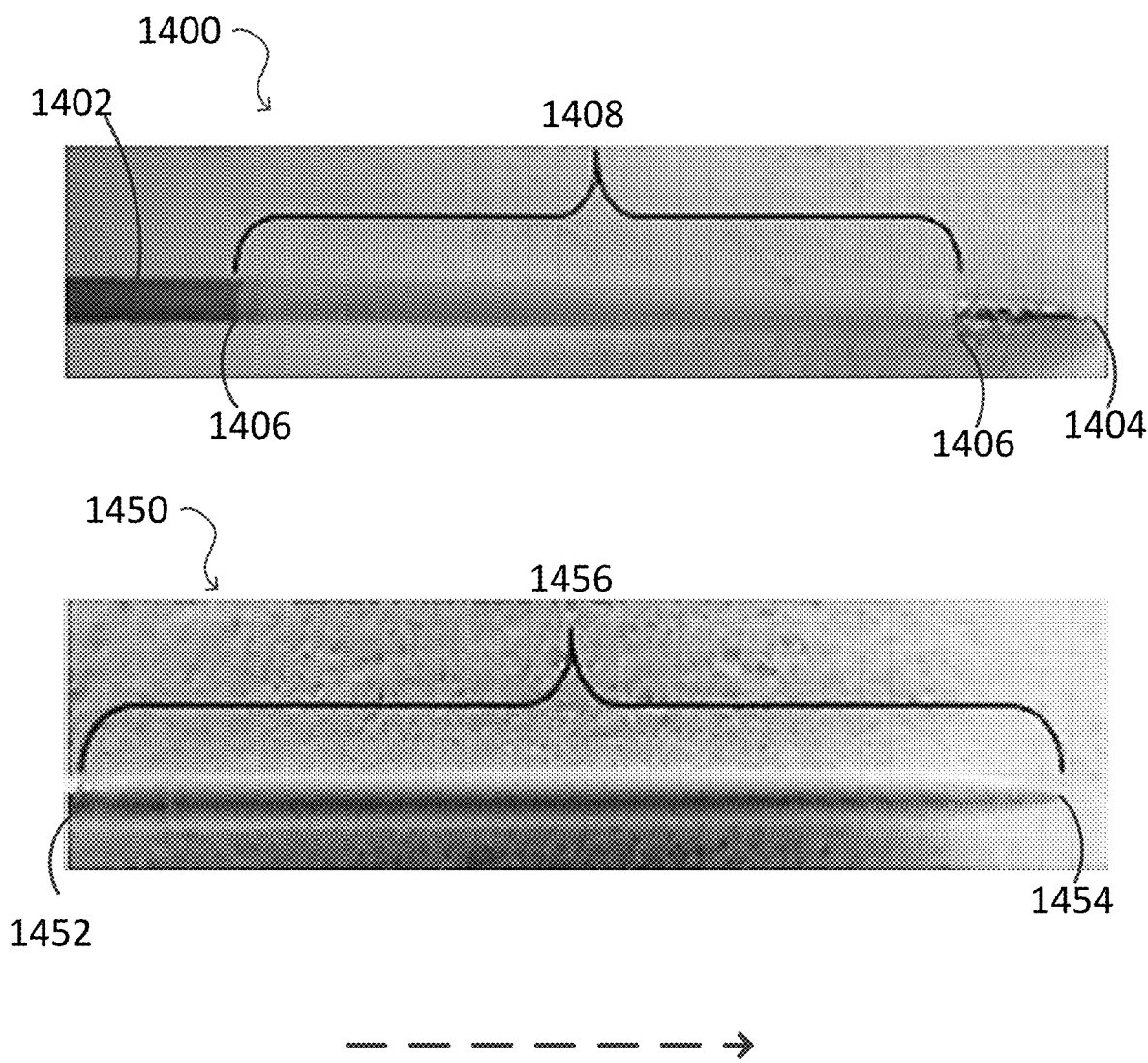
FIGS. 16A-B are images of the sampling instrument illustrated in FIG. 14A (top images) and the sampling instrument illustrated in FIG. 14B (bottom images).
Figure 16B:
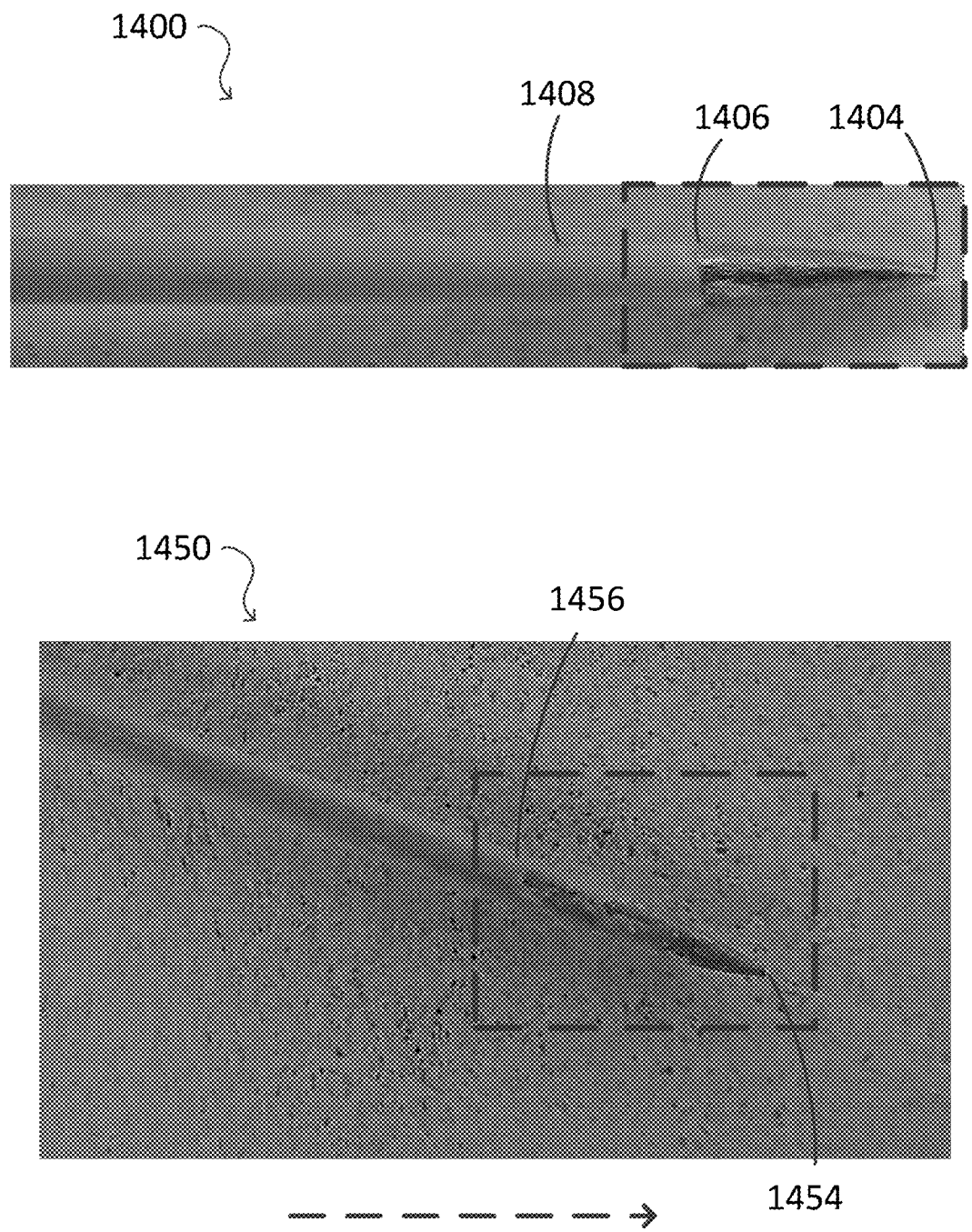

FIGS. 16A-B are images of the sampling instrument as illustrated in FIG. 14A (top images) and the sampling instrument without a protrusion as illustrated in FIG. 14B (bottom images), before (FIG. 16A) and after (FIG. 16B) insertion into the fish sample. As shown in FIGS. 16A-B, the sampling instrument without a protrusion to shield the extraction phase coating (bottom images) had more damage upon impact and puncture, including increased disassociation of the extraction phase coating from the sampling instrument. Conversely, the sampling instrument according to the present disclosure (top images) had less damage, including decreased disassociation of the extraction phase coating from the sampling instrument. The dashed arrows indicate the direction of insertion.

Example 2—Puncturing a Septum to Access the Sample

In order to assess the ability of the protrusion to protect the extraction phase coating from chemical changes resulting from puncture events, two sets of five sampling instruments according to the present disclosure were used to perform extractions from mass spectrometer (MS) grade water spiked with seven pharmaceutical target compounds (sertraline, fluoxetine, paroxetine, diazepam, salbutamol, ranitidine, and codeine at a concentration of 15 ng/mL). One set of sampling instruments was first forced through conventional liquid chromatography (LC) autosampler pre-slit septa in order to access the sample. While the second set was exposed directly to the spiked solution.

Extractions were performed for 2 minutes using vortex agitation. Once completed, the sampling instruments were removed from the sample solution and desorbed into mass spectrometer grade methanol at 1500 rpm for 10 minutes. No carry-over of the target compounds on the sampling instruments was verified by performing a second desorption. Analysis Method #1 (Table 1) was used during the LC separation and MS determination of these target compounds, having each desorption solution injected in triplicate.

Figure 17A:
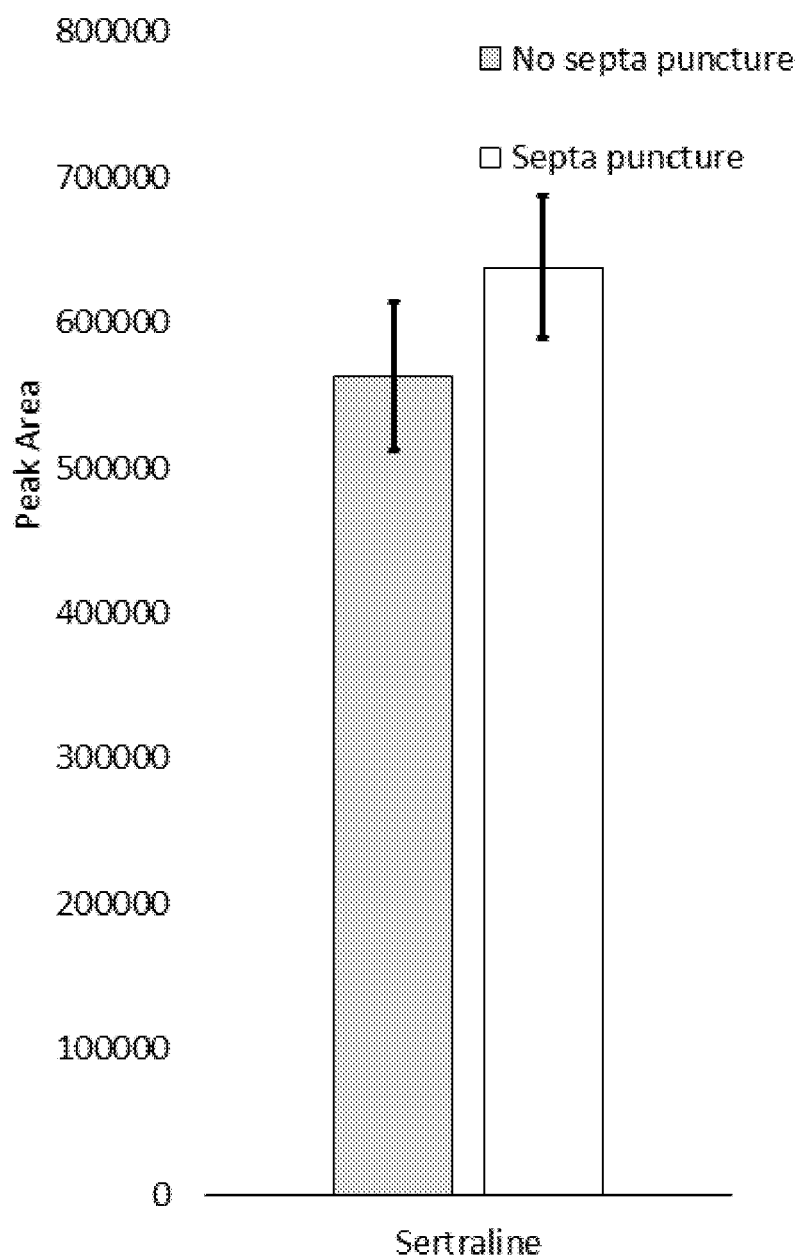
FIGS. 17A-C are graphs illustrating a comparison between the amount of component of interest extracted in an aqueous sample using a sampling instrument according to the present disclosure, with and without puncturing of septa to access the sample.
Figure 17B:
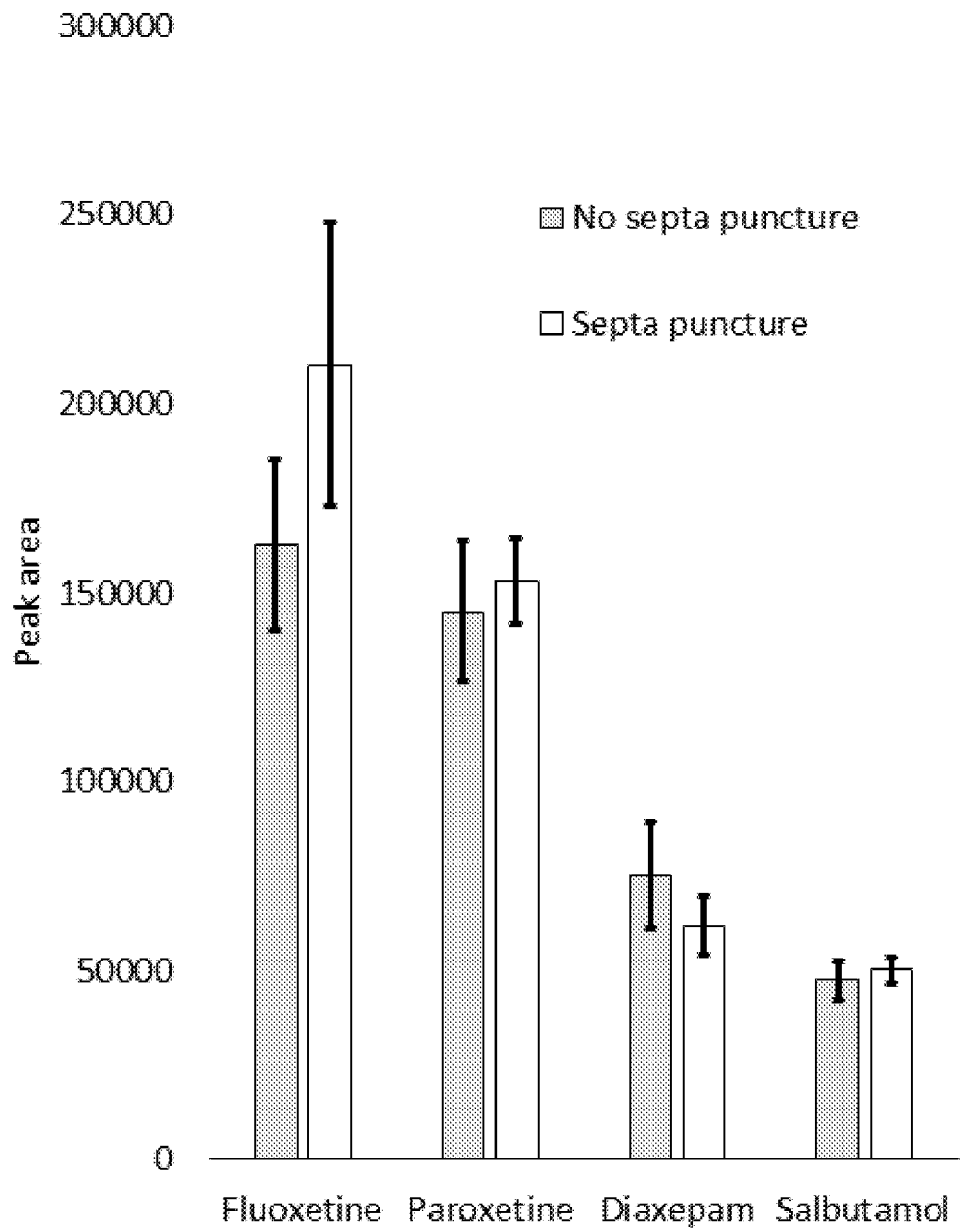
Figure 17C:
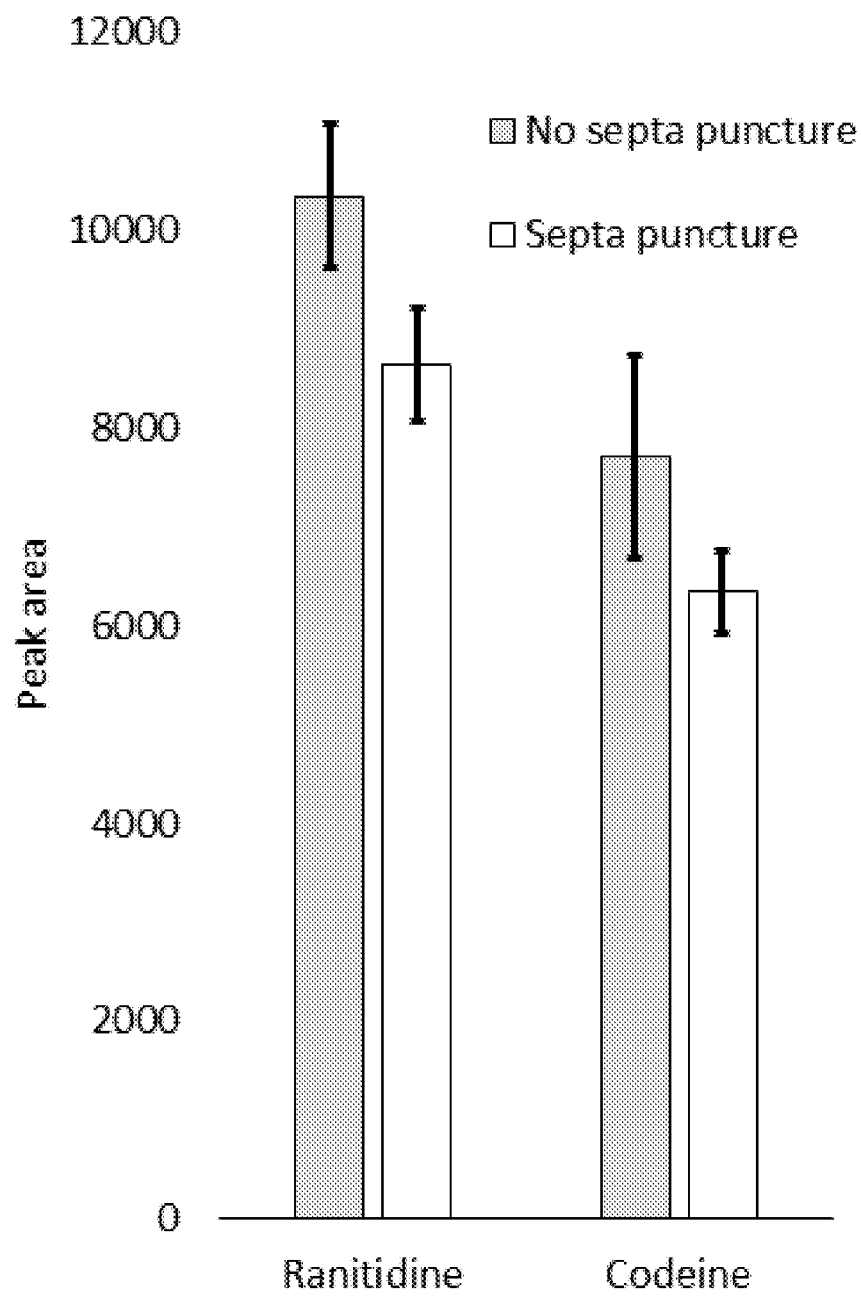
Figure 18A:
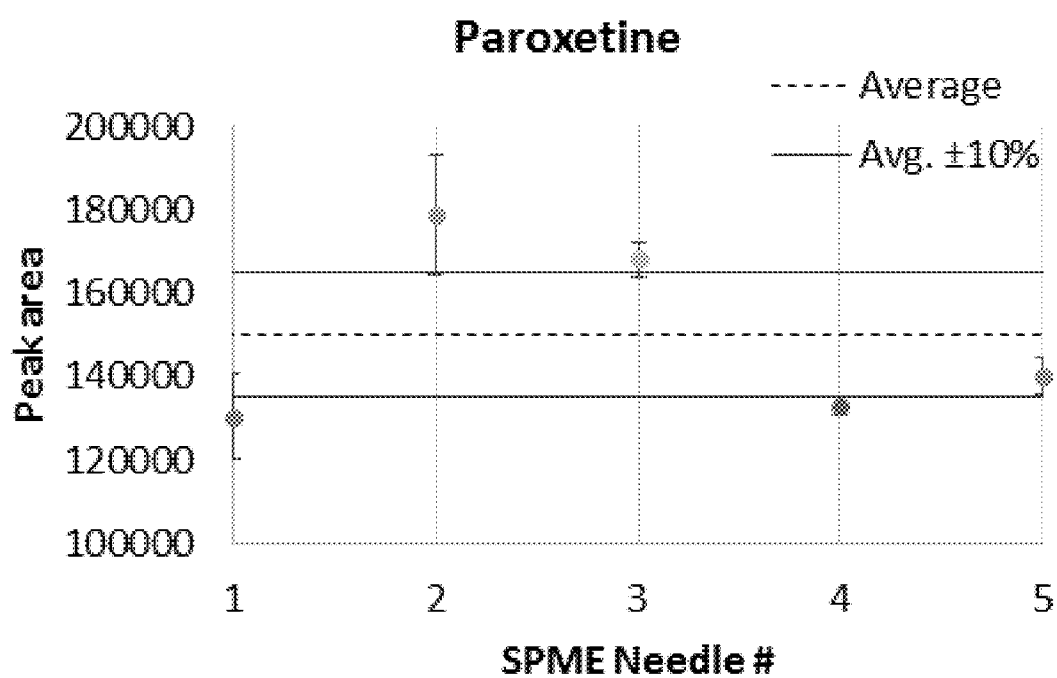
FIGS. 18A-G are graphs illustrating the reproducibility of using five sampling instruments according to the present disclosure for extracting components of interest from a water sample. The dashed lines represent the average. The horizontal lines above and below the dashed lines represent 10% relative standard deviations.
Figure 18B:
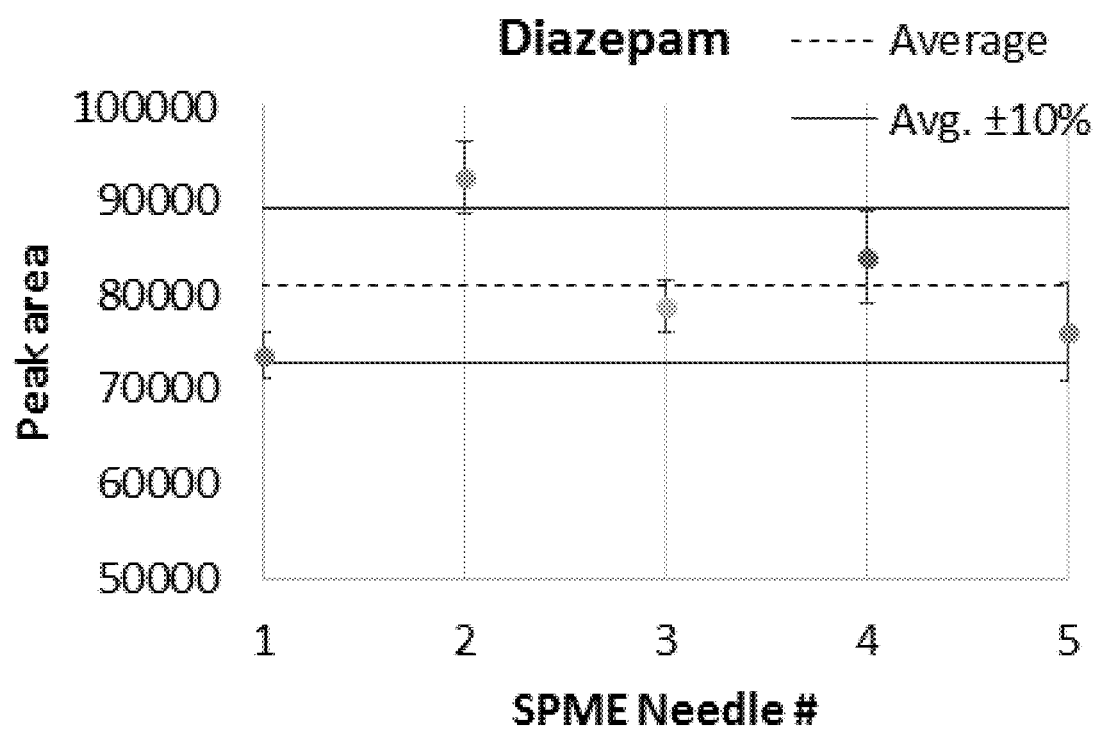
Figure 18C:
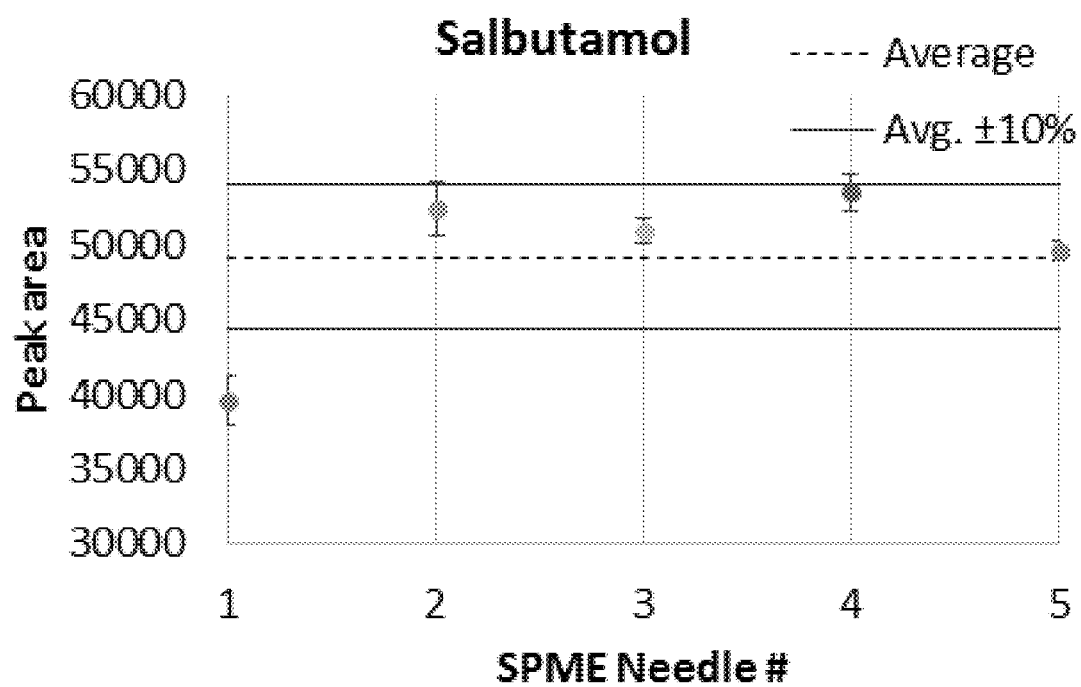
Figure 18D:
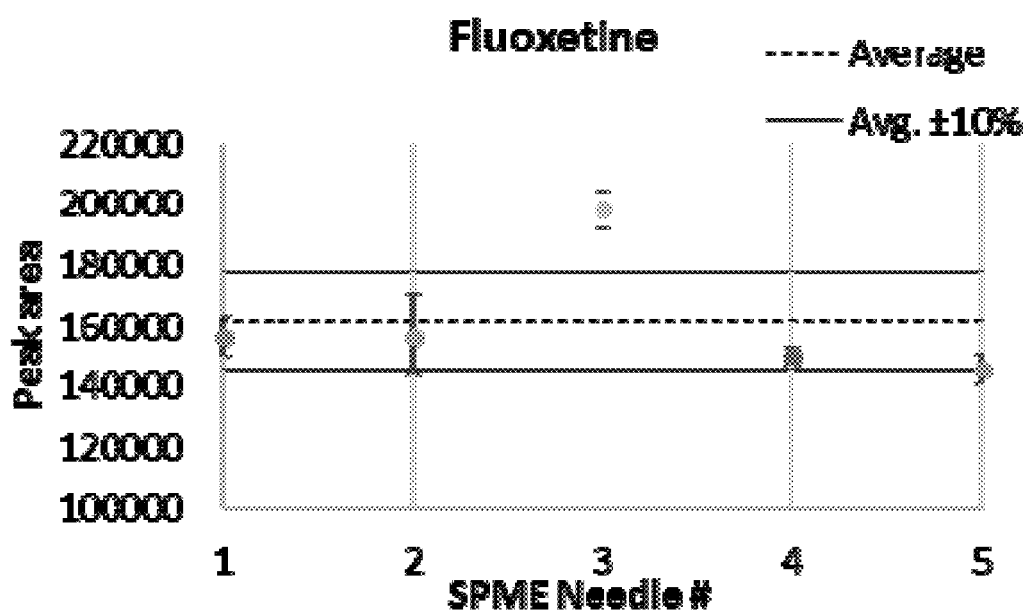
Figure 18E:
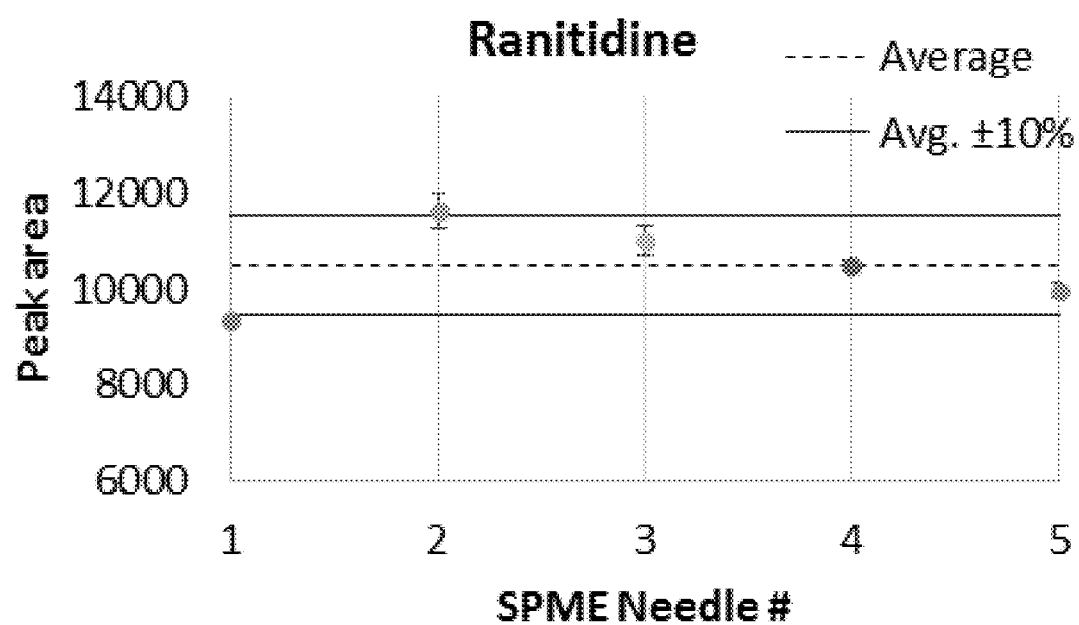
Figure 18F:
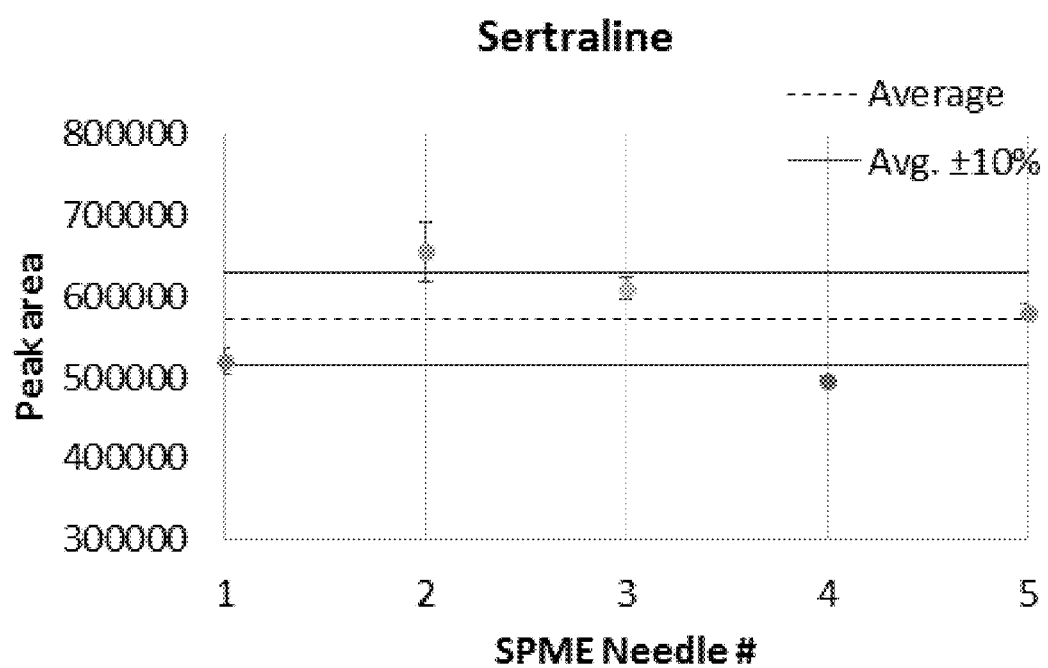
Figure 18G:
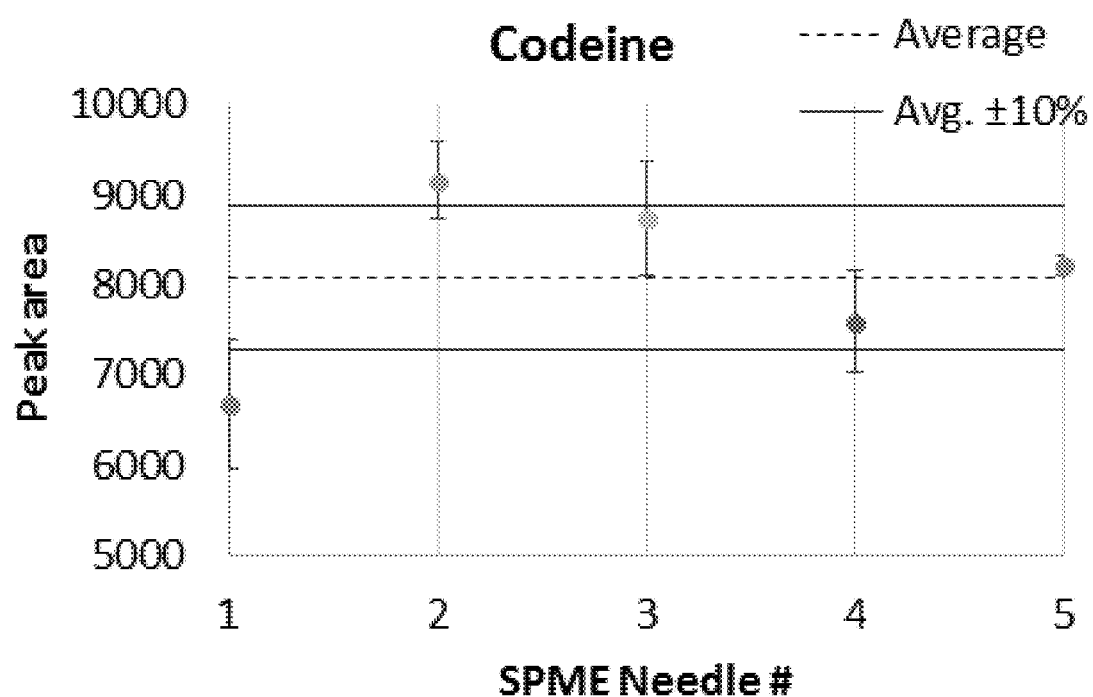

As shown in FIGS. 17A-C, method response for the targeted compounds was generally comparable for both sets of sampling instruments studied, demonstrating the ability of the sampling instruments to be used in high-throughput applications where septa capped vials are used to enclose a sample, wash or desorption solution.

gated by performing extractions from 1.5 mL of MS grade water spiked at 20 ng/mL using a 2 minute extraction under vortex agitation. Following extractions, the sampling instruments were rinsed in 1.5 mL of mass spectrometer grade water and desorbed into methanolic solutions. Upon instrument analysis using Analysis Method #1 of Example 2, Table 1, <14% RSD was observed across all sampling instruments, with no internal standard correction (n=5, FIGS. 18A-G). Subsequently, intra reproducibility of the sampling instruments was observed over 15 septa puncture-based samplings. Here, a sampling instrument according to the present disclosure that was coated with HLB-PAN, was pushed through conventional LC autosampler pre-slit septa caps to access a sample solution consisting of a 1M, pH=7.1 phosphate buffer solution (PBS) spiked at 30 ng/mL. Extractions were performed using vortex agitation for 2 minutes. Afterwards, the sampling instruments were rinsed in 1.5 mL of MS grade water and desorbed into a methanolic solution. Upon instrumental analysis using Analysis Method #1 of

TABLE 1

Analysis method #1-Chromatographic solvent gradient along with positive H-ESI ionization conditions with SRM transitions.
Description:
Separations were performed on Ascentis Express F5 HPLC PFP column (2.1 mm × 100 mm, 2.7 μm) using a three mobile phase system consisting of 0.1% formic acid (FA) in water (A), 0.1% formic acid in acetonitrile (B), and 0.1% FA in methanol (C). Specifics such as solvent gradient, ionization conditions and SRM transitions are outlined below.

Mobile phase gradient

| Time (min) | Percent composition | | | Flow (μL/min) |
| --- | --- | --- | --- | --- |
| | A | B | C | |
| 0 | 90 | 5 | 5 | 300 |
| 0.5 | 90 | 5 | 5 | 300 |
| 7 | 0 | 50 | 50 | 300 |
| 12 | 0 | 25 | 75 | 300 |
| 15.3 | 0 | 25 | 75 | 300 |
| 15.5 | 90 | 5 | 5 | 300 |
| 17.5 | 90 | 5 | 5 | 300 |

Mass spectrometer conditions

Spray voltage: 1300 V
Vaporizer temperature: 275° C.
Sheath gas: 30
Auxiliary gas: 30
Sweep gas: 2
Capillary temperature: 275° C.

SRM parameters by target compound

| Compound | Parent (Q1) | Daughter (Q3) | Collision energy (eV) | S-Lens |
| --- | --- | --- | --- | --- |
| Diazepam | 285.056 | 193.079 | 30 | 115 |
| Ranitidine | 315.128 | 176.024 | 16 | 92 |
| Codeine | 300.134 | 152.059 | 60 | 120 |
| Paroxetine | 330.129 | 192.097 | 19 | 133 |
| Fluoxetine | 310.121 | 44.157 | 13 | 76 |
| Sertraline | 306.057 | 158.955 | 29 | 75 |
| Salbutamol | 240.147 | 148.071 | 16 | 79 |

Example 3—Inter and Intra Reproducibility of the Sampling Instruments

Inter reproducibility of sampling instruments according to the present disclosure coated with HLB-PAN was investi- Example 2, Table 1, a RSD of <13% for all compounds tested was observed, using no internal standard correction. The exception to this observation was that of salbutamol, which demonstrated an intra % RSD of 21, perhaps due to the relatively small amount of compound extracted (see Table 2).

TABLE 2

Intra reproducibility of sampling instruments according to the present disclosure over 15 septa puncture events for the targeted analysis of pharmaceuticals compounds in pH = 7.2, 1M phosphate buffer saline at 30 ng/mL.

| Compound | log P | ng extracted | % RSD |
|---|---|---|---|
| Sertraline | 4.81 | 12 | 7 |
| Fluoxetine | 4.09 | 10 | 13 |
| Paroxetine | 3.89 | 7 | 11 |
| Diazepam | 2.91 | 4 | 7 |
| Ranitidine | 1.23 | 1 | 9 |
| Codeine | 1.20 | 1 | 12 |
| Salbutamol | 0.01 | 0.1 | 21 |

Example 4—Extraction of Pharmaceuticals from Plasma in a Pseudo High-Throughput Application Human plasma was spiked with the pharmaceuticals carbamazepine, ranitidine, diazepam and monensin at a concentration of 75 ng/mL. The spiked plasma was then agitated at 400 rpm for 5 hours to ensure homogeneity of the spiked sample before being divided into 1.6 mL aliquots in 2 mL amber vials. Prior to performing extractions, 3 sampling instruments according to the present disclosure and 3 mixed mode SPME fibers were conditioned for 30 minutes in 50:50 methanol:water at 1200 rpm. Extractions using the sampling instruments were performed by pulling the sampling instruments through the septa of the conditioning solution vial septa cap, and then piercing the septa of the 2 mL vial containing the spiked plasma sample. This sampling instrument/sample vial assembly was then vortexed for 4 minutes. The sampling instrument was then pulled through the septa of the sample vial and pushed through the septa of a wash solution containing 1.6 mL of MS grade water and vortexed for 5 seconds, this washing step was then repeated with a fresh washing vial. The sampling instrument was then pulled through the septa of the wash vial and pushed through the septa of a 2 mL vial containing 1.5 mL of 4:1 methanol/acetonitrile with 0.1% formic acid and agitated at 1500 rpm for 30 minutes. For the 3 mixed mode SPME fibers, extraction, washing and desorption conditions were the same as with the sampling instrument, however the cap of the vial was removed after each step and replaced as it was required to unscrew and pull the mixed mode SPME fiber through the septa, and then push it through the new cap backwards to prevent the coating from being pulled or pushed through the septa of the cap. No carry-over of analyte on the sampling instrument and fiber was verified by performing a second desorption. Desorption solutions were then analyzed using Analysis Method #1 outlined in Example 2, Table 1, having each desorption solution injected in triplicate.

Figure 19:
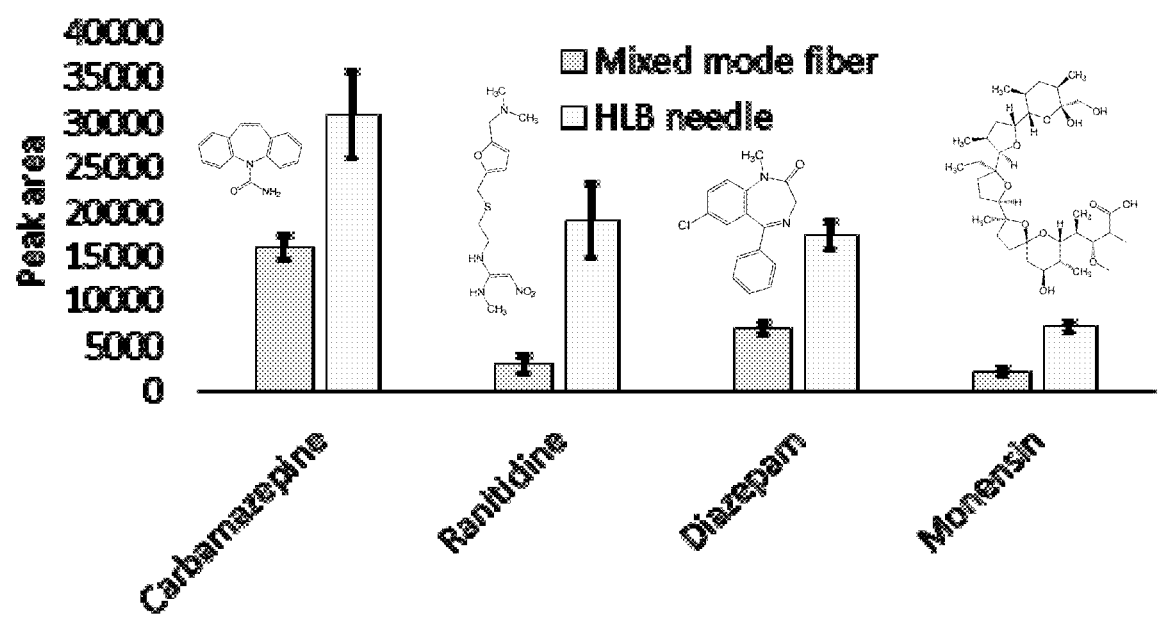
FIG. 19 are graphs illustrating data from extracting components of interest (Carbamazepine, Ranitine, Diazepam, and Monensin) from human plasma using a sampling instrument according to the present disclosure coated with hydrophilic-lipophilic balanced (HLB), and using mixed mode SPME fibers known in the art. The extraction consisted of 8 puncture and withdrawals through a vial septum.

As a proof of concept it was important to determine whether the sampling instrument was capable of performing high-throughput analysis. As high throughput SPME analysis methods often incorporate multiple steps including sampling, rinsing and extraction procedures the sampling instruments would be well suited as these solutions could be contained inside sealed vials limiting solvent loss due to evaporation, as opposed to the open bed 96-well plate typically used in high-throughput SPME applications. In addition, as the sampling instrument requires no additional support or device to pre-puncture the septa of sample vials, the hardware to execute a method of this kind would be limited to alterations made to pre-existing devices already available for open bed 96-well plate applications. As outlined, the procedure of this particular study contained four puncture events (through vial into solution), and four withdraw events (pull through septa, removing from solution) which would likely represent the most of this kind of stress applied to a sampling instrument in any one high throughput experiment. FIG. 19 represents the results of this particular study, where HLB-PAN sampling instruments were compared to commercially available mixed mode SPME fibers for the analysis of human plasma spiked with carbamazepine, ranitidine, diazepam and monensin.

The performance of the HLB sampling instrument under the experimental conditions was higher than that of the commercially available mixed mode SPME fibers as the method response was higher for all targeted analytes. In addition, reproducibility of the sampling instrument was better than the mixed mode SPME fibers, which had % RSDs for carbamazepine, ranitidine, diazepam and monensin of 8, 35, 11 and 18 respectively, while the SPME needle demonstrated % RSDs of 15, 22, 9 and 9 respectively.

Example 5—In Vivo Application of a Sampling Instrument Using Salmon Tissue

Upon the completion of the experimental validations demonstrating sampling instrument robustness and reproducibility in Examples 3 and 4, the sampling instrument according to the present disclosure was tested for in vivo samplings. To demonstrate this, the sampling instrument was applied in triplicate toward the targeted analysis of the poly-unsaturated fatty acids (PUFAs) docosahexaenoic acid (DHA), eicosapentaenoic acid (EPA), and arachidonic acid (AA) in salmon in a comparative study to mixed mode SPME fiber. The sampling instrument was coated with HLB-PAN or C18-PAN, and the SPME fibers were coated a strong cationic exchanged functionalized on a hydrophobic coating.

For a sample matrix, fresh, refrigerated salmon steaks were purchased from a local grocery store and left to reach room temperature for one hour prior to extraction. The sampling instrument and the fiber (n=3 in each case) were inserted into the face of the salmon steak. Fibers were inserted and left for one hour within the matrix to allow extraction to occur. In order to take full advantage of the robust sampling instrument, an additional three HLB-PAN sampling instruments were pushed through the protective flesh into the underlying tissue for one hour, an action not possible by the SPME fibers without the use of a protective sheathing needle or housing. After extraction, the sampling instruments and SPME fibers were washed 2 times for 5 seconds in MS grade water using vortex agitation, and desorbed in 100% acetonitrile for one hour at 1500 rpm. For analysis, full loop 10 µL injections were performed of the acetonitrile desorption solutions. A second desorption verified that no carry-over of analytes took place for the tested sampling instruments and SPME fibers. Desorption solutions were analyzed using Analysis Method #2 as outlined in Table 3.

TABLE 3

Analysis method #2-Chromatographic solvent gradient along with negative H-ESI ionization conditions with SRM transitions.
Description:
Samples were run on the same LC-MS/MS instrumentation as outlined in Analysis Method #1. Separations were performed on an X-bridge C18 HPLC column (2.1 mm × 150 mm, 2.5 μm). A binary mobile phase system was employed. Mobile phase A consisted of 90% water and 10% methanol, while mobile phase B was composed of 80% methanol and 20% acetonitrile. 2 Both Mobile phase A and B were modified to contain 5 mM ammonium acetate. Specifics such as solvent gradient, ionization conditions and SRM transitions are outlined below.

Mobile phase gradient

| Time (min) | Percent composition A | Percent composition B | Flow (μL/min) |
|---|---|---|---|
| 0 | 40 | 60 | 300 |
| 1 | 40 | 60 | 300 |
| 2 | 5 | 95 | 300 |
| 5 | 0 | 100 | 300 |
| 6 | 0 | 100 | 300 |
| 6.5 | 40 | 60 | 300 |
| 8 | 40 | 60 | 300 |

Mass spectrometer conditions

Spray voltage: −2600 V
Vaporizer temperature: 275° C.
Sheath gas: 30
Auxiliary gas: 30
Sweep gas: 2
Capillary temperature: 275° C.

SRM parameters by compound

| Compound | Parent (Q1) | Daughter (Q3) | Collision energy (eV) | S-Lens |
|---|---|---|---|---|
| Arachidonic acid | 303.431 | 260.610 | 17 | 132 |
| Docosahexaenoic acid | 327.098 | 284.672 | 16 | 134 |
| Eicosapentaenoic acid | 301.103 | 263.631 | 16 | 133 |

Figure 20:
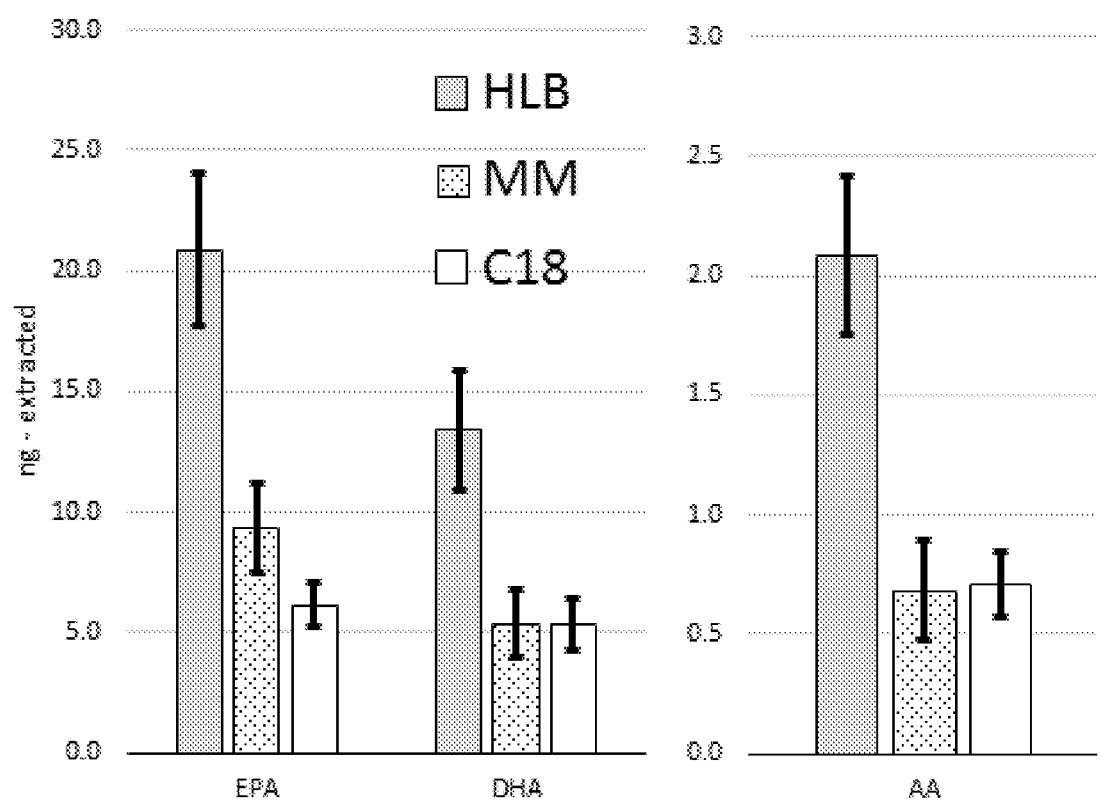
FIG. 20 are graphs illustrating data from extracting components of interest (eicosapentaenoic acid (EPA), docosahexaenoic acid (DHA), and arachidonic acid (AA)) from fish muscle tissue using sampling instruments according to the present disclosure coated with HLB or C18, and using mixed mode SPME fibers known in the art.

The studies demonstrate that the HLB coated sampling instrument extracted 3 to 4 times more PUFAs than C18 coated sampling instrument and mixed mode SPME fibers (n=3, FIG. 20), which were used in a previous, unpublished in vivo fish tissue study.

Figure 21:
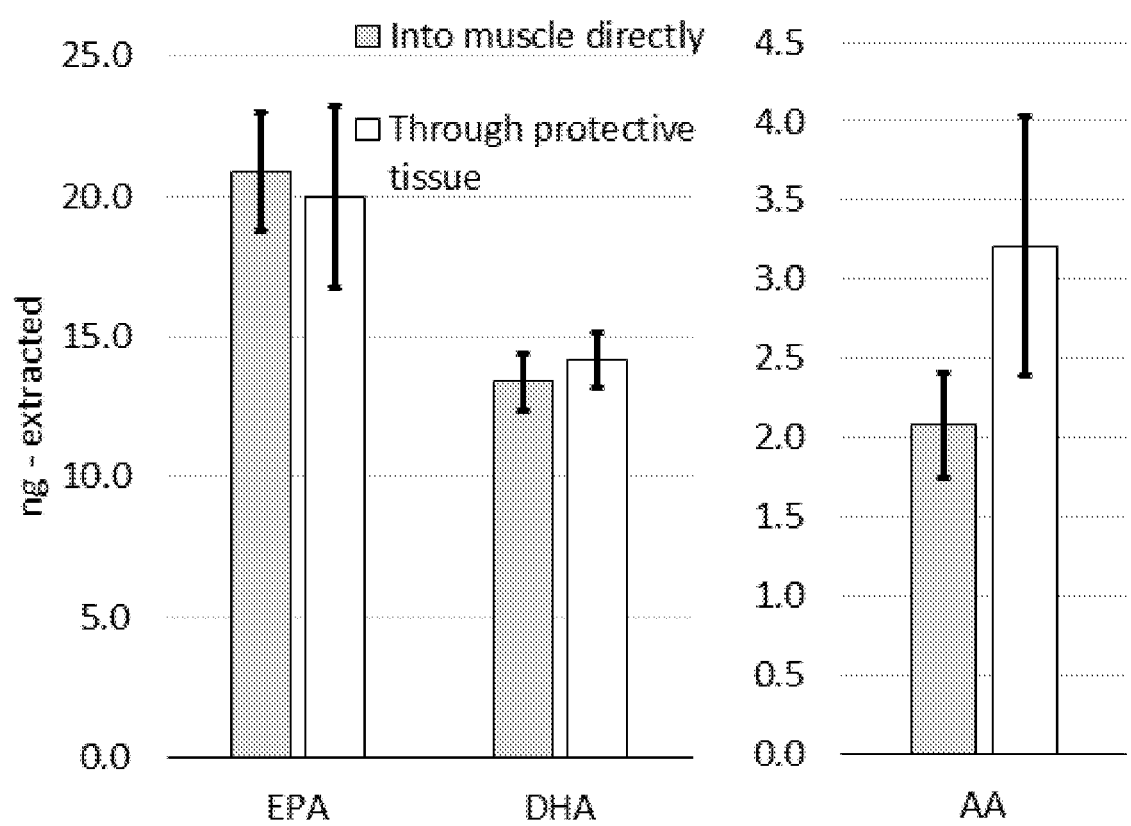
FIG. 21 are graphs illustrating data collected from extracting components of interest (eicosapentaenoic acid (EPA), docosahexaenoic acid (DHA), and arachidonic acid (AA)) from fish muscle tissue using sampling instruments according to the present disclosure coated with HLB. The instruments were either inserted into the muscle tissue directly or were pushed through the protective flesh of the fish before being inserted into the muscle tissue.

In addition, the process of forcing the HLB sampling instruments through the protective outer skin was shown to not affect PUFA extraction (FIG. 21). For this experiment, the performance of sampling instrument (n=3) that had been forced through the protective tissue was compared to a sampling instrument that had been pushed into muscle tissue directly. Interestingly, the sampling instrument that punctured the skin appeared to extract a somewhat greater amount of arachidonic acid than those that were pushed into the muscle tissue directly. This difference may not be significant, though one potential hypothesis for this observation is that levels of arachidonic acid may be greater closer to the surface of the tissue, or rather, closer to the scales. In any case, the sampling instrument can provide an easy-to-use and comparably reproducible method to traditional SPME fibers for the analysis of whole, unmodified tissues, and hence, in vivo applications.

Example 6—the Protrusion Physically Shields the Extraction Phase Coating During Multiple Insertions In order to identify the true robustness of the sampling instrument, sampling instruments were used to perform repetitive punctures of protective tissue by directly puncturing through the protective tissue of a salmon steak. Sampling instrument according to the present disclosure were pushed through the protective tissue by hand and then removed. After they were removed, the instruments underwent a desorption in 100% acetonitrile for about 1 hour at 1200 rpm, followed by washing and precondition as described in Example 5 prior to again being pushed through the protective tissue. This process was repeated for 9 puncture events. The experiment utilized five separate sampling instruments, each used for nine punctures. Most likely, an in vivo sampling instrument would be a single use instrument however even under these conditions no significant mechanical damage to the instruments was observed to occur over the duration of the study.

Example 7—Sampling Instruments with a PAN Over-Coating

In this preliminary work, it has been noted that the response of some sampling instruments according to the present disclosure may reduce after repetitive extractions from biological sample matrices resulting from the adhering of the matrix molecules, such as proteins, and other compounds associated with bio-fouling processes. As a result, the process of over-coating was investigated as a means by which to provide an additional coating, for example a smooth layer over the insertion portion of the sampling instrument. This smooth surface characteristic can limit matrix attachment and hence provide an enhanced biocompatible coating as well as provide a barrier between the matrix and extractive coating for the purpose of coating robustness, decreasing the amount of coating lost in the sample. Here, sampling instruments with their insertion portions over-coated with PAN were compared with non-over-coated sampling instruments. All the sampling instruments were coated with HLB extractive coatings of the same dimensions. Four sampling instruments of each type (over-coated and non-over-coated) were pushed into salmon tissue directly. Extraction, wash, desorption and analysis were conducted as in Example 5. Each sampling instrument was used in sequence for 4 repetitive extractions.

Figure 22A:
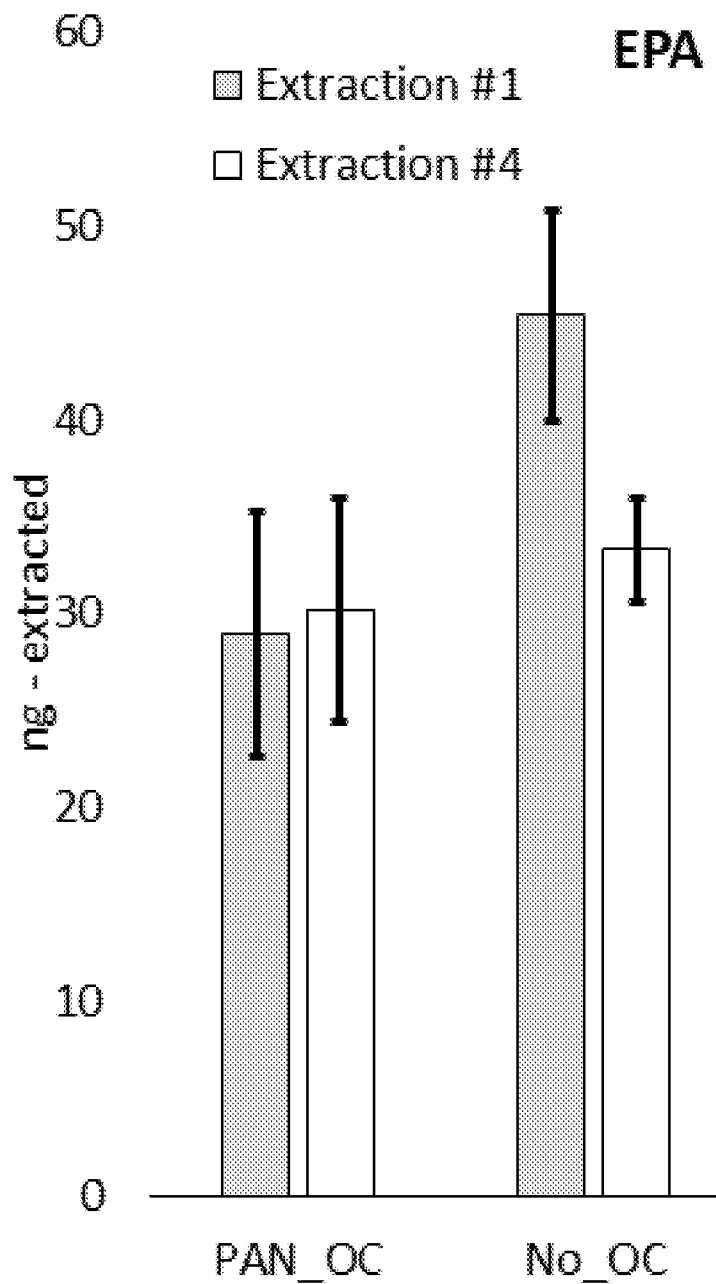
FIGS. 22A-B are graphs illustrating data from extracting components of interest EPA (FIG. 22A) and DHA (FIG. 22B) from fish tissue using sampling instruments according to the present disclosure coated with HLB in polyacrylonitrile (PAN), with and without an over-coating of PAN.
Figure 22B:
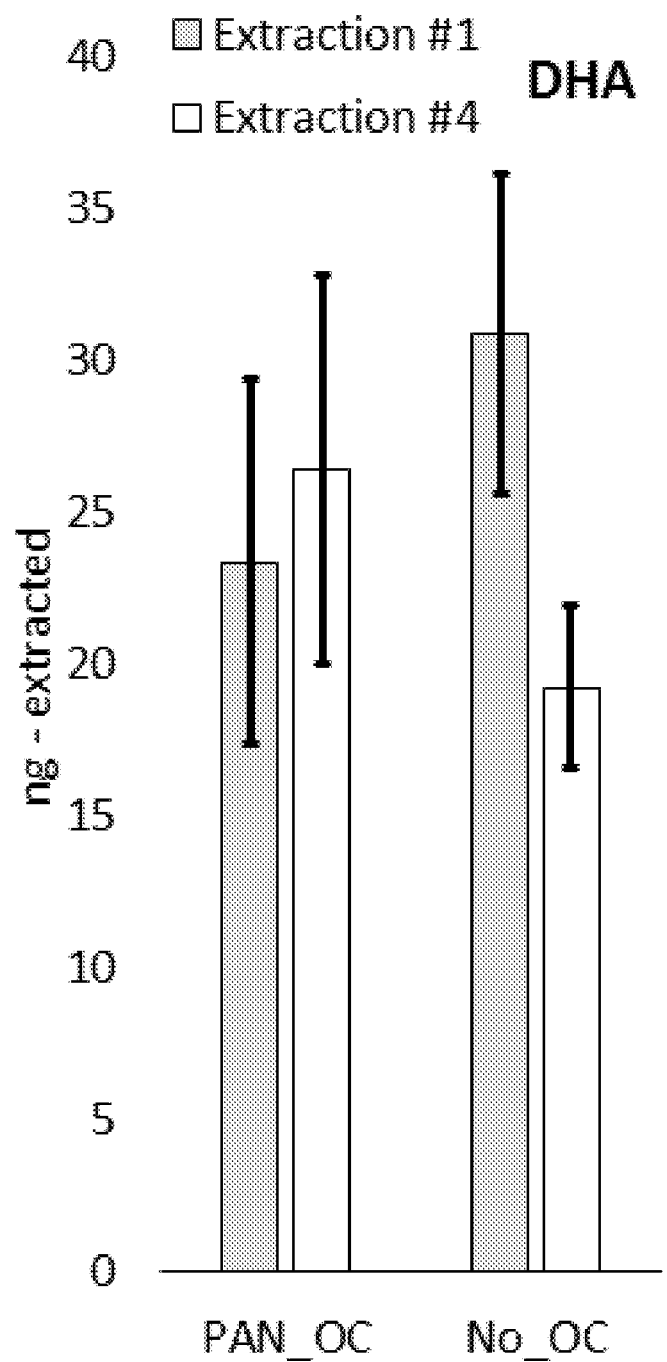

The experimental data shown in FIGS. 22A-B show that the sampling instruments without a PAN over-coating demonstrated a drop in the amount of PUFAs extracted over multiple uses. However, this drop in amount extracted was not observed with the sampling instruments that had a PAN over-coating. This observation leads to the conclusion that the application of a smooth PAN over-coating sampling instrument does indeed increase biocompatibility as indicated by the reduction of matrix effects associated with the sampling biological matrices. In addition, further over-coating could be utilized so as to over-coat the entire instrument in order to provide a completely smooth surface, covering any of the solid substrate used to support the extractive coating and thereby limiting any biological or other activity it may demonstrate while extraction is occurring.

Example 8—In Situ Extraction from Brain Tumors

In order to evaluate the performance and applicability of the sampling instruments according to the present disclosure, in situ extractions from two different types of brain tumors, meningioma and glioma, were performed. Eight sampling instruments were used, four for meningioma brain tumors and four for glioma brain tumors were preconditioned overnight in methanol/water 1:1 v/v, then quickly rinsed in LC-MS grade water (5 sec immersion, no agitation) to remove possible remains of organic solvent from the surface and subsequently inserted to given tumor for 30 min. After extraction, two sampling instruments used for each type of tumor were washed with LC-MS grade water using vortex agitation, while the remaining sampling instruments were washed with 10% acetone using the same agitation conditions. The extracts obtained were then subjected to LC-MS analysis in ESI positive mode using Q-Exactive Focus orbitrap mass spectrometer with the scanning range set for m/z 80-1000. Desorption solutions were analyzed using Analysis method #3 as outlined in Table 4.

TABLE 4

Analysis method #3-Chromatographic solvent gradient and positive H-ESI ionization conditions.
Description:
10 μL of each extract was injected to LC-MS system described above. Separation was performed on Supelco Discovery HS F5 column (2.1 mm × 100 mm × 3 μm). A binary mobile phase system was used. Mobile phase A consisted of 99.9% water and 0.1% formic acid and mobile phase B composed of 99.9% of acetonitrile and 0.1% formic acid. Detail of solvent gradient and MS parameters are provided below.

Mobile phase gradient

| Time (min) | Percent composition A | B | Flow (μL/min) |
|---|---|---|---|
| 0 | 100 | 0 | 300 |
| 3 | 100 | 0 | 300 |
| 25 | 10 | 90 | 300 |
| 34 | 10 | 90 | 300 |
| 34.5 | 100 | 0 | 300 |
| 40 | 100 | 0 | 300 |

Figure 23:
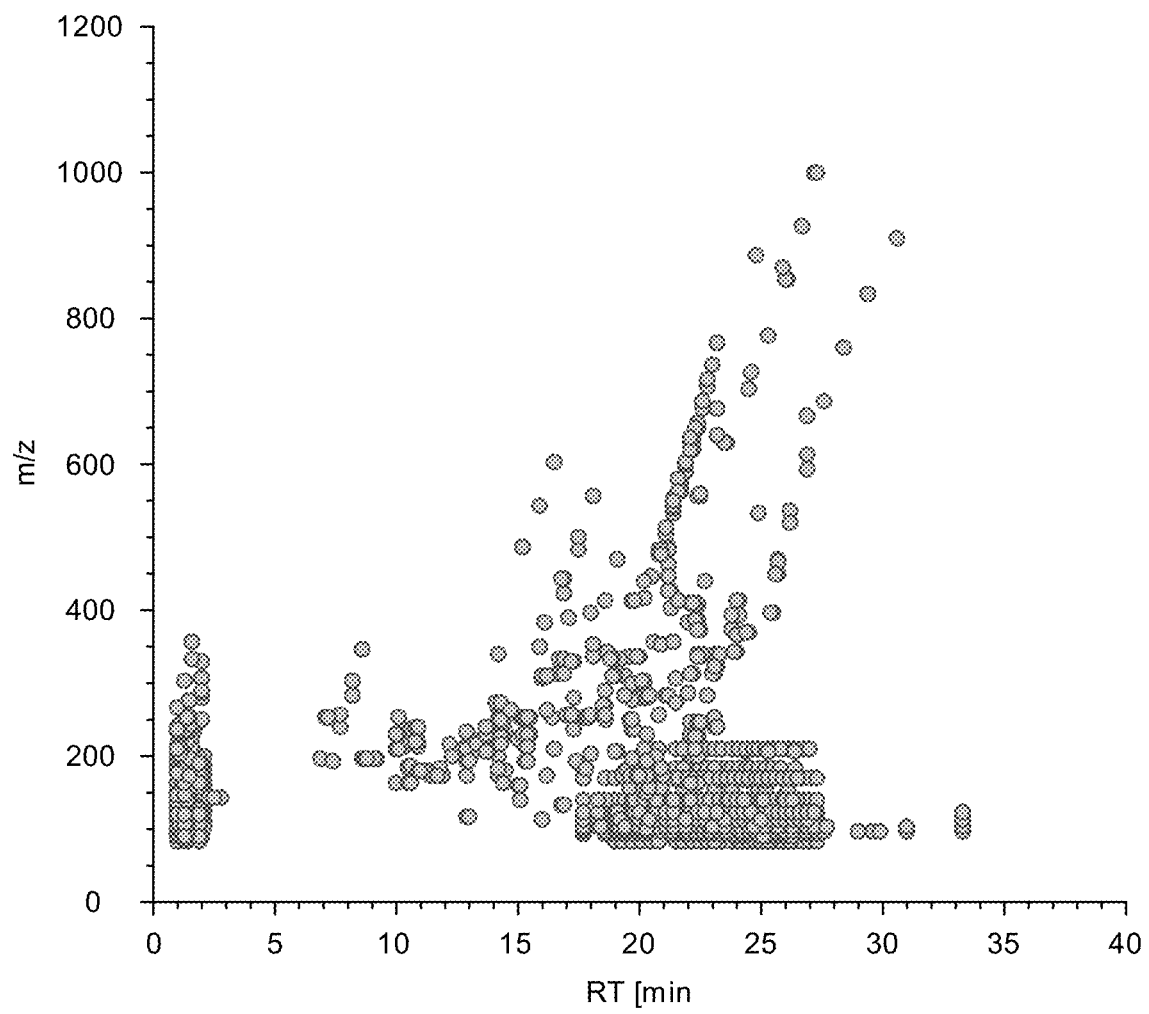
FIG. 23 is a molecular feature map indicating anayte coverage in the extracts obtained from brain tumor tissue using a sampling instrument according to the present disclosure.
Figure 24:
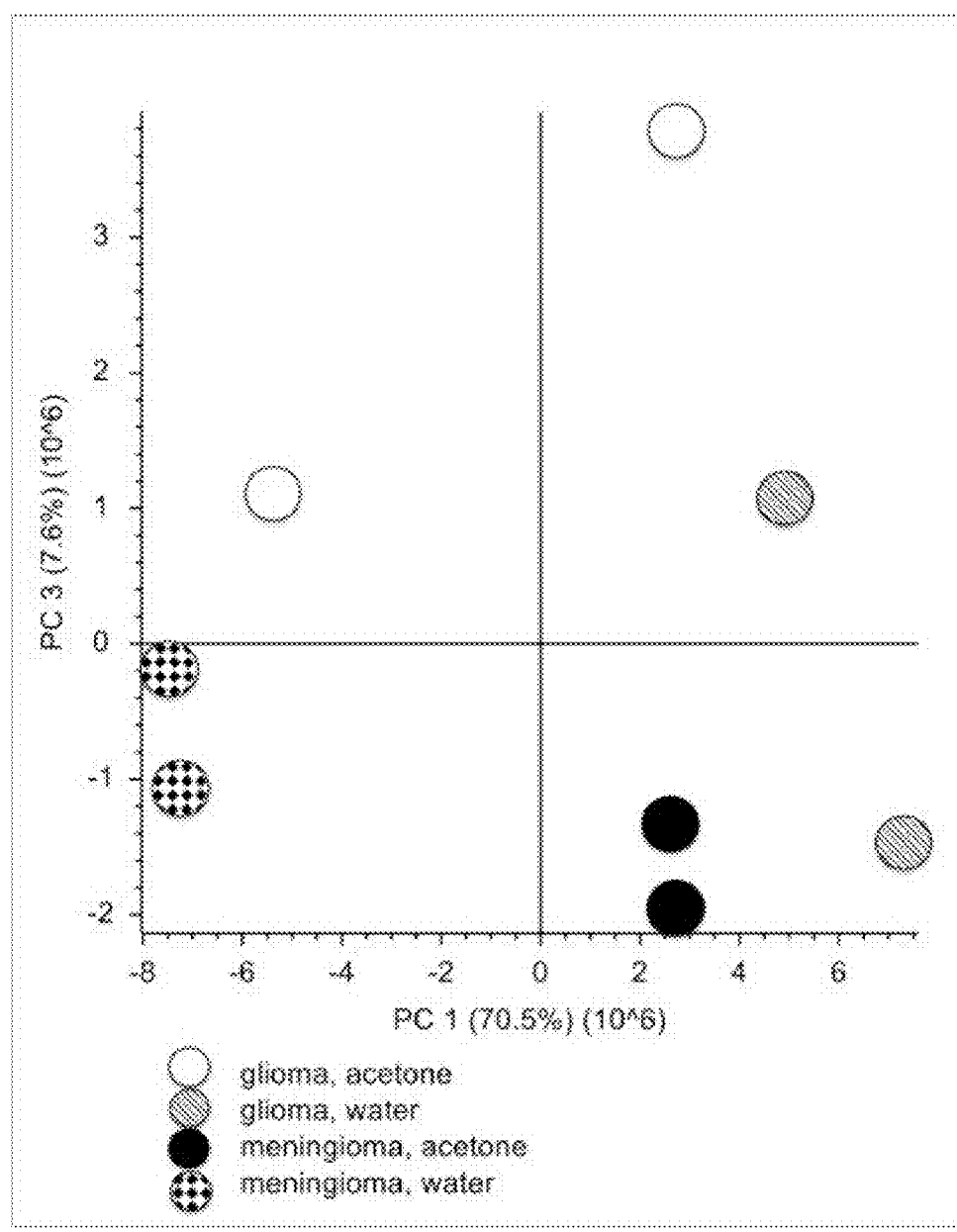
FIG. 24 is a principal component analysis plot demonstrating the separation of two different brain tumors using a sampling instrument according to the present disclosure.

The results obtained indicated that the sampling instruments provide balanced and representative analyte coverage, which allows distinguishing metabolome differences between studied samples/cohorts. In the experiment, an average of 4299 molecular features were detected in the brain tumor extracts, which refers to ca. 147 compounds. The compounds ranged from polar characterized by retention time (RT) of 1.05 min to hydrophobic species with RT 30.06 min (FIG. 23). The separation between two different tumor samples extracted in replicates was observed with both tested SPME protocols (10% acetone wash and water wash), as shown in FIG. 24.

Figure 25:
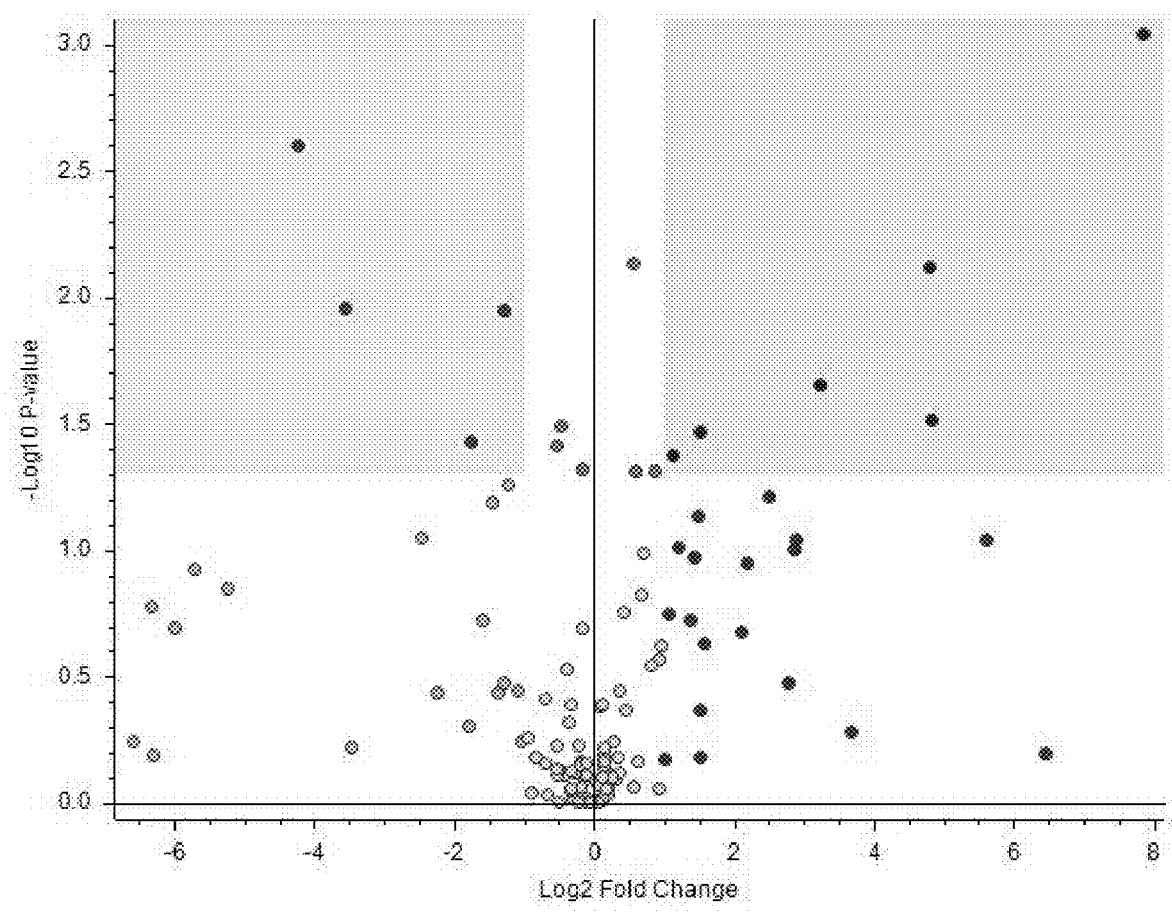
FIG. 25 is a volcano plot showing fold change values and probability levels in discriminating meningioma and glioma components extracted using a sampling instrument according to the present disclosure. The highlighted areas indicate criteria of statistical significance.
Figure 26A:
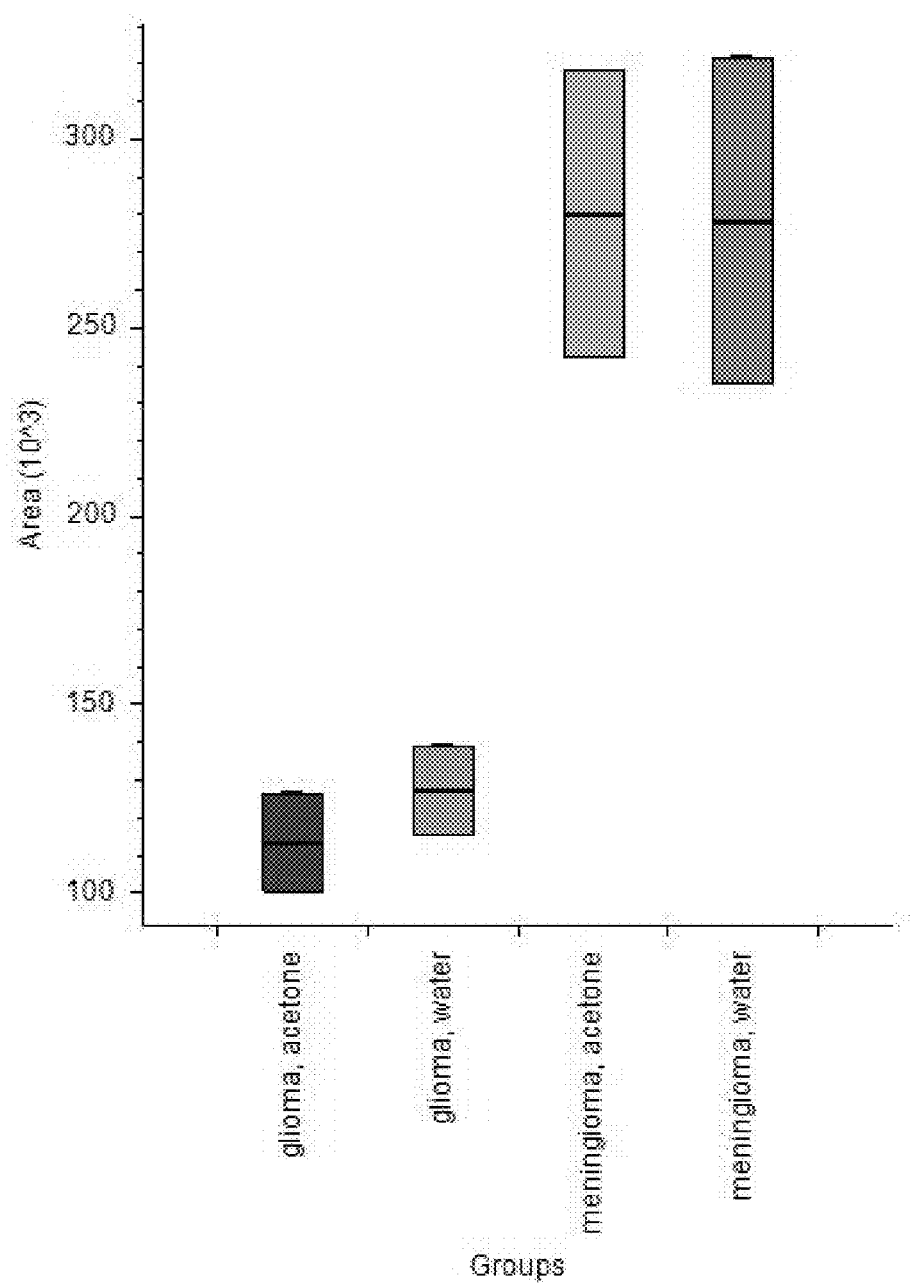
FIGS. 26A-B are box-whisker plots presenting concentration differences in meningioma and glioma samples for two selected examples of compounds with P<0.05 and 1<log 2 Fold change)<−1.
Figure 26B:
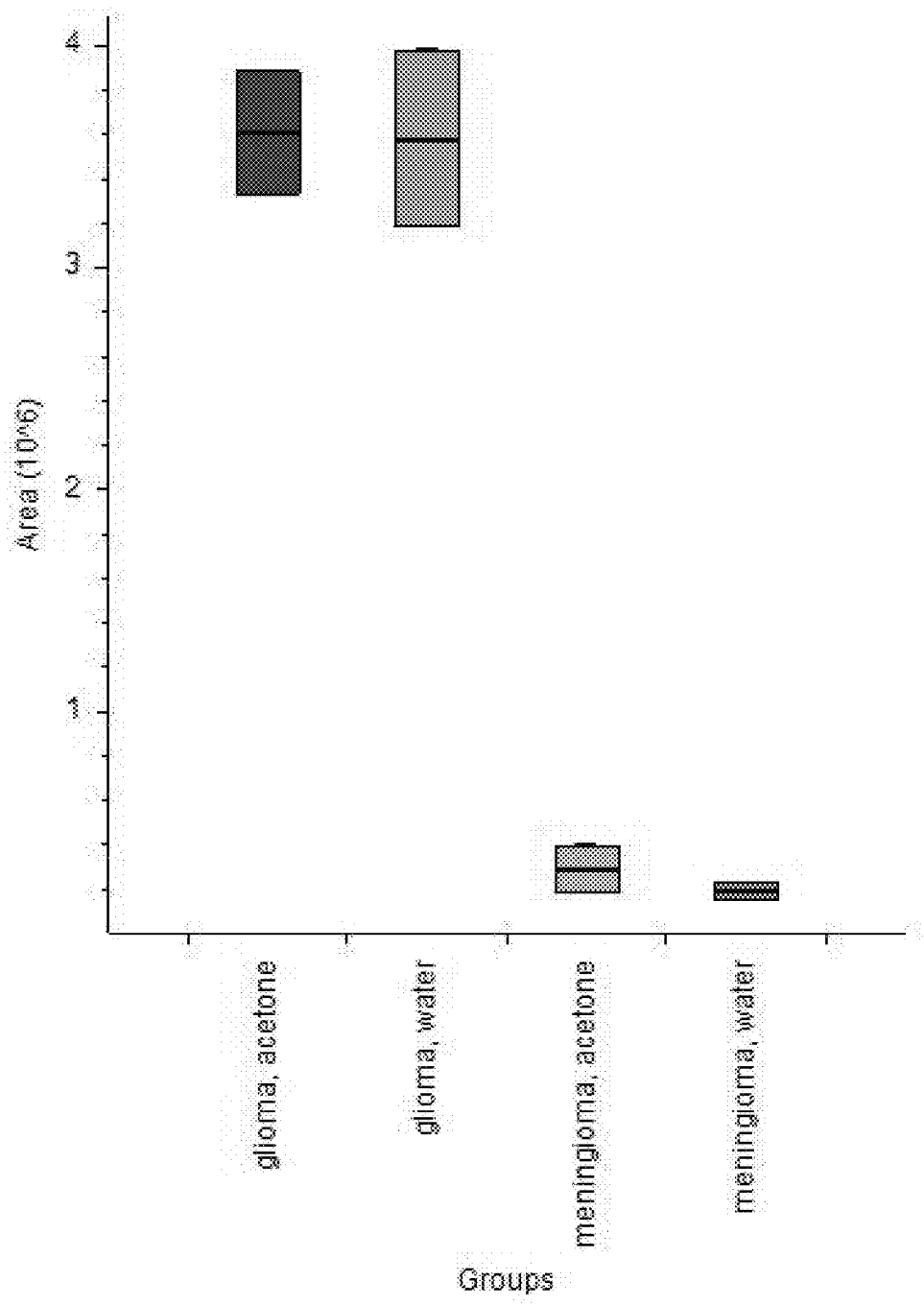

Several compounds showed statistical significance ($P<0.05$ and $1<\log 2$ Fold Change$<-1$) in discrimination of meningioma and glioma samples (FIG. 25), which demonstrates the potential of the use of the sampling instruments in biomarkers analysis. Up- or down-regulation of the exemplary compounds in the studied brain tumor samples are provided in FIGS. 26A-B. Tentative identification revealed that some of the differentiating metabolites i.e. 5-oxoprolina (pyroglutamic acid) were already reported in the literature as the compounds of potential value in brain tumors diagnosis.

Example 9—Coated Biopsy Needle Experiment

The general workflow for a coated biopsy needle experiment was identical to the brain tumor analysis protocol in Example 8, with the exception of the volume of desorption solvent, which was increased to 1.5 mL to increase immersion of the entire coating. As explained above, the major difference in the coated biopsy needle and sampling instrument is the use of tissue withdrawal-free sampling in the latter case and sampling of the collected biopsy sample without its consumption with the coated biopsy needle approach, thus the biopsy sample can be subjected to further testing with routine assays. Here, a fragment of meningioma tissue was collected using standard biopsy protocol for a guillotine biopsy needle. A sampling instrument according to the present disclosure was secured in an outer biopsy sheath during insertion into the tissue, and once within the tissue, the sheath was pulled back to expose the insertion portion of the sampling instrument to allow extraction. After the extraction, the sheath was pulled forward so that the sharp tip of the sheath cut the thin layer of the tissue sitting on the extraction phase coating of the sampling instrument.

Figure 27A:
FIGS. 27A-B are images of integrated biopsy sampling and component extraction using sampling instruments according to the present disclosure.
Figure 27B:
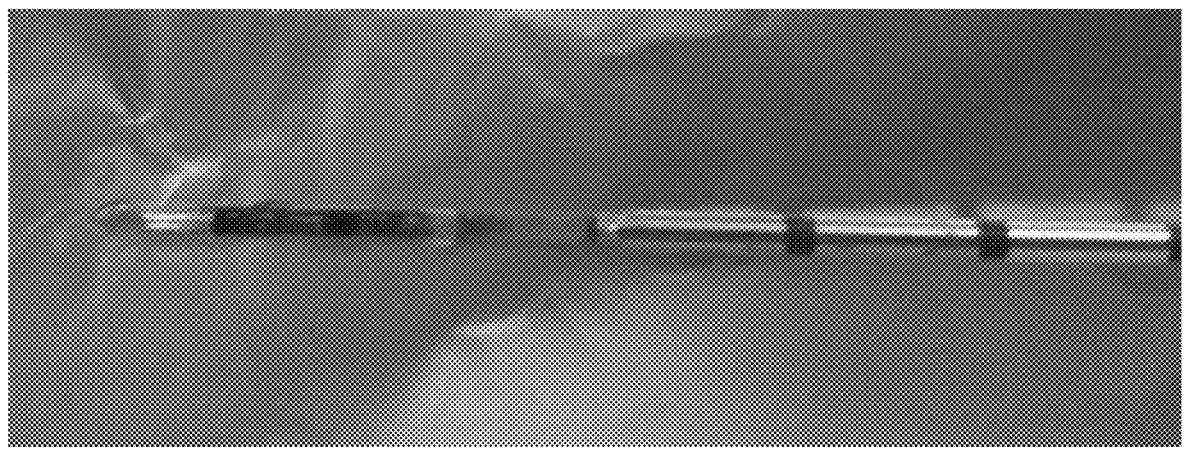

After the cutting, the sampling instrument was withdrawn from the tissue. FIG. 27A is an image during sampling collection and component extraction. FIG. 27B is an image after sampling collection and component extraction. During the extraction, the outer part of the biopsy needle protects the sample from contamination or drying.

The sample was kept on the extraction phase coating for 30 min to ensure extraction of the metabolites. After that time tissue sample was removed from the sampling instrument and the coated part of the sampling instrument was washed with 10% acetone and then subjected to desorption as described in Example 8. The extracts were analyzed using LC/MS conditions provided for brain tumor analysis with SPME needles as described in Table 4.

Figure 28:
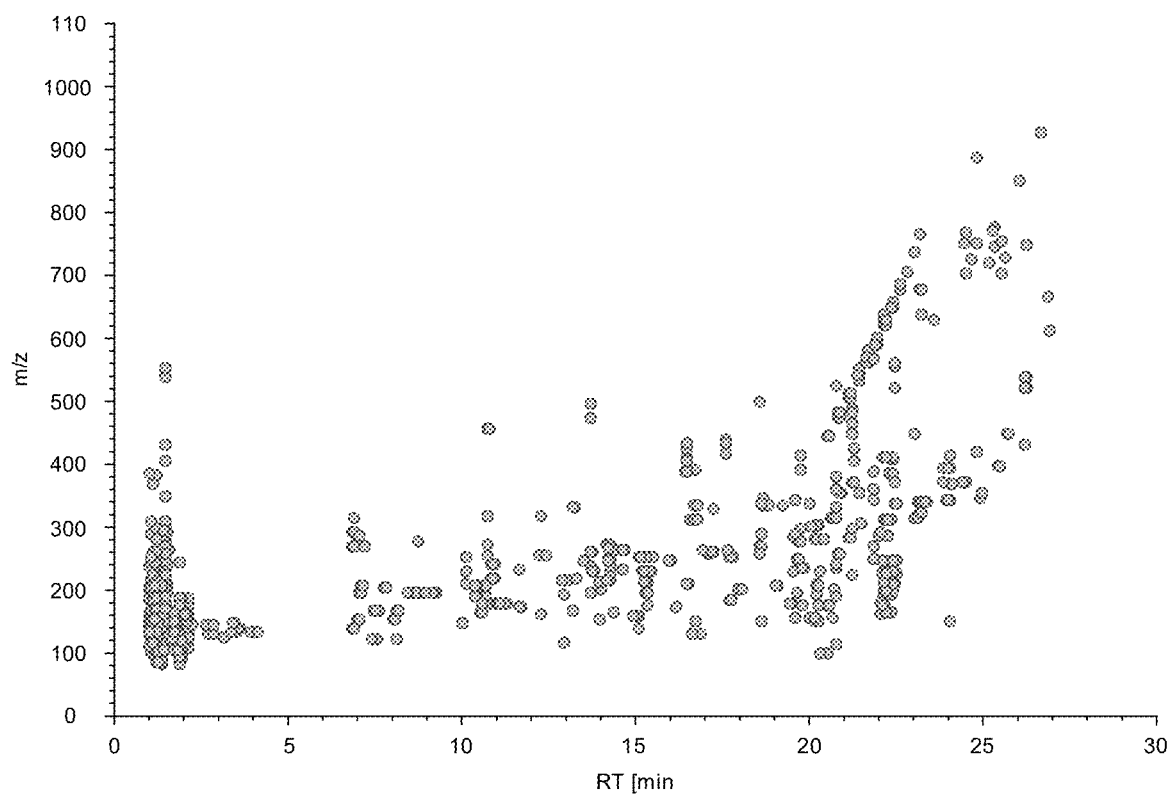
FIG. 28 is a molecular feature map indicating analyte coverage in the extracts obtained from meningioma biopsy sample using a sampling instrument according to the present disclosure.

The results of the experiment revealed applicability of the approach for performing metabolic profile of the tissue from the biopsy sample without sample consumption. The analyte coverage was balanced from polar metabolites with RT from 1.05 to 26.29 (FIG. 28). The number of molecular features and identified compounds was 1740 and 367, respectively. This indicates a potential of the sampling instrument for metabolomics and biomarker analysis and enrich the portfolio of the routine histological tests without additional tissue collection.

In the preceding description, for purposes of explanation, numerous details are set forth in order to provide a thorough understanding of the examples. However, it will be apparent to one skilled in the art that these specific details are not required. The above-described examples are intended to be examples only. Alterations, modifications and variations can be effected to the particular examples by those of skill in the art. The scope of the claims should not be limited by the particular examples set forth herein, but should be construed in a manner consistent with the specification as a whole.

What is claimed is:

1. A solid phase microextraction sampling instrument for inserting into or through a solid or semisolid material to extract a component of interest from a sample, comprising:
   a support structure at least partially coated with an extraction phase for extracting the component of interest, the support structure having:
      an insertion portion for inserting into or through the material and into the sample, the insertion portion comprising:
         a protrusion defining a leading protrusion side and a trailing protrusion side of the insertion portion,
      wherein the extraction phase is located on an exterior portion of the sampling instrument that interacts with the solid or semisolid material during insertion, and
      wherein the extraction phase is located at least on the trailing protrusion side of the protrusion and abuts a trailing side edge of the protrusion, and
      wherein the protrusion projects with a height from the support structure that is approximately equal to the thickness of the extraction phase where the extraction phase abuts the protrusion to shield the coating during insertion in a direction along the axis of insertion of the support structure, and
      wherein the sampling instrument has multiple cross-sectional planes located along the axis of insertion between the insertion end of the insertion portion and the protrusion closest to the insertion end of the insertion portion, each cross sectional plane extending about perpendicularly from the axis of insertion, and defining distances between the axis of insertion and the outer edge of the sampling instrument, wherein each distance of the cross sectional plane at the protrusion closest to the insertion end of the insertion portion is greater than or equal to the corresponding distances of each of the other cross-sectional planes.

2. The sampling instrument of claim 1, wherein the sampling instrument is sheathless.

3. The sampling instrument of claim 1, wherein the protrusion extends around the circumference of the insertion portion of the support structure.

4. The sampling instrument of claim 1, wherein the sampling instrument comprises a plurality of protrusions.

5. The sampling instrument of claim 4, wherein the heights of each one of the plurality of protrusions is approximately equal.

6. The sampling instrument of claim 4, wherein the extraction phase is located between every adjacent pair of protrusions.

7. The sampling instrument of claim 1, wherein the support structure comprises one protrusion that extends around the circumference of the support structure in a screw-like configuration.

8. The sampling instrument of claim 7, wherein the extraction phase is located between every adjacent pair of threads of the screw-like protrusion.

9. The sampling instrument of claim 1, wherein the extraction phase comprises a sorptive polymer or a combination of a polymer and a sorptive material immobilized in the polymer.

10. The sampling instrument of claim 9, wherein the sorptive material comprises: normal-phase silica particles, C-1/silica particles, C-4/silica particles, C-6/silica particles, C-8/silica particles, C-18/silica particles, C-30/silica particles, reverse-phase amide silica particles, HS-F5/silica particles, phenyl/silica particles, cyano/silica particles, diol/silica particles, ionic liquid/silica particles, molecular imprinted polymer particles, hydrophilic-lipophilic-balanced (HLB) particles, carboxen 1006 particles, carbowax particles, divinylbenzene (DVB) particles, octadecylsilane particles, nano particles, processed mineral based particles, carbon nanotubes, functionalized-carbon nanotubes, graphene, graphene oxide, functionalized-graphene, quantum dots, or any combination thereof.

11. The sampling instrument of claim 9, wherein the sorptive polymer comprises an organic polymer such as poly di-vinyl benzene (DVD), polydimethysiloxane (PDMS), hydrophilic lipophilic balanced (HLB), or polyethylene glycol (PEG).

12. The sampling instrument of claim 1, wherein the support structure is configured to control the depth of insertion into the sample.

13. The sampling instrument of claim 1, further comprising an additional coating located over at least the insertion portion of the instrument.

14. The sampling instrument of claim 13, wherein the additional coating is comprised of a biocompatible polymeric coating comprising polyacrylonitrile, Polytetrafluoroethylene, polydimethylsiloxane, polyethylene glycol, or a combination thereof.

15. The sampling instrument of claim 1, wherein the solid or semisolid material is a tissue, a membrane, or a septum.

16. The sampling instrument of claim 1, wherein the solid or semisolid material is part of the sample or is the same as the sample.

17. The sampling instrument of claim 1, wherein the sample is a fruit, a vegetable, or a biological tissue, such as organ tissue, epithelial tissue, muscle tissue, nervous tissue, connective tissue, or mineralized tissue, brain tissue, or fish tissue.

18. The sampling instrument of claim 1, wherein the component of interest is a bacteria, a virus, a sub-cellular component, a biopolymer, DNA, a protein, a drug, a drug metabolite, a hormone, a vitamin, an environmental contaminant, a chemical, a cell, or a combination thereof.

19. A method for extracting a component of interest from a sample, the method comprising:
   inserting an instrument as defined in claim 1 into or through a solid or semisolid material and into the sample;
   sorbing the component of interest; and
   removing the instrument from the sample.

20. The method of claim 19, further comprising positioning the extraction phase into an analytical instrument for desorption, and measurement or identification of the component of interest.

* * * * *